(12) United States Patent
Lee et al.

(10) Patent No.: US 11,628,000 B2
(45) Date of Patent: Apr. 18, 2023

(54) HYBRID BONE PLATE

(71) Applicant: GLW, Inc., Waxhaw, NC (US)

(72) Inventors: Thomas Hoon Lee, Columbus, OH (US); Axel Cremer, Fahrenkrug (DE); Richard Garret Mauldin, Erie, CO (US); Arley Perez, Wayne, NJ (US); Jan Heinsohn, Boca Raton, FL (US)

(73) Assignee: GLW, Inc., Englewood Cliffs, NJ (US)

( * ) Notice: Subject to any disclaimer, the term of this patent is extended or adjusted under 35 U.S.C. 154(b) by 502 days.

(21) Appl. No.: 16/822,243

(22) Filed: Mar. 18, 2020

(65) Prior Publication Data

US 2020/0297400 A1  Sep. 24, 2020

Related U.S. Application Data

(60) Provisional application No. 62/927,949, filed on Oct. 30, 2019, provisional application No. 62/819,991, filed on Mar. 18, 2019.

(51) Int. Cl.
*A61B 17/80* (2006.01)
*A61L 31/02* (2006.01)
*A61L 31/04* (2006.01)
*A61B 17/00* (2006.01)

(52) U.S. Cl.
CPC .......... *A61B 17/80* (2013.01); *A61B 17/8028* (2013.01); *A61L 31/022* (2013.01); *A61L 31/048* (2013.01); *A61B 2017/0092* (2013.01); *A61B 2017/00526* (2013.01); *A61B 2017/00955* (2013.01)

(58) Field of Classification Search
CPC .................................................... A61B 17/80
See application file for complete search history.

(56) References Cited

U.S. PATENT DOCUMENTS

| 4,280,233 A | 7/1981 | Raab |
| 4,338,926 A | 7/1982 | Kummer et al. |
| 5,571,139 A | 11/1996 | Jenkins, Jr. |
| 7,033,398 B2 | 4/2006 | Graham |

(Continued)

FOREIGN PATENT DOCUMENTS

| CN | 101128157 | 2/2008 |
| CN | 101426444 | 5/2009 |

(Continued)

OTHER PUBLICATIONS

PCT Search Report and Written Opinion, Application No. PCT/US2020/023280, dated Aug. 18, 2020.

*Primary Examiner* — Christian A Sevilla
(74) *Attorney, Agent, or Firm* — MacMillan, Sobanski & Todd, LLC

(57) ABSTRACT

A bone fixation plate comprises a main body formed of a first material and a support member formed of a second, different material and attached to the main body. The main body defines a first set of openings and the support member defines a second set of openings aligned with the first set of openings. For each opening of the first set of openings, a main body circumferential surface is disposed adjacent and continuous with a support member circumferential surface of the second set of openings to define an opening circumferential surface that bounds an opening of the first set of openings and an opening of the second set of openings.

18 Claims, 32 Drawing Sheets

(56) References Cited

U.S. PATENT DOCUMENTS

| | | |
|---|---|---|
| 7,850,690 B2 | 12/2010 | Frigg et al. |
| 8,092,505 B2 | 1/2012 | Sommers |
| 8,454,606 B2 | 6/2013 | Frigg et al. |
| 8,663,224 B2 | 3/2014 | Overes et al. |
| 8,702,767 B2 | 4/2014 | Nebosky et al. |
| 8,709,055 B2 | 4/2014 | Beyar et al. |
| 8,784,430 B2 | 7/2014 | Kay et al. |
| 8,979,865 B2 | 3/2015 | Fan et al. |
| 8,998,987 B2 | 4/2015 | Wallick |
| 9,101,417 B2 | 8/2015 | Beyar et al. |
| 9,174,390 B2 | 11/2015 | Lechmann et al. |
| 9,440,379 B2 | 9/2016 | Smith et al. |
| 9,452,001 B2 | 9/2016 | Faccioli et al. |
| 9,492,210 B2 | 11/2016 | Rains et al. |
| 9,770,273 B2 | 9/2017 | Guitelman |
| 10,022,164 B2 | 7/2018 | Mangiardi |
| 10,022,165 B2 | 7/2018 | Mangiardi |
| 10,028,777 B2 | 7/2018 | Beyar et al. |
| 2006/0247638 A1 | 11/2006 | Trieu et al. |
| 2007/0049938 A1 | 3/2007 | Wallace et al. |
| 2007/0049939 A1 | 3/2007 | Wallace et al. |
| 2007/0049940 A1 | 3/2007 | Wallace et al. |
| 2007/0233071 A1 | 10/2007 | Dewey et al. |
| 2009/0018590 A1 | 1/2009 | Dorawa et al. |
| 2009/0043307 A1 | 2/2009 | Faccioli et al. |
| 2009/0299369 A1* | 12/2009 | Orbay .................... A61B 17/80 606/70 |
| 2010/0114097 A1 | 5/2010 | Siravo et al. |
| 2010/0211118 A1 | 8/2010 | Christen et al. |
| 2011/0093020 A1 | 4/2011 | Wu |
| 2011/0208189 A1 | 8/2011 | Faccioli et al. |
| 2011/0218570 A1* | 9/2011 | Felix .................... A61L 31/18 606/280 |
| 2011/0245832 A1 | 10/2011 | Giersch et al. |
| 2011/0288596 A1* | 11/2011 | Brand .................... A61B 50/20 606/286 |
| 2012/0271361 A1 | 10/2012 | Zhou et al. |
| 2014/0105776 A1 | 4/2014 | Ellero et al. |
| 2014/0188113 A1 | 7/2014 | Overes et al. |
| 2017/0056081 A1* | 3/2017 | Langdale ........... A61B 17/8057 |
| 2017/0105776 A1 | 4/2017 | Lutz |
| 2018/0036047 A1* | 2/2018 | Torres ................ A61B 17/8033 |
| 2018/0049782 A1* | 2/2018 | Gahman ............ A61B 17/8014 |
| 2019/0053836 A1 | 2/2019 | Sweeney et al. |
| 2019/0216513 A1 | 7/2019 | Sands et al. |

FOREIGN PATENT DOCUMENTS

| | | |
|---|---|---|
| CN | 101686844 | 3/2010 |
| CN | 102355863 | 2/2012 |
| CN | 102008751 | 1/2014 |
| DE | 102013013138 A1 | 9/2014 |
| EP | 1265653 | 6/2004 |
| GB | 2405342 A | 3/2005 |
| JP | H07213534 | 8/1995 |
| WO | WO2001074262 | 10/2001 |
| WO | WO2004024012 | 3/2004 |
| WO | WO2007101267 | 9/2007 |
| WO | WO2008134264 | 11/2008 |
| WO | WO2011066522 | 6/2011 |
| WO | WO2011082152 | 7/2011 |
| WO | WO20120065068 | 5/2012 |
| WO | WO20140152262 | 1/2014 |
| WO | WO2015137911 | 9/2015 |
| WO | WO2015172842 | 11/2015 |
| WO | WO2016125054 | 8/2016 |
| WO | 2018013594 A1 | 1/2018 |

* cited by examiner

HYBRID BONE PLATE

CROSS-REFERENCE TO RELATED APPLICATIONS

This application claims the benefit of U.S. Provisional Application No. 62/819,991, filed on Mar. 18, 2019, and U.S. Provisional Application No. 62/927,949, filed on Oct. 30, 2019. The entire contents of each of these applications is hereby incorporated into this disclosure in their entirety.

FIELD

The disclosure relates to the field of medical devices. More particularly, the disclosure relates to the field of orthopedic medical devices. Specific examples relate to plates and screws for internal fixation of bone fractures.

BACKGROUND

Bone plates have been widely used for internal fixation of fractures for years. Indeed, various bone plate structures are known in the art. For example, some conventional bone plates are constructed from either metal, such as titanium alloys and stainless steel, or polymers, such as carbon fiber or polyethertherketone ("PEEK").

While conventional bone plates are widely used, they do have several drawbacks. For example, while metal plates typically demonstrate adequate wear resistance and strength, conventional solid metal construction hinders a user's ability to visualize the fracture site while using X-ray imaging techniques and equipment. Titanium plates often require the use of a computed tomography (CT) scan to image a fracture site when assessing healing of the bone, which exposes a patient to a higher level of radiation than that involved in a standard X-ray. Moreover, while carbon fiber and PEEK bone plates provide an option for increased visibility of the fracture site using standard X-ray imaging, these plates must be significantly thicker than metal bone plates to achieve desirable strength. Furthermore, PEEK bone plates can also be entirely transparent, which creates additional challenges when attempting to visualize the position of the plate in post-operative evaluations.

A need exists, therefore, for improved bone plates.

BRIEF SUMMARY OF SELECTED EXAMPLES

Various example bone plates are described herein.

An example bone plate includes a main body and a support member. A main body has a main body first end, a main body second end, a main body third end, and a main body fourth end. The main body also defines a first surface that includes a continuous first surrounding edge. The main body also defines a second surface that includes a continuous second surrounding edge. The main body has a first set of openings that extends through the main body between the first and second surfaces. The main body also defines at least one wall. The support member is disposed on the main body. The support member has a support member first end and a support member second end. The support member has a third surface that interfaces with the first and second surfaces and the wall, a fourth surface, and a second set of openings that is formed about the first set of openings.

Another example bone plate has a main body and a support member. The main body has a main body first end, a main body second end, a main body third end, and a main body fourth end. The main body has a first surface that includes a continuous first surrounding edge, and the main body has a second surface that includes a continuous second surrounding edge. The first and second surfaces are parallel to each other but directly oppose each other. The bone plate also has a first set of openings that extends through the main body between the first and second surfaces. The main body also has at least two walls. The support member is formed on the main body that has a support member first end and a support member second end. The support member has a third surface that interfaces with the first and second surfaces and the wall, a fourth surface, and a second set of openings that are formed about the first set of openings. The main body is made of a first material and the support member is made of a second material.

Another example bone plate has a main body and a support member. The main body has a main body first end, a main body second end, a main body third end, and a main body fourth end. The main body has a first surface that includes a continuous first surrounding edge, and the main body has a second surface that includes a continuous second surrounding edge. The main body includes a first set of openings that extend through the main body between the first and second surfaces. The main body also has first and second walls. The support member is formed about the main body that has a support member first end and a support member second end. The support member has a third surface that interfaces with the first and second surfaces and the wall. The support member has a fourth surface and a second set of openings formed about the first set of openings. The main body is made of a first material and the support member is made of a second material. The first wall defines a first portion, a second portion, and a third portion, and second wall defines a fourth portion and a fifth portion. The first portion defines a first length measured between the second portion and the fourth portion, a second length measured between the fourth portion and fifth portion, and a third length measured between the fifth portion and the third portion. Each of the second and third portions defines a fourth length measured between first or second surfaces to the main body third or fourth ends. Each of the fourth and fifth portions defines a fifth length measured between first or second surfaces to the main body third or fourth end. The second length is greater than the first and third lengths, and the fourth length is greater than the fifth length.

Another example bone plate has a main body and a support member. The main body has a main body first end, a main body second end, a main body lengthwise axis that extends between the main body first end and the main body second end, a first surface, a second surface, a first set of openings disposed between the main body first and second ends, and a first wall. The first and second surfaces directly oppose each other. The support member is secured to the main body. The support member has a first end, a support member second end, a support member lengthwise axis that extends between the support member first end and the support member second end, a third surface that interfaces with the main body, and a fourth surface that interfaces with the external environment.

Another example bone plate has a main body and a support member. The main body has a main body first end, a main body second end, a main body lengthwise axis that extends between the main body first end and the main body second end, a first surface, a second surface, a first set of openings disposed between the main body first and second ends, and a first wall. The first and second surfaces directly oppose each other. Each opening of the first set of openings defines a recess and a locking member. The recess extends from the first surface to a recess base, and the locking member is disposed at the recess base. The support member is secured to the main body. The support member has a support member first end, a support member second end, a support member lengthwise axis that extends between the support member first end and the support member second end, a third surface that interfaces with the main body, and a fourth surface that interfaces with the external environment. The main body is made of a first material and the support member is made of a second material.

Another example bone fixation plate has a main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings disposed between the main body first and second ends, and a first wall that extends between the main body first and second ends. The first and second surfaces directly oppose each other. Each opening of the first set of openings defines a recess and a locking member. The recess extends from the first surface to a recess base, and the locking member is disposed at the recess base and defines a plurality of notches. The first wall defines a plurality of passageways that extends from the first surface to the second surface of the main body. The support member is formed to the first surface, the second surface, and the wall. The support member has a support member first end, a support member second end, a support member lengthwise axis that extends between the support member first end and support member second end, a third surface that interfaces with the main body, a fourth surface that interfaces with the external environment, and a second set of openings that is disposed between the support member first end and the support member second end. The second set of openings is also disposed radially about the first set of openings on the first and second surfaces. The main body is made of a first material and the support member is made of a second material.

Another example bone plate has a main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings that is disposed between the main body first and second ends, a first wall, and a second wall. The first and second surfaces directly oppose each other. Each opening of the first set of openings defines a recess and a locking member. The recess extends from the first surface to a recess base, and the locking member is disposed at the recess base that defines a plurality of notches. The first and second walls cooperatively define a chamber. The first wall defines a first set of passageways that extends from the first surface to the chamber. The second wall defines a second set of passageways that extends from the second wall to the chamber. The first and second set of passageways and the chamber are in communication with each other. The support member is formed into the first set of passageways, the second set of passageways, and the chamber. The support member has a support member first end, a support member second end, a support member lengthwise axis that extends between the support member first end and support member second end, a third surface that interfaces with the main body, and a fourth surface that interfaces with the external environment. The support member is also a precursor material prior to being formed into the main body. The main body is made of a first material and the support member is made of a second material.

Another example bone plate has a main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings that is disposed between the main body first and second ends, and a first wall. The first and second surfaces directly oppose each other. Each opening of the first set of openings defines a recess and a locking member. The recess extends from the first surface to a recess base, and the locking member is disposed at the recess base and defines a plurality of notches. A portion of the first wall extends away from the first surface or second surface of the main body. The support member is formed to the wall. The support member has a support member first end, a support member second end, a support member lengthwise axis that extends between the support member first end and support member second end, a third surface that interfaces with the main body, a fourth surface that interfaces with the external environment, and a second set of openings that is disposed between the support member first end and the support member second end. The second set of openings is disposed radially about the first set of openings on the first surface or second surface. The main body is made of a first material and the support member is made of a second material.

Another example bone plate has a main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings that is disposed between the main body first and second ends, and a first wall. The first and second surfaces directly oppose each other. Each opening of the first set of openings defines a recess and a locking member. The recess extends from the first surface to a recess base, and the locking member is disposed at the recess base that defines a plurality of notches. The first wall extends away from the first surface and defines at least one projection that extends away from the wall and the first surface. The support member is formed to the wall and the at least one projection. The support member has a support member first end, a support member second end, a support member lengthwise axis that extends between the support member first end and support member second end, a third surface that interfaces with the main body, a fourth surface interfaces with the external environment, and a second set of openings that is disposed between the support member first end and the support member second end. The second set of openings is disposed radially about the first set of openings on the second surface. The main body is made of a first material and the support member is made of a second material.

Another example bone plate has a main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings that is disposed between the main body first and second ends, and a first wall. The first and second surfaces directly oppose each other. Each opening of the first set of openings defines a recess and a locking member. The recess extends from the first surface to a recess base, and the locking member is disposed at the recess base and defines a plurality of threads. A portion of the first wall extends away from the first surface or second surface. The support member is formed to the wall. The support member has a support member first end, a support member second end, a support member lengthwise axis that extends between the support member first end and support member second end, a third surface that interfaces with the main body, a fourth surface that interfaces with the external environment, and a second set of openings that is disposed between the support member first end and the support member second end. The second set of openings is disposed radially about the first set of openings on the first surface. The main body is made of a first material and the support member is made of a second material.

Another example bone plate has a main body and a support member. The main body has a main body first end, a main body second end, a main body third end, a main body fourth end, a main body lengthwise axis extending between the main body first end and the main body second end, a first surface that includes a continuous first surrounding edge, a second surface that includes a continuous second surrounding edge, a first set of openings that is disposed between the main body first and second ends, and a first wall. The first and second surfaces directly oppose each other. Each opening of the first set of openings defines a recess and a locking member. The recess extends from the first surface to a recess base, and the locking member is disposed at the recess base that defines a plurality of notches. A portion of the first wall extends away from the second surface. The support member is formed to the wall. The support member has a support member first end, a support member second end, a support member lengthwise axis that extends between the support member first end and support member second end, a third surface that interfaces with the main body, a fourth surface that interfaces with the external environment, and a second set of openings that is disposed between the support member first end and the support member second end. The second set of openings is disposed radially about the first set of openings on the second surface. The main body is made of a first material and the support member is made of a second material.

Another example bone plate has main body and a support member. The main body has a main body first end, a main body second end, a main body third end, a main body fourth end, a main body lengthwise axis that extends between the main body first end and the main body second end, a first surface that includes a continuous first surrounding edge, a second surface that includes a continuous second surrounding edge, a first set of openings that is disposed between the main body first and second ends, and a first wall. The first and second surfaces directly oppose each other. Each opening of the first set of openings defines a recess and a locking member. The recess extends from the first surface to a recess base, and the locking member is disposed at the recess base and defines a first plurality of pegs and a second plurality of pegs. The first plurality of pegs is disposed on a first plane and a second plurality of pegs is disposed on a second plane. The support member is formed to the second surface, the wall, the first plurality of pegs, and the second plurality of pegs. The support member has a support member first end, a support member second end, a support member lengthwise axis that extends between the support member first end and support member second end, a third surface that interfaces with the main body, a fourth surface that interfaces with the external environment, and a second set of openings disposed between the support member first end and the support member second end. The second set of openings is disposed radially about the first set of openings on the second surface. The main body is made of a first material and the support member is made of a second material.

DESCRIPTION OF FIGURES

FIG. 34 illustrates a partial cross-sectional view of another example bone plate.

FIG. 35 illustrates a cross-sectional view of the bone plate illustrated in FIG. 34.

DETAILED DESCRIPTION OF SELECTED EXAMPLES

The following detailed description and the appended drawings describe and illustrate various example bone plates. The description and drawings are provided to enable one skilled in the art to make and use one or more example bone plates. They are not intended to limit the scope of the claims in any manner.

FIGS. 1, 2, 3, and 4 illustrate an example bone plate 100. The bone plate 100 has a main body 110 and a support member 150.

Figure 2:
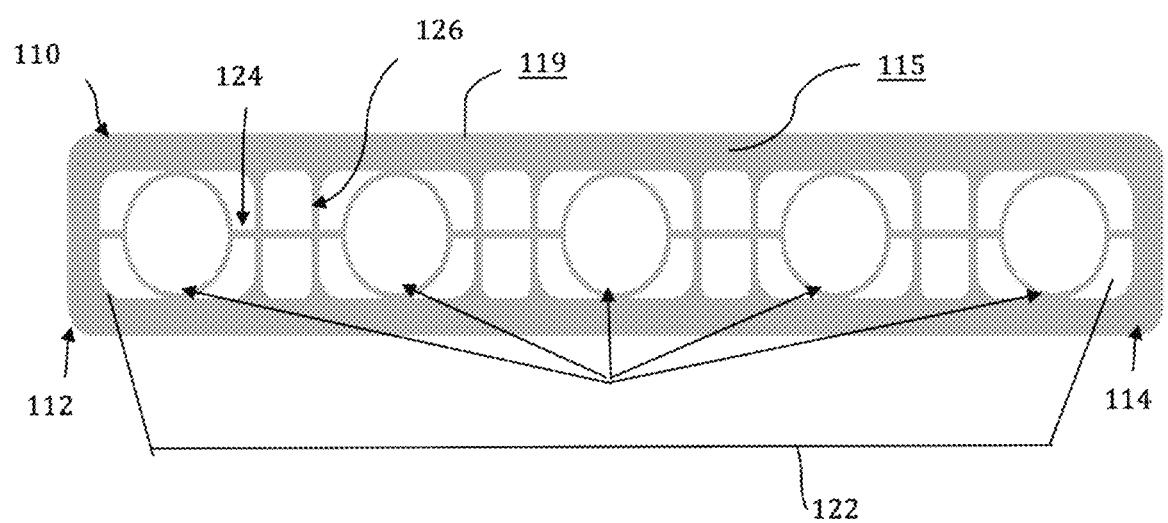
FIG. 2 illustrates a top view of the main body of the example bone plate illustrated in FIG. 1.
Figure 3:
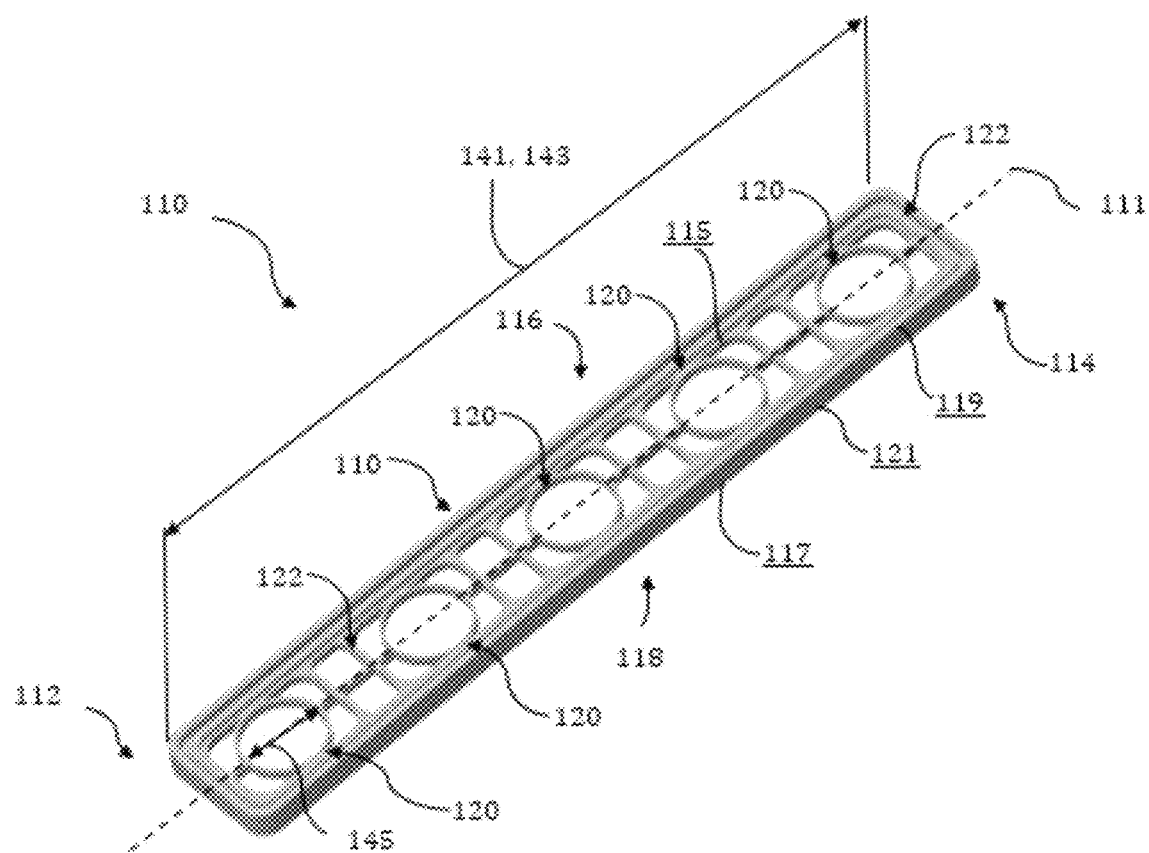
FIG. 3 illustrates a perspective view of the main body of the example bone plate illustrated in FIG. 1.

As illustrated in FIGS. 2 and 3, the main body 110 has a main body first end 112, a main body second end 114, a main body third end 116, a main body fourth end 118, a lengthwise axis 111 that extends between the main body first and second ends 112, 114, a first surface 115, a second surface 117, a first surrounding edge 119, a second surrounding edge 121, a first set of openings 120, and a wall 122.

The first surface 115 extends between the main body first and second ends 112, 114 with a first surface length 141. The first surface 115 is disposed on a first plane that is parallel to main body 110 relative to the lengthwise axis 111 of the main body 110. Similarly, the second surface 117 also extends between the main body first and second ends 112, 114 with a second surface length 143. However, the second surface 117 is disposed on a second plane that is parallel to the main body 110 relative to lengthwise axis 111 of the main body 110. The first and second planes of the first and second surfaces 115, 117 are parallel to each other, but directly oppose each other.

As illustrated in FIGS. 2 and 3, the first surrounding edge 119 is defined between the main body first and second ends 112, 114 and along the first surface 115. The first surrounding edge 119 has a first height (not illustrated) that is measured from the main body third end 116 toward the medial portion of the main body 110. Similarly, the second surrounding edge 121 is also defined between the main body first and second ends 112, 114 and along the main body second surface 117. The second surrounding edge 121 has a second height (not illustrated) that is measured from the main body fourth end 118 toward the medial portion of the main body 110. Moreover, the first and second surrounding edges 119, 121 are parallel to each other relative to the lengthwise axis 111 of the main body 110, but directly oppose each other.

Figure 1:
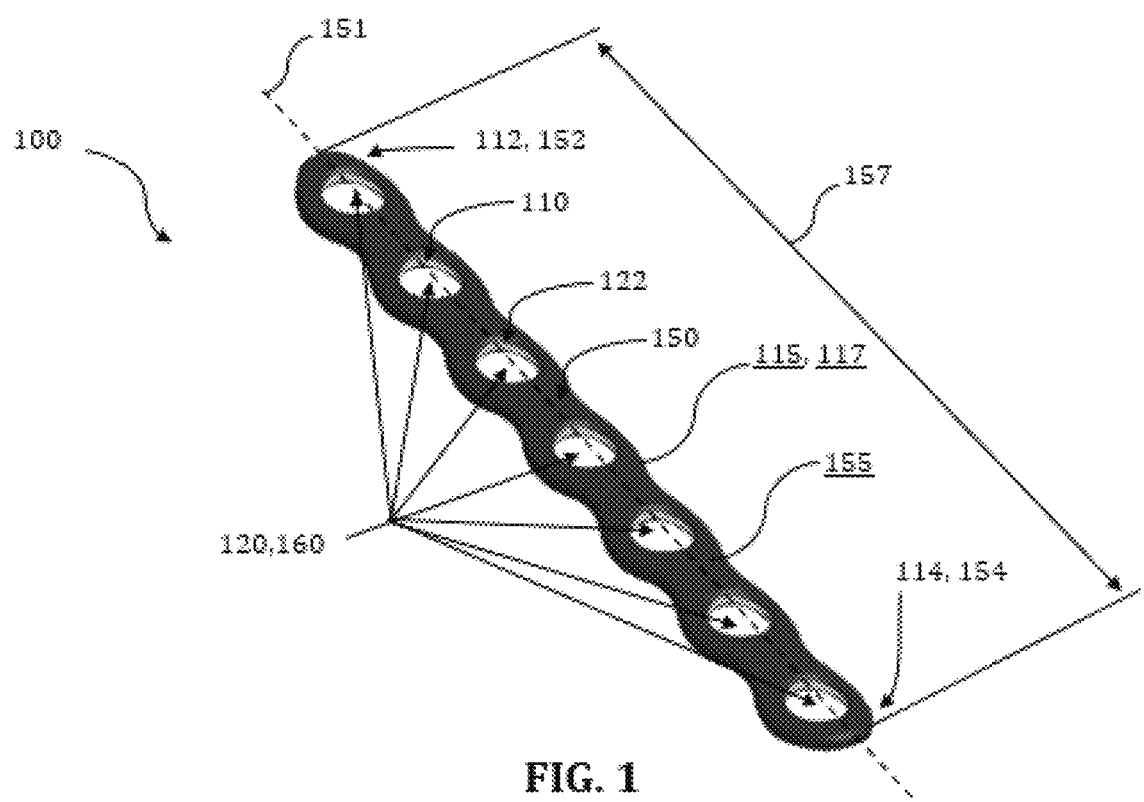
FIG. 1 illustrates a perspective view of an example bone plate.

The main body also defines a first set of openings 120. Each opening of the first set of openings 120 extends entirely through the main body 110 such that each opening extends from the first surface 115 to the second surface 117. Each opening of the first set of openings 120 has a diameter 145 that is sized and configured to receive a screw (not illustrated) or suitable medical device during use. Additionally, as illustrated in FIG. 1, each opening of the first set of openings is sized and configured to interface with a second set of openings 160 of the support member 150 once the support member 150 is attached to the main body 110, which is described in more detail below.

Each opening of the first set of openings 120 may have any suitable size, shape, and structural configuration, and a skilled artisan will be able to select an appropriate configuration for an opening according to an embodiment based on various considerations, including the size, shape, and configuration of a screw or a medical device that is receive by each opening. Examples of suitable configuration include circular, substantially circular, ovoidal, elliptical, rectangular, triangular, or any other suitable structural configuration for a particular application. In the illustrated embodiment, each opening of the first set of openings 120 includes a circular shape. Additionally, main body 110 may have any suitable number of openings for a first set of openings 120, and a skilled artisan will be able to select an appropriate number of openings according to an embodiment based on various considerations, including the size, shape and configuration of an support member. Examples of a suitable number of openings disposed on a main body include, but are not limited to, one, two, plurality, three, four, five, six, or any other suitable number of openings of a first set of openings for a particular application. In the illustrated embodiment, the main body 110 includes five openings for the first set of openings 120.

In the illustrated embodiment, the wall 122 extends between the main body first and second ends 112, 114. The wall 122 lies on a plane that is parallel to the main body 110 relative to the lengthwise axis 111 of the main body 110. As best illustrated in FIGS. 2 and 3, the wall 122 defines a repetitive pattern that extends entirely through main body 110 such that the wall 122 extends from the first surface 115 of the main body 110 to the second surface 117 of the main body 110. In this illustrated embodiment, the wall 122 attaches to a portion of each opening of the first set of openings 120 and to a portion of the first and second surrounding edges 119, 121. The wall 122 illustrated in this embodiment is considered advantageous at least because once the support member 150 is attached to the main body 110, the support member 150 can attach to the wall 122 along with the first surrounding edge 119, the second surrounding edge 121, and each opening of the first set of openings 120. In addition, the wall 122 prevents axial or rotational movement between the main body 110 and the support member 150 once the main body 110 and the support member 150 are attached together.

Figure 4:
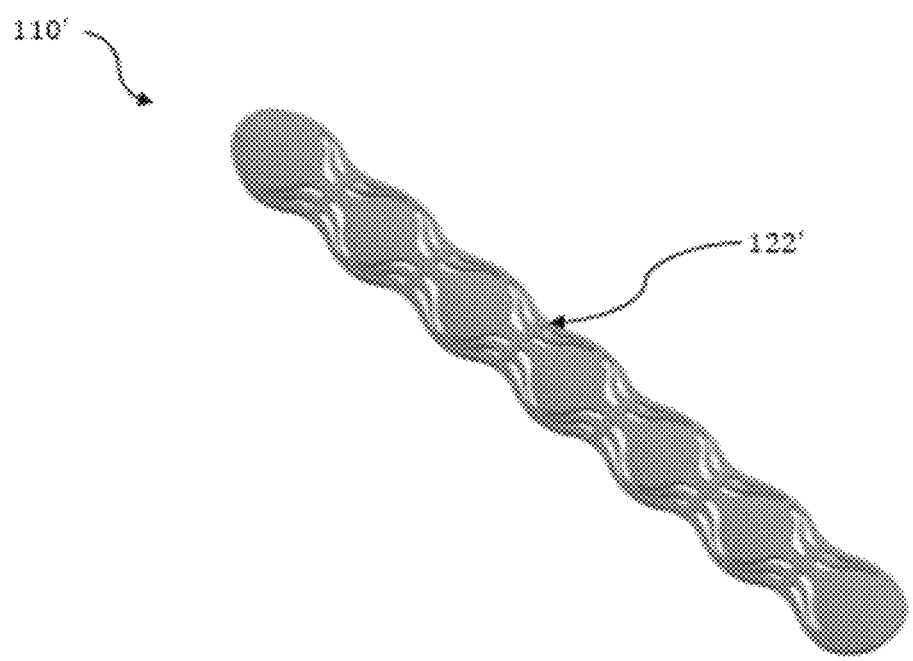
FIG. 4 illustrates a perspective view of an alternative main body of the example bone plate illustrated in FIG. 1.

The repetitive pattern of the wall 122 may have any suitable size, shape, and structural configuration, and a skilled artisan will be able to select an appropriate pattern configuration for a wall according to an embodiment based on various considerations, including the size, shape, and configuration of an support member. Examples of suitable pattern configurations include a crossover pattern, a zig-zag pattern, a spiral pattern, a sinusoidal pattern, a square pattern, a triangular pattern, or any other suitable structural pattern configurations for a particular application. As best illustrated in FIGS. 1 and 2, the wall 122 includes a crossover-like pattern. Alternatively, as best illustrated in FIG. 4, the wall 122' of the main body 100' includes a spiral-like pattern.

While the wall 122 extends between the main body first and second ends 112, 114, the wall 122 can extend along any suitable portion of a main body. A skilled artisan will be able to select a suitable position to dispose a wall on a main body according to a particular embodiment based on various considerations, including the type of support member that will be attached to a main body. Example positions considered suitable for a wall to be positioned along a main body include a position that extends between the main body first and second ends, a position between the main body first end and the medial portion of the main body, a position in the medial portion of the main body between the main body first and second ends, a position between the medial portion of the main body and the main body second end, and any other positions considered suitable for a particular application. In this illustrated embodiment, the wall 122 is positioned between the main body first and second ends 112, 114.

The wall 122 also defines a first set of lateral support members 124 and a second set of lateral support members 126. The first set of lateral support members 124 extends between each opening of the first set of openings 120 where each support member of the first set of lateral support members 124 is disposed parallel to the lengthwise axis 111 of the main body 110. Each support member of the first set of support member 124 attaches to a portion of each opening of the first set of openings 120 and to a portion of the first and second surrounding edges 119, 121 on the main body first and second ends 112, 114. Additionally, the second set of lateral support members 126 extends between the main body third and fourth ends 116, 118 where each support member of the second set of lateral support members 126 is disposed perpendicular to the lengthwise axis 111 of the main body 110. Each support member of the second set of lateral support members 126 attaches to a portion of the first and second surrounding edges 119, 121 on the main body third and fourth ends 116, 118.

The first and second sets of lateral support members 124, 126 illustrated in this embodiment are considered advantageous at least because each of first and second sets of lateral support members 124, 126 allows a support member 150 (described below) to form to itself during the manufacturing process of the bone plate 100. Furthermore, each of the first and second sets of lateral support members 124, 126 provides additional strength and retention between the main body 110 and the support member 150 in order to prevent axial or rotational movement between the main body 110 and the support member 150 once the bone plate 100 is placed and attached within a patient's body.

The first set of lateral support members 124 may have any suitable number of support members for a first set of lateral support members that extends between each opening of the first set of openings 120. A skilled artisan will be able to select an appropriate number of support members for a first set of lateral support members according to an embodiment based on various considerations, including the size, shape, and configuration of the main body. Examples of a suitable number of support members defined by a first set of lateral support members include, one, two, plurality, three, four, five, six, or any other suitable number of support members of a first set of lateral support members for a particular application. In the illustrated embodiment, the first set of lateral support members 124 includes one lateral support member that extends between each opening of the first set of openings 120.

Additionally, the second set of lateral support members 126 may have any suitable number of support members for a second set of lateral support members disposed between each opening of the first set of openings 120. A skilled artisan will be able to select an appropriate number of support members for a second set of lateral support members according to an embodiment based on various considerations, including the size, shape, and configuration of the main body. Examples of a suitable number of support members defined by a second set of lateral support members include, one, two, plurality, three, four, five, six, or any other suitable number of support members of a second set of lateral support members for a particular application. In the illustrated embodiment, the second set of lateral support members 126 includes two lateral support members that extend from the main body third and fourth ends 116, 118 and are disposed between each opening of the first set of openings 120.

The main body 110 may have any suitable size, shape, and structural configuration, and a skilled artisan will be able to select an appropriate configuration according to an embodiment based on various considerations, including the size and shape of a patient's bone, the size of the fracture in the patient's bone, and other considerations. Examples of suitable configurations for shaping the main body include a straight shape, curved shape, rounded shape, anatomically shaped, or any other suitable structural configurations for a particular application. As illustrated in FIGS. 2 and 3, the main body 110 is configured and shaped with a straight configuration. Alternatively, as illustrated in FIGS. 1 and 4, the main body 210 is configured and shaped with a curved plate configuration.

As illustrated in FIG. 1 the support member 150 has a support member first end 152, a support member second end 154, a lengthwise axis 153 that extends between the support member first end 152 and the support member second end 154, a third surface (not illustrated), and a fourth surface 155. As illustrated in the embodiment, the support member 150 is disposed about the main body 110 which extends between the main body first and second ends 112, 114 that defines a length 157. The support member first end 152 is positioned toward the main body first end 112, and the support member second end 154 is positioned toward the main body second end 114. In the illustrated embodiment, the third surface cooperatively engages the first and second surface 115, 117 of the main body 110, the wall 122, and the first and second surrounding edges 119, 121 once the support member 150 is formed about the main body 110 during the molding process, which is described in detail below. As such, the support member 150 is formed about and through the main body 110. The attachment formed during the molding process between the main body 110 and the support member 150 is considered advantageous at least because this attachment prevents axial or rotational movement between the main body 110 and the stopping member 150.

Furthermore, the fourth surface 155 may interface with a medical device, such as a screw, to attach the bone plate to a desired location during implantation, or the fourth surface may interface with a patient's bone to connect one or more of the patient's bones.

While the support member 150 is disposed over the entire main body 110 between from the main body first end 112 to the main body second end 114 with a length 157, the support member 150 can define any suitable length and dispose along any suitable portion, or the entirety, of a main body. A skilled artisan will be able to select a suitable position to attach the support member to a main body according to a particular embodiment based on various considerations, including the type of medical device with which the support member interfaces or attaches to during implantation. Example positions considered suitable for an support member to be positioned along a main body include a position between the main body first end and the medial portion of the main body, a position in the medial portion of the main body between the main body first and second ends, a position between the medial portion of the main body and the main body second end, a position that extends between the main body first and second ends, and any other positions considered suitable for a particular application. In this illustrated embodiment, the support member 150 extends between the main body first and second ends 112, 114 such that the support member 150 is attached about the entire main body 110.

Moreover, the main body 110 and the support member 150 can be made of different materials such that the main body 110 can be made of a first material and the support member 150 can be made from a second material, which is described in more detail below. For example, the main body 110 may be made of a thin metal material, such as titanium, and the support member 150 may be made of a polymer material, such as carbon fiber-polyetherketone material ("CF PEEK"). The combination of a first material and a second material for the main body 110 and the support member 150 of a bone plate 100 is considered advantageous at least because the bone plate 100 provides a user, such as surgeon, with improved visibility, while staying partially opaque, to adequately observe the site of a bone fracture in which the user can adequately position the bone plate 100 at a desired location. Moreover, the combination of the thin titanium and the CF PEEK materials provides the bone plate 100 with structural stability, due to the titanium, and radiolucency, due to the CF PEEK, without significantly increasing the overall plate thickness and allowing increased flexibility.

The main body 110 and the support member 150 can have any suitable attachment arrangement for attaching the support member 150 to the main body 110. A skilled artisan will be able to select suitable attachment arrangements for attaching a support member 150 to a main body 110. Example arrangements considered suitable include affixing the support member to the main body, attaching the support member to the main body, connecting the support member to the main body, locking the support member to the main body, fastening the support member to the main body, molding the support member to the main body, forming the support member to the main body, and any other attachment arrangement considered suitable for a particular application.

In the illustrated embodiment, the support member 150 is molded and formed to the main body 110 by using of injection molding, which is described in more detail below.

Figure 5:
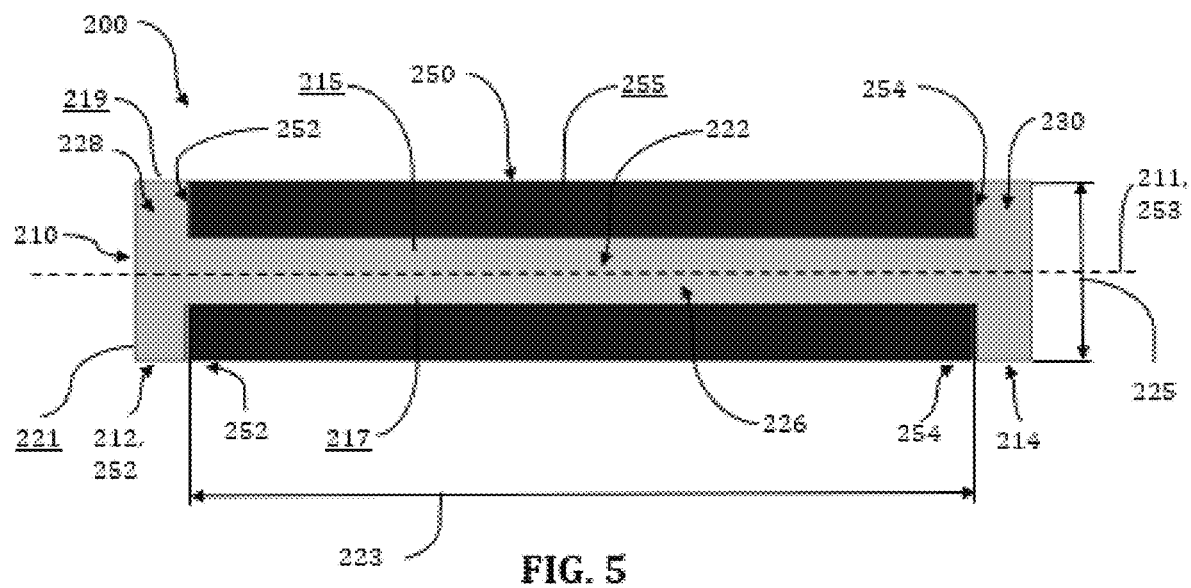
FIG. 5 illustrates a side view, partially broken away, of another example bone plate.
Figure 6:
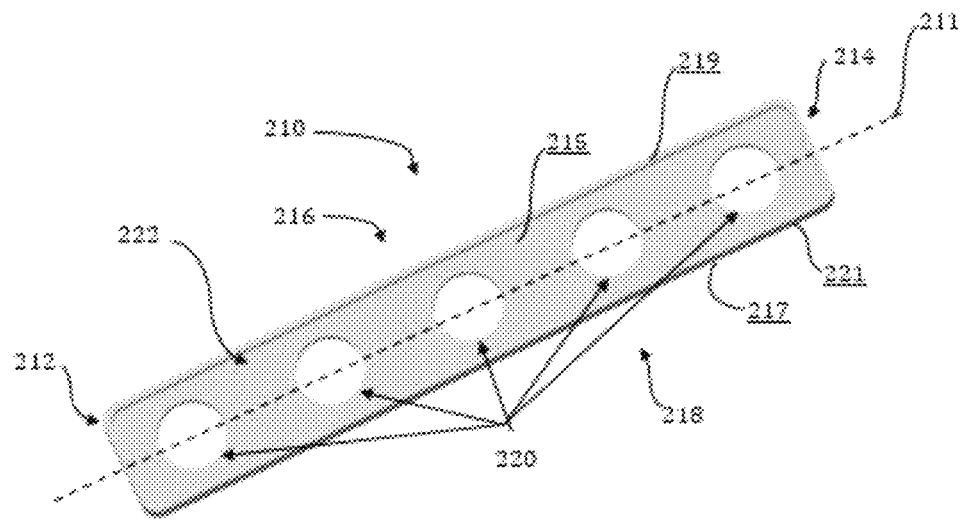
FIG. 6 illustrates a perspective view of the main body of the example bone plate illustrated in FIG. 5.

FIGS. 5 and 6 illustrate another example bone plate 200. The bone plate 200 is similar to the bone plate 100 described above, except as detailed below. The bone plate 200 includes a main body 210 and an support member 250.

As illustrated in FIG. 6, the main body 210 has a main body first end 212, a main body second end 214, a main body third end 216, a main body fourth end 218, a lengthwise axis 211 that extends between the main body first and second ends 212, 214, a first surface 215, a second surface 217, a first surrounding edge 219, a second surrounding edge 221, a first set of openings 220, a wall 222.

However, as best illustrated in FIG. 5, the wall 222 includes a first portion 226 and a second and third portions 228, 230. In this illustrated embodiment, the first, second, and third portions 226, 228, 230 are continuous. The first portion 226 extends between second and third portions 228, 230, the second portion 228 is disposed on the main body first end 212, and the third portion 230 is disposed on the main body second end 214. The first portion 226 defines a length 223 that is continuous between the second and third portions 228, 230 of the wall 222. Each of the second and third portions 228, 230 defines a length 225 that extends perpendicularly to the main body 210 relative to the lengthwise axis 211 of the main body 210. Furthermore, each of the first, second, and third portions 226, 228, 230 are disposed on each of the first and second surfaces 215, 217 of the main body 210. The first, second, and third portions 226, 228, 230 of the wall 222 are considered advantageous at least because once the support member 250 is introduced to the main body 210, each of the first, second, and third portions 226, 228, 230, of the wall 222 interfaces with the third surface of the support member 250 to prevent axial or rotational movement between the main body 210 and the support member 250, which is described in more detail below.

The support member 250 has a support member first end 252, a support member second end 254, a lengthwise axis 253 that extends between the support member first end 252 and the support member second end 254, a third surface (not illustrated), and a fourth surface 255. The support member first end 252 is positioned toward the main body first end 212, and the support member second end 254 is positioned toward the main body second end 214. As best illustrated in FIG. 5, the third surface cooperatively engages the first and second surface 215, 217 of the main body 210, the wall 222, and the first and second surrounding edges 219, 221. However, in this illustrated embodiment, the support member 250 is attached to each of the first and second surfaces 215, 217 and the first, second, and third portions 226, 228, 230 of the wall 222, but terminates at each of the first and second surrounding edges 219, 221. Indeed, the support member 250 does not attach about the first and second surrounding edges 219, 221. The attachment between the support member 250 and the main body 210 in this embodiment is considered advantageous at least because the attachment prevents any axial or rotational movement between the main body 210 and the support member 250.

Figure 7:
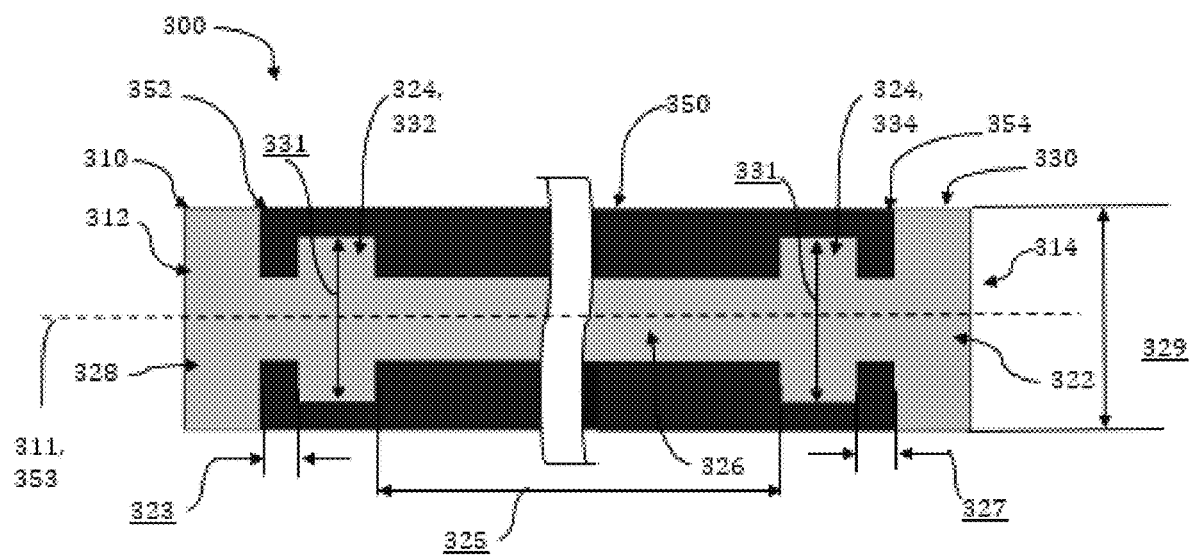
FIG. 7 illustrates a side view, partially broken away, of another example bone plate.
Figure 8:
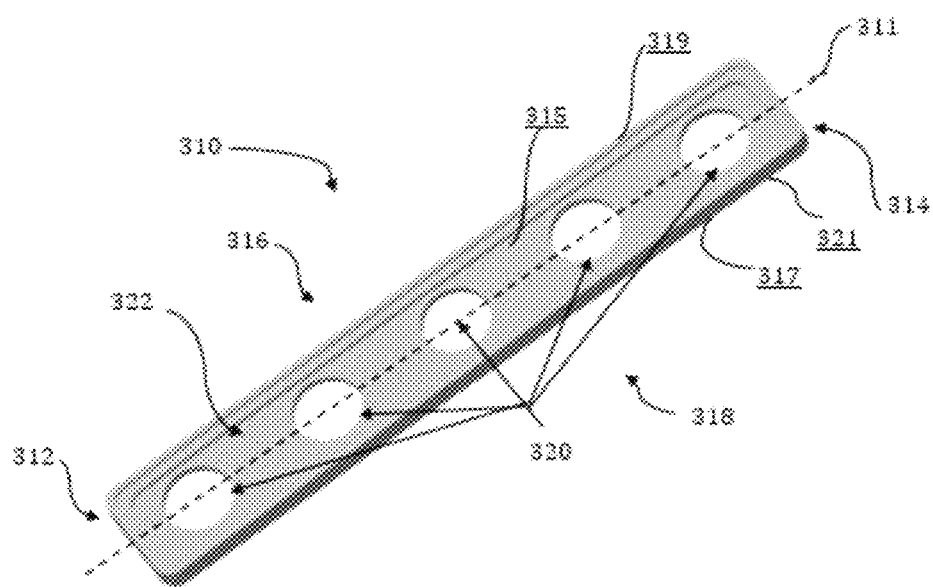
FIG. 8 illustrates a perspective view of the main body of the example bone plate illustrated in FIG. 7.

FIGS. 7 and 8 illustrate another example bone plate 300. The bone plate 300 is similar to the bone plates 100, 200 described above, except as detailed below. The bone plate 300 includes a main body 310 and a support member 350.

As illustrated in FIGS. 7 and 8, the main body 310 has a main body first end 312, a main body second end 314, a main body third end 316, a main body fourth end 318, a lengthwise axis 311 that extends between the main body first and second ends 312, 314, a first surface 315, a second surface 317, a first surrounding edge 319, a second surrounding edge 321, a first set of openings 320, a first wall 322, and a second wall 324.

As best illustrated in FIG. 8, the first wall 322 includes a first portion 326, a second portions 328, and a third portion 330. The first portion 326 is positioned between the second and third portions 328, 330, the second portion 328 is positioned at the main body first end 312, and the third portion 330 is positioned at the main body second end 314. The second wall 324 includes a fourth portion 332 and a fifth portion 334. The fourth portion 332 is positioned along the first portion 326 of the first wall 322 toward the main body first end 312, and the fifth portion 334 is positioned along the first portion 326 of the first wall 322 toward the main body second end 314. Furthermore, each of the first, second, third, fourth, and fifth portions 326, 328, 330, 332, 334 are disposed on each of the first and second surfaces 315, 317 of the main body 310.

As best illustrated in FIG. 7, the first portion 326 includes a first length 323, a second length 325, and a third length 327. The first length 323 is measured between the second portion 328 and the fourth portion 332, the second length 325 is measured between the fourth portion 332 and the fifth portion 334, and the third length 327 is measured between the fifth portion 334 and the third portion 330. Each of the second and third portions 328, 330 defines a fourth length 329 that is measured from the main body third end 316 to the main body fourth end 318 and extends perpendicularly to the main body 310 relative to the lengthwise axis 311 of the main body 310. Similarly, each of the fourth and fifth portions 332, 334 defines a fifth length 331 that is measured from the main body third end 316 to the main body fourth end 318 and extends perpendicularly to the main body 310 relative to the lengthwise axis 311 of the main body 310. In the illustrated embodiment, the second length 325 is greater than the first and third lengths 323, 327, and the fourth length 329 is greater than the fifth length 331.

The first, second, and third lengths 323, 325, 327 of the first portion 326 can have any suitable length for a first wall 322. A skilled artisan will be able to select suitable lengths for the first portion 326 of the wall 322 based on various considerations, such as the size of the support member and any other considerations. Examples lengths considered suitable include a first length greater than second and third lengths, a second length greater than first and third lengths, a third length greater than first and second lengths, each of the first, second, and third lengths have equal lengths, and any other lengths considered suitable for a particular purpose. In the illustrated embodiment, the second length 325 is greater than the first and third lengths 323, 327. Moreover, the fourth and fifth lengths 329, 331 of the second, third, fourth, and fifth portions 328, 330, 332, 334 can have any suitable length for either a first wall 322 or a second wall 324. A skilled artisan will be able to select suitable lengths for the second, third, fourth, and fifth portions 328, 330, 332, 334 of the first and second walls 322, 324 based on various considerations, such as the size of the support member and any other considerations. Examples lengths considered suitable include a fourth length greater than a fifth length, a fifth length greater than a fourth length, each of the fourth and fifth lengths have equal lengths, and any other lengths considered suitable for a particular purpose. In the illustrated embodiment, the fourth length 329 is greater than the fifth length 331.

The first, second, and third portions 326, 328, 330 of the first wall 322 and the fourth and fifth portions 332, 334 of the second wall 324 are considered advantageous at least because once the support member 350 is introduced to the main body 310, each of the first, second, third, fourth, and fifth portions 326, 328, 330, 332, 334 of the first and second walls 322, 324 interfaces with the third surface of the support member 350 to prevent axial or rotational movement between the main body 310 and the support member 350, which is described in more detail below.

The support member 350 has a support member first end 352, a support member second end 354, a lengthwise axis 353 that extends between the support member first end 352 and the support member second end 354, a third surface (not illustrated), and a fourth surface 355. The support member first end 352 is positioned toward the main body first end 312, and the support member second end 354 is positioned toward the main body second end 314. As best illustrated in FIG. 7, the third surface cooperatively engages each of the first and second surface 315, 317, each of the first, second, third, fourth, and fifth portions 326, 328, 330, 332, 334 of the first and second wall 322, 324, and the first and second surrounding edges 319, 321 once the support member 350 is formed about the main body 310 during the molding process. However, in this illustrated embodiment, the support member 350 terminates at each of the first and second surrounding edges 319, 321. Indeed, the support member 350 does not attach about the first and second surrounding edges 319, 321. The attachment between the support member 350 and the main body 310 in this embodiment is considered advantageous at least because the attachment between the support member 350 and each of the first, second, third, fourth, and fifth portions 326, 328, 330, 332, 334 of the first and second wall 322, 324 prevents axial or rotational movement between the main body 310 and the support member 350.

Figure 9:
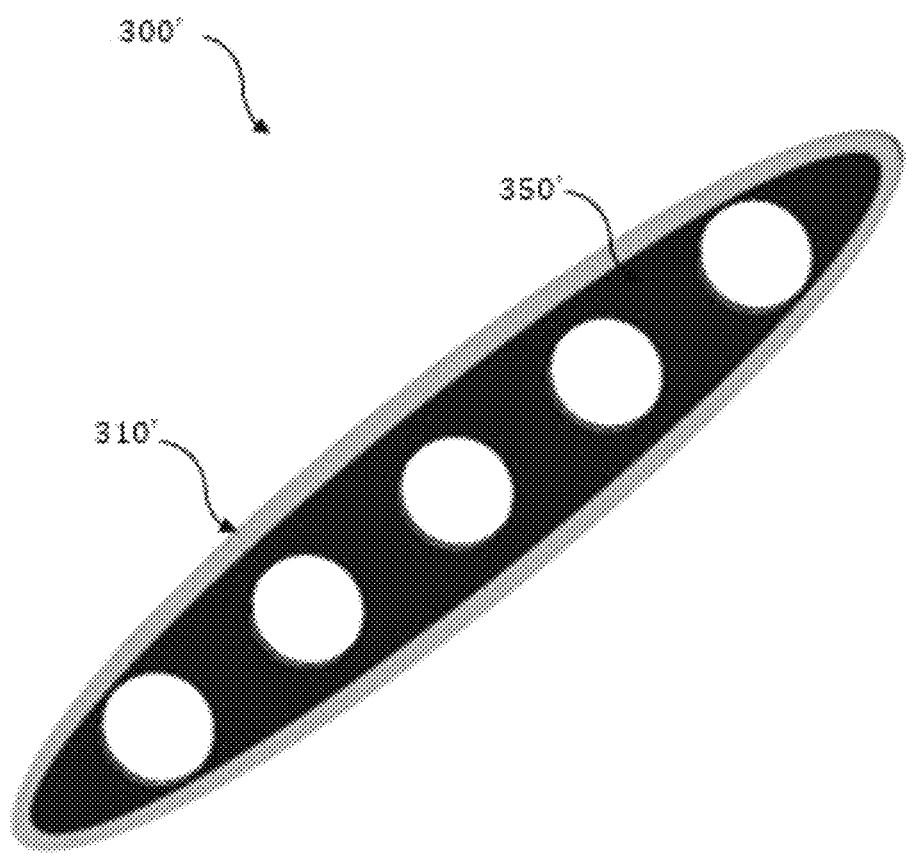
FIG. 9 illustrates a perspective view of an alternative bone plate of the example bone plate illustrated in FIG. 7.

The main body 310 may have any suitable size, shape, and structural configuration in which an support member 350 is formed onto the main body 310. A skilled artisan will be able to select an appropriate configuration for a main body according to an embodiment based on various considerations, including the size and shape of a patient's bone, the size of the fracture in the patient's bone, and other considerations. Examples of suitable configuration include circular, substantially circular, ovoidal, elliptical, rectangular, oblong rectangle, triangular, or any other suitable structural configuration for a particular application. In the illustrated embodiment, the main body 310 of the bone plate 300 defines a rectangular shape as shown in FIG. 8. Alternatively, the main body 310' and the support member 350' of the bone plate 300' can define an elliptical shape as shown in FIG. 9.

Figure 10:
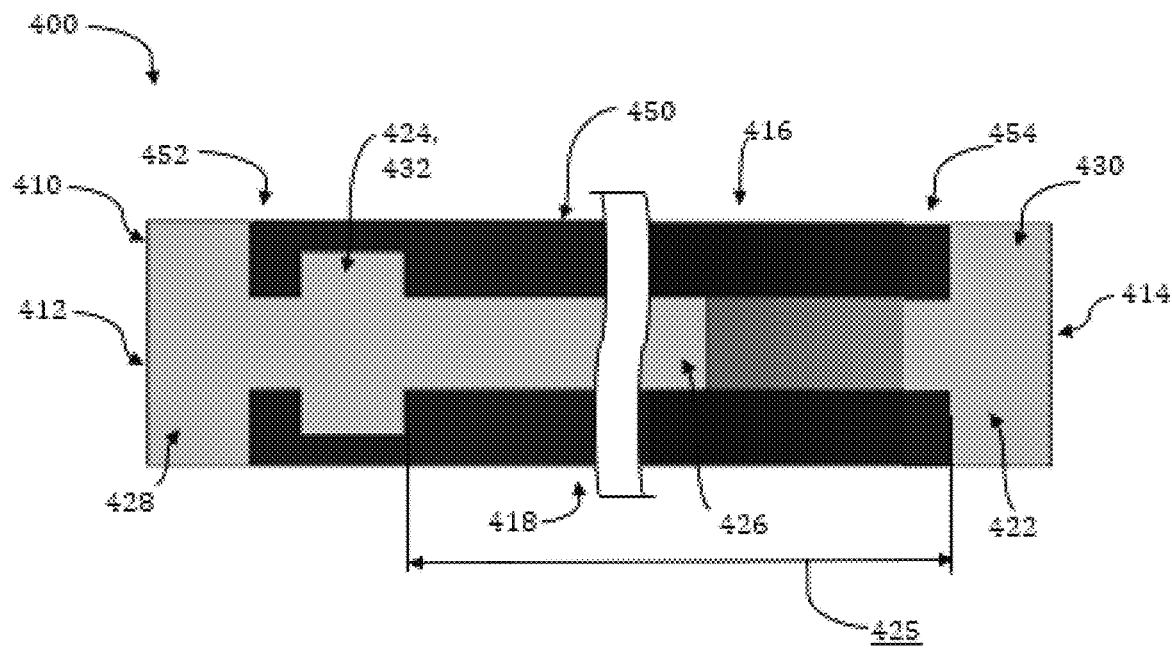
FIG. 10 illustrates a side view of another example bone plate.

FIG. 10 illustrates another example bone plate 400 that includes a support member 450 attached to a main body 410, and the main body 410 defines a first wall 422 and a second wall 424. The body plate 400 is similar to the bone plate 300 described above, except as detailed below. In this example, the first wall 422 defines a first portion 426, a second portion 428, and a third portion 430, but the second wall 422 only defines a fourth portion 432. As best illustrated in FIG. 10, the fourth portion 432 of the second wall 424 is positioned along each of the first and second surfaces 415, 417 toward the main body first end 412 to prevent axial or rotational movement between the main body 410 and support member 450 along a portion of each of the main body first end 412 and the support member first end 452. To prevent axial or rotational movement along a portion of each of the main body second end 412 and the support member second end 454, it would be advantageous to use an adhesive material, a mechanical friction configuration, or any other suitable structural configuration to have a portion of the support member second end 454 remain fixed to a portion toward the main body second end 414 during use. Furthermore, the second length 425 of the first portion 426 is greater than the second length 325 of the first portion 326 illustrated and described in FIGS. 7 through 9.

Figure 11:
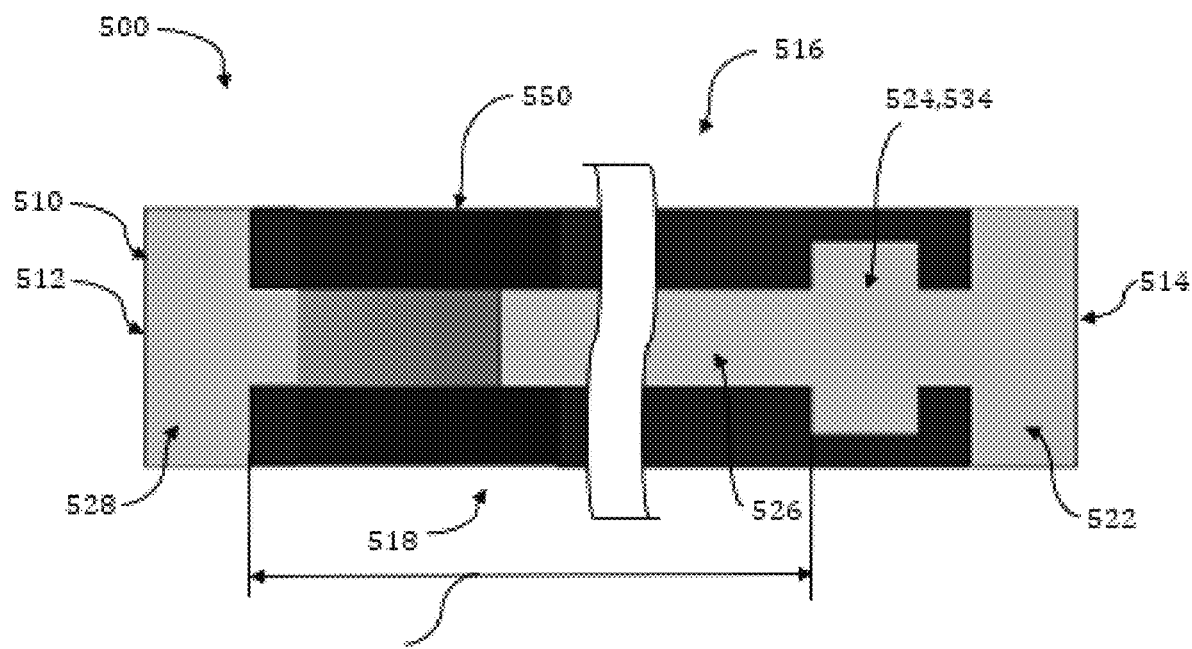
FIG. 11 illustrates a side view of another example bone plate.

FIG. 11 illustrates another example bone plate 500 that includes a support member 550 attached to a main body 510, and the main body 510 defines a first wall 522 and a second wall 524. The body plate 500 is similar to the bone plate 300 described above, except as detailed below. In this example, the first wall 522 defines a first portion 526, a second portion 528, and a third portion 530, but the second wall 522 only defines a fourth portion 534. As best illustrated in FIG. 11, the fourth portion 534 of the second wall 524 is positioned along the first and second surfaces 515, 517 toward the main body second end 514 to prevent axial or rotational movement between the main body 510 and support member 550 along a portion of each of the main body second end 514 and the support member second end 554. To prevent axial or rotational movement along a portion of each of the main body first end 512 and the support member first end 552, it would be advantageous to use an adhesive material, a mechanical friction configuration, or any other suitable structural configuration to have a portion of the support member first end 554 remain fixed to a portion toward the main body first end 512 during use. Furthermore, the second length 525 of the first portion 526 is greater than the second length 325 of the first portion 326 illustrated and described in FIGS. 7 through 9.

Figure 12:
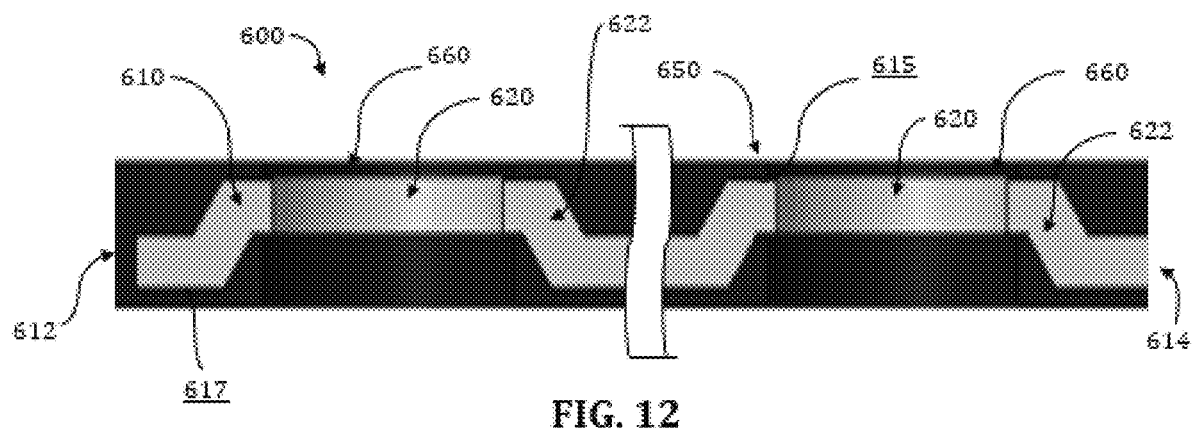
FIG. 12 illustrates a side view of another example bone plate.
Figure 13:
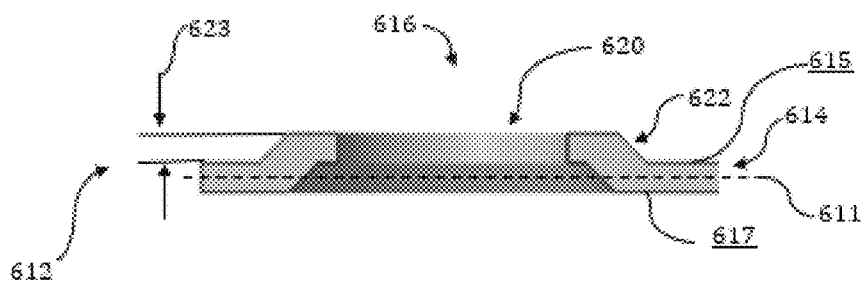
FIG. 13 illustrates a side view of the main body of the example bone plate illustrated in FIG. 12.
Figure 14:
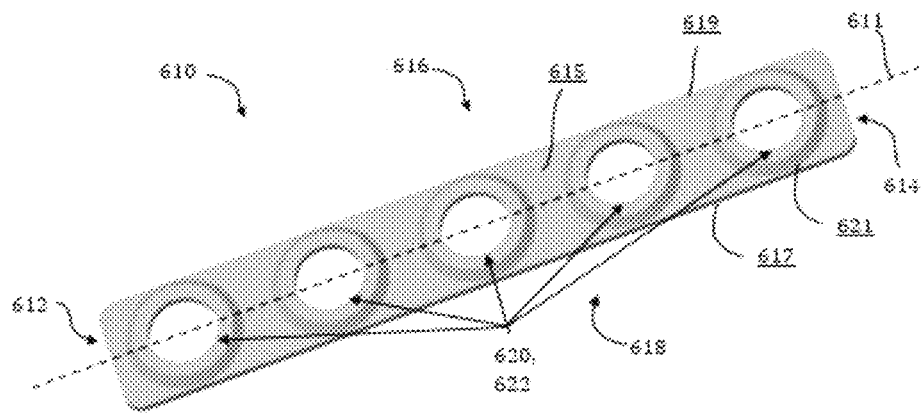
FIG. 14 illustrates a perspective view of the main body of the example bone plate illustrated in FIG. 12.

FIGS. 12, 13, and 14 illustrate another example bone plate 600. The bone plate 600 is similar to the bone plates 100 described above, except as detailed below. The bone plate 600 includes a main body 610 and a support member 650.

As illustrated in FIG. 14, the main body 610 has a main body first end 612, a main body second end 614, a main body third end 616, a main body fourth end 618, a lengthwise axis 611 that extends between the main body first and second ends 612, 614, a first surface 615, a second surface 617, a first surrounding edge 619, a second surrounding edge 621, a first set of openings 620, and a plurality of walls 622.

Each wall of the plurality of walls 622 is circumferentially positioned about each opening of the first set of openings 620. As best illustrated in FIG. 13, each wall of the plurality of walls 622 extends away perpendicularly from the main body 610 relative to the lengthwise axis 611. The plurality of walls 622 may be disposed on either the first or second surfaces 615, 617 of the main body 610. In the illustrated embodiment, the plurality of walls 622 is disposed on the first surface 615 of the main body 610. Additionally, each wall of the plurality of the walls 622 extends from the main body 610 at a length 623 that is measured from the first surface 615 to the main body third end 616. However, if the plurality of walls is disposed on the second surface 617, the length 623 of each wall of the plurality of the walls 622 is measured from the fourth surface 617 to the main body fourth end 618.

Moreover, as illustrated in FIG. 12, each wall of the plurality of walls 622 and each opening of the first set of openings 620 cooperatively interfaces with the third surface of the support member 650 to define a second set of openings 660 into the support member 650. The plurality of walls 622 is considered advantageous at least because the plurality of walls 622 and the first set of openings 620 provide additional support to prevent axial or rotational movement between the main body 610 and the support member 650 during use.

Each opening of the first set of openings 620 may have any suitable size, shape, and structural configuration, and a skilled artisan will be able to select an appropriate configuration for an opening according to an embodiment based on various considerations, including the size, shape, and configuration of a screw or a medical device that is to be received by each opening. Examples of suitable configuration include circular, substantially circular, ovoidal, elliptical, rectangular, triangular, or any other suitable structural configuration for a particular application. In the illustrated embodiment, each opening of the first set of openings 620 includes a circular shape. Additionally, the main body 610 may have any suitable number of openings for a first set of openings 620, and a skilled artisan will be able to select an appropriate number of openings according to an embodiment based on various considerations, including the size, shape, and configuration of a support member. Examples of a suitable number of openings disposed on a main body include one, two, plurality, three, four, five, six, or any other suitable number of openings of a first set of openings for a particular application. In the illustrated embodiment, the main body 610 includes five openings for the first set of openings 620.

Each wall of the plurality of walls 620 may have any suitable size, shape, and structural configuration, and a skilled artisan will be able to select an appropriate configuration for a wall according to an embodiment based on various considerations, including the size, shape, and configuration of a screw or a medical device that is receive by each opening. Examples of suitable configuration include circular, substantially circular, ovoidal, elliptical, rectangular, triangular, or any other suitable structural configuration for a particular application. In the illustrated embodiment, each wall of the plurality of walls 620 includes a circular shape. Additionally, the main body 610 may have any suitable number of walls for a plurality of walls 620, and a skilled artisan will be able to select an appropriate number of walls according to an embodiment based on various considerations, including the size, shape, and configuration of a support member. Examples of a suitable number of walls disposed on a main body include, one, two, plurality, three, four, five, six, or any other suitable number of openings of a first set of openings for a particular application. In the illustrated embodiment, the main body 610 includes five walls for the plurality of walls 620.

Figure 15:
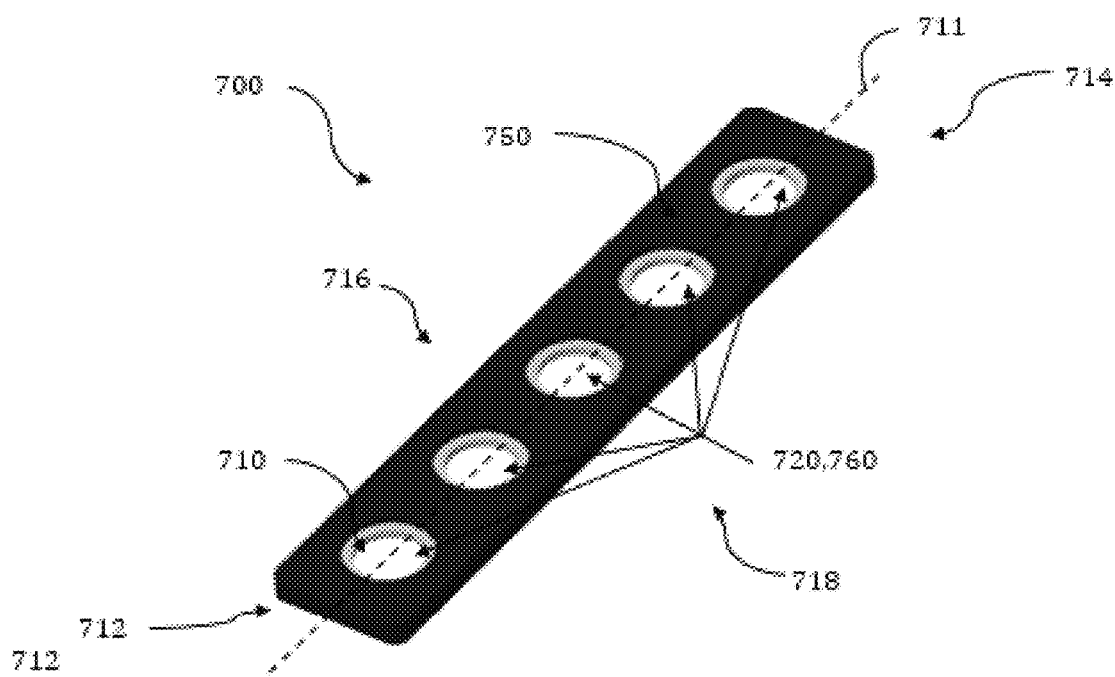
FIG. 15 illustrates a perspective view of another example bone plate.
Figure 16:
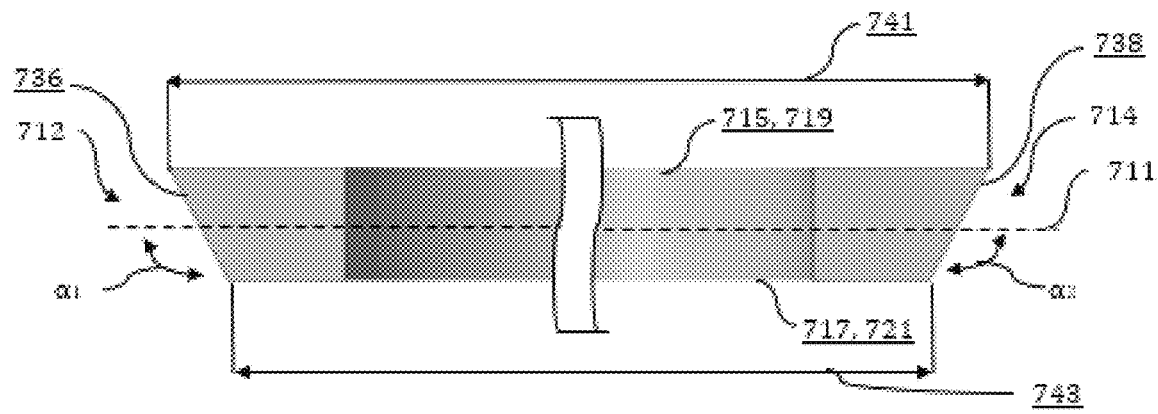
FIG. 16 illustrates a side view of the main body of the example bone plate illustrated in FIG. 15.
Figure 17:
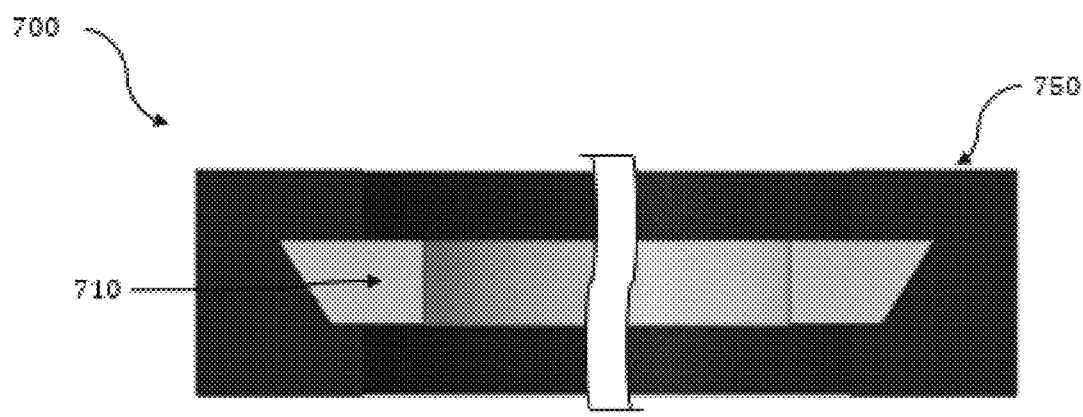
FIG. 17 illustrates a side view of the example bone plate illustrated in FIG. 15.

FIGS. 15, 16, and 17 illustrate another example bone plate 700. The bone plate 700 is similar to the bone plates 100 described above, except as detailed below. The bone plate 700 includes a main body 710 and a support member 750.

As illustrated in FIGS. 15 and 16, the main body 710 has a main body first end 712, a main body second end 714, a main body third end 716, a main body fourth end 718, a lengthwise axis 711 that extends between the main body first and second ends 712, 714, a first surface 715, a second surface 717, a first surrounding edge 719, a second surrounding edge 721, a first set of openings 720, and a wall 722.

The wall 722 extends between the main body first and second ends 712, 714. As best illustrated in FIG. 16, at each end of the wall 722, the wall 722 defines a first angled surface 736 and a second angled surface 738 measured at first and second angles co, co. The first angled surface 736 is positioned at the main body first end 712, and the first angle co of the first angled surface 736 is measured relative to the lengthwise axis 711 of the main body 710. Similarly, the second angled surface 738 is positioned at the main body second end 714, and the second angle $\alpha_2$ is measured relative to the lengthwise axis 711 of the main body 710. In this illustrated embodiment, the first and second angles $\alpha_1$, $\alpha_2$ of the first and second angled surfaces 736, 738 are congruent angles and directly oppose each other. The first and second angles surfaces 736, 738 of the wall 722 are considered advantageous at least because each of the first and second angles $\alpha_1$, $\alpha_2$ prevents axial or rotational movement between the main body 710 and the support member 750 during use. Furthermore, as illustrated in FIG. 16, the first surface 715 has a first surface length 741, and the second surface 717 has a second surface length 743. In the illustrated embodiment, the first surface length 741 is greater than the second surface length 743.

The first and second angles $\alpha_1$, $\alpha_2$ of the wall 722 may have any suitable angle, and a skilled artisan will be able to select an appropriate angle for first and second angles of a wall according to an embodiment based on various considerations, including the size, shape, and configuration of a support member. Examples of suitable angles for first and second angles of a wall include a first angle greater than a second angle, a second angle greater than a first angle, each of the first and second angles are equal, each of the first and second angles are congruent, and any other suitable angle arrangements for a particular purpose. In the illustrated embodiment, the first and second angles $\alpha_1$, $\alpha_2$ of the wall 722 are congruent angles.

Figure 18:
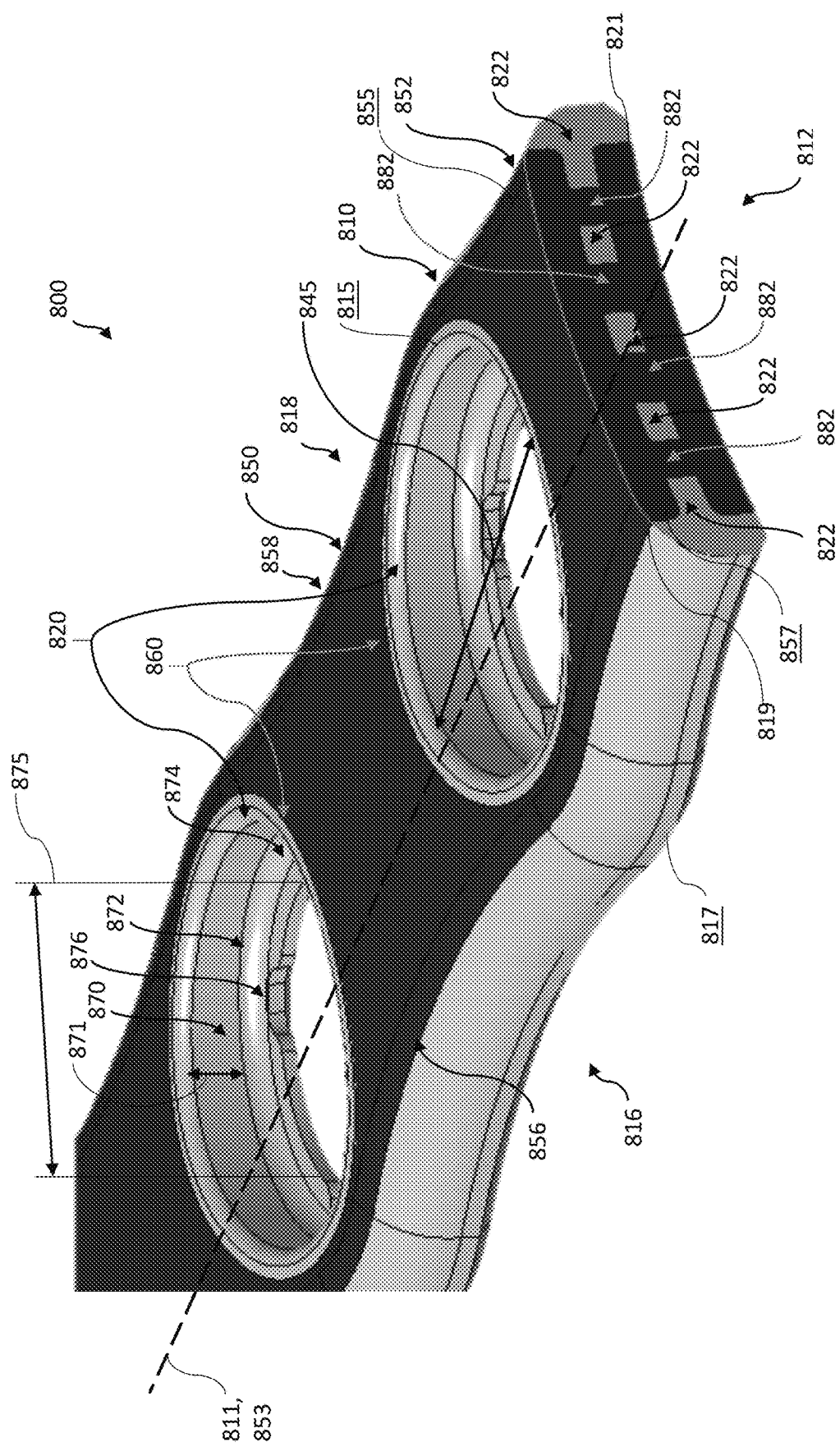
FIG. 18 illustrates a perspective view, partially broken away, of another example bone plate.
Figure 18A:
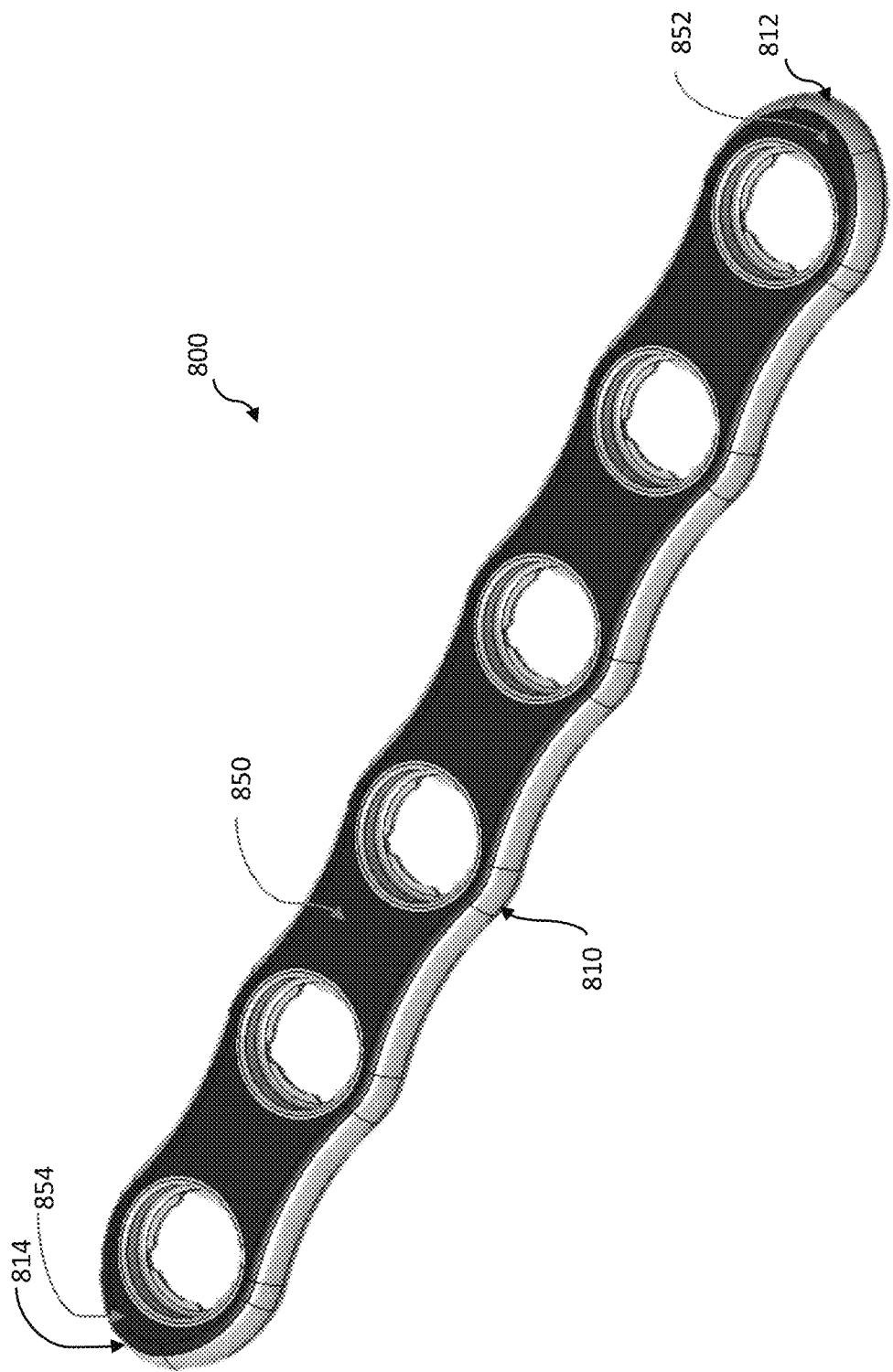
FIG. 18A illustrates a perspective view of the example bone plate illustrated in FIG. 18
Figure 18B:
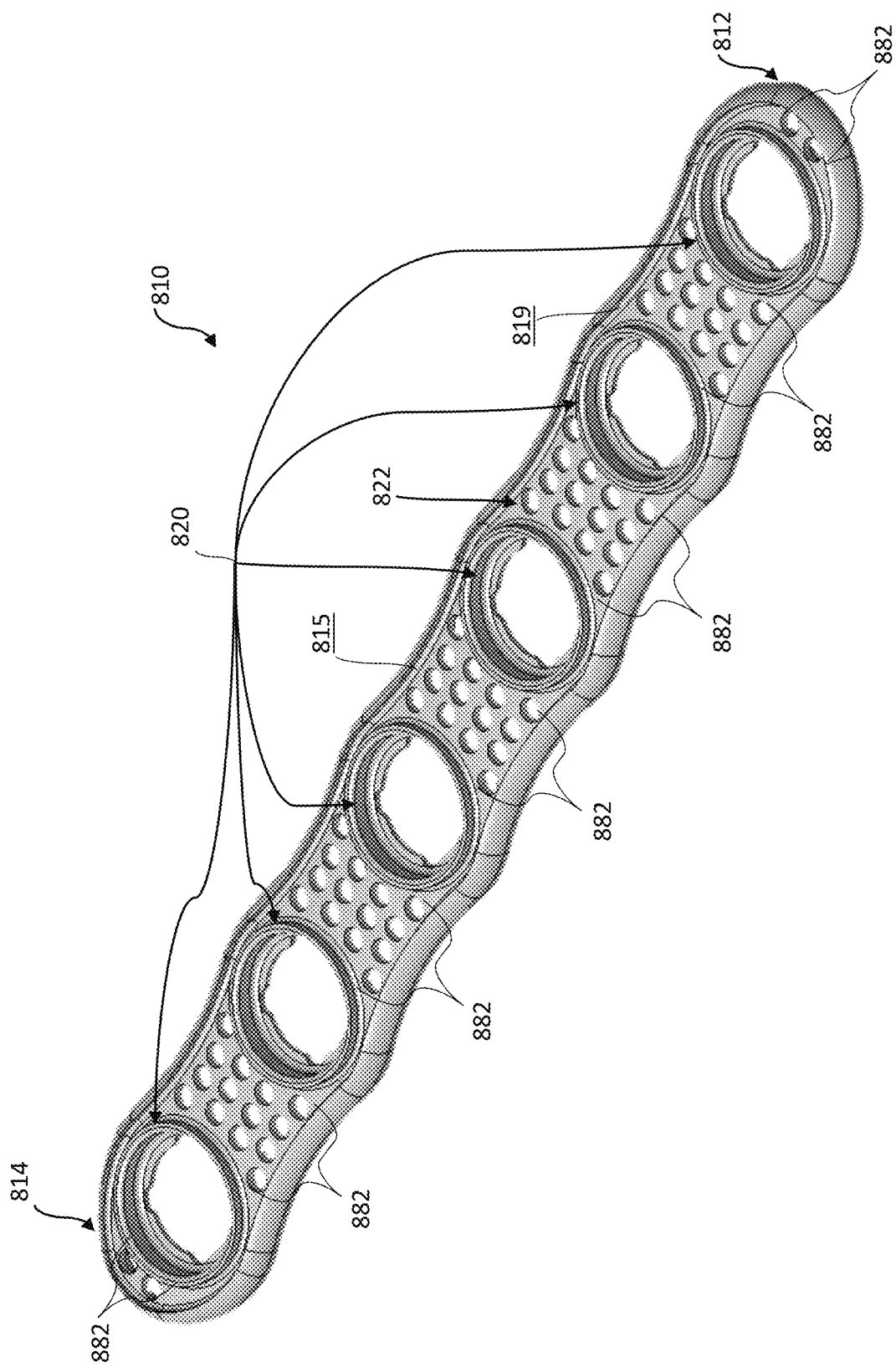
FIG. 18B illustrates a perspective view of the main body of the example bone plate illustrated in FIG. 18.

FIGS. 18, 18A, and 18B illustrate another example bone plate 800.

The bone plate 800 is similar to the bone plate 100 described above, except as detailed below. The bone plate 800 includes a main body 810 and a support member 850.

In the illustrated embodiment, the main body 810 has a main body first end 812, a main body second end 814, a main body third end 816, a main body fourth end 818, a lengthwise axis 811 that extends between the main body first end 812 and the main body second end 814, a first surface 815, a second surface 817, a first surrounding edge 819, a second surrounding edge 821, a first set of openings 820, and a wall 822.

As illustrated in FIG. 18, each opening of the first set of openings 820 defines a recess 870 that extends from the first surface 815 into the main body 810 at a recess length 871. Each recess 870 of each opening of the first set of openings 820 terminates at a recess base 872 that is disposed between the first and second surfaces 815, 817 of the main body 810. Each opening of the first set of openings 820 also defines a locking member 874. In this embodiment, each locking member 874 is disposed circumferentially about each recess base 872. Each locking member 874 also defines a locking member diameter 875 that extends between the main body third end 816 and the main body fourth end 818. In the illustrated embodiment, the locking member diameter 875 is less than each opening diameter 845 of the first set of openings 820. In addition, each locking member 874 also defines a plurality of notches 876 that extends into the locking member 874. The plurality of notches 876 defined by each locking member 874 is considered advantageous at least because the plurality of notches 876 provides a structural interface that allows a locking screw (not illustrated) or a suitable medical device to be inserted through an opening of the first set of openings 820 and to be secured to the bone plate 800 once the locking screw or medical device has been inserted into a desired location of a patient's bone.

Each locking member 874 may have any suitable size, shape, and structural configuration, and a skilled artisan will be able to select an appropriate configuration for a locking member according to an embodiment based on various considerations, including the size, shape, and configuration of a locking screw or a medical device that is to be received by each locking member. Examples of suitable shapes for a locking member include circular, substantially circular, ovoidal, elliptical, rectangular, triangular, or any other suitable structural configuration for a particular application. In the illustrated embodiment, each locking member 874 includes a circular shape. Additionally, the plurality of notches 876 of each locking member 874 may have any suitable number of notches for a plurality of notches, and a skilled artisan will be able to select an appropriate number of notches according to an embodiment based on various considerations, including the configuration of a locking screw or a medical device that is to be received by a plurality of notches of a locking member. Examples of a suitable number of notches defined by a locking member include, one, two, plurality, three, four, five, six, or any other suitable number of notches of a locking member 874 for a particular application. In the illustrated embodiment, the plurality of notches 876 of a locking member 874 includes at least two notches 876 for each locking member 874.

In the illustrated embodiment, the wall 822 extends between the main body first end 812 and the main body second end 814. The wall 822 lies on a plane that is parallel to the main body 810 relative to the lengthwise axis 811 of the main body 810. As illustrated in FIGS. 18 and 18B, the wall 822 defines a plurality of passageways 882 that extends entirely through main body 810 such that each passageway of the plurality of passageways 882 extends from the first surface 815 of the main body 810 to the second surface 817 of the main body 810. Each passageway of the plurality of passageways 882 provides fluid communication between the first surface 815 of the main body 810 and the second surface 817 of the main body 810. In the illustrated embodiment, each passageway of the plurality of passageways 882 is also disposed on a plane that is perpendicular to the lengthwise axis 811 of the main body 810. Alternatively, each passageway of the plurality of passageways 882 may also be disposed at an angle relative to the lengthwise axis 811 of the main body 810. In this illustrated embodiment, the wall 822 attaches to a portion of each opening of the first set of openings 820 and to a portion of the first and second surrounding edges 819, 821. The wall 822 illustrated in this embodiment is considered advantageous at least because once the support member 850 is attached to the main body 810, the support member 850 can attach to the wall 822 along with the first surrounding edge 819, the second surrounding edge 821, each opening of the first set of openings 820, and within each passageway of the plurality of passageways 882. In addition, the wall 822 prevents axial or rotational movement between the main body 810 and the support member 850 once the main body 810 and the support member 850 are attached together.

Furthermore, the plurality of passageways 882 allows the support member 850 to attached to itself to provide additional strength and retention between the main body 810 and the support member 850 during use.

The main body 810 may have any suitable size, shape, and structural configuration, and a skilled artisan will be able to select an appropriate configuration according to an embodiment based on various considerations, including the size and shape of a patient's bone, the size of the fracture in the patient's bone, and other considerations. Examples of suitable configurations for shaping the main body include a straight shape, curved shape, rounded shape, anatomically shaped, T-shaped, X-shaped, S-shaped, L-shaped, box-shaped or any other suitable structural configurations for a particular application. As illustrated in FIG. 18, the main body 810 is configured and shaped with a curved configuration around the first set of openings 820.

The support member 850 has a support member first end 852, a support member second end 854, a lengthwise axis 853 that extends between the support member first end 852 and the support member second end 854, a third surface 857, a fourth surface 855, and a second set of openings 860.

In the illustrated embodiment, the support member 850 is disposed on the first and second surfaces 815, 817 of the main body 810 and within the main body 810. This interaction between the support member 850 and the first and second surfaces 815, 817 occurs without the support member 850 being circumferentially disposed about the main body 810 because of the plurality of passageways 882 providing communication between the first and second surface 815, 817 of the main body 810. As such, the third surface 857 of the support member 850 cooperatively engages the first and second surface 815, 817, the wall 822, the first and second surrounding edges 819, 821, and the plurality of passageways 882 once the support member 850 is formed on to the main body 810 during the molding process, which is described in detail below. Therefore, the support member 850 is formed within and through the main body 810, which is different from the support member 150 described in bone plate 100 and illustrated in FIG. 1 The attachment between the support member 850 and the main body 810 is considered advantageous at least because the attachment prevents axial or rotational movement between the main body 810 and the support member 850 while the bone plate 800 is attached to a patient's bone. Additionally, the combination of the main body 810 and the support member 850 is considered advantageous at least because this combination provides a user, such as a surgeon, with sufficient observation of the bone fracture since the bone plate remains partially opaque to assist the user in locating both the bone plate and the bone fracture simultaneously. Furthermore, the fourth surface 855 may interface with a medical device, such as a screw or plate, to attach the bone plate to a desired location during implantation, or the fourth surface may interface with a patient's bone to connect one or more of the patient's bones.

Figure 19:
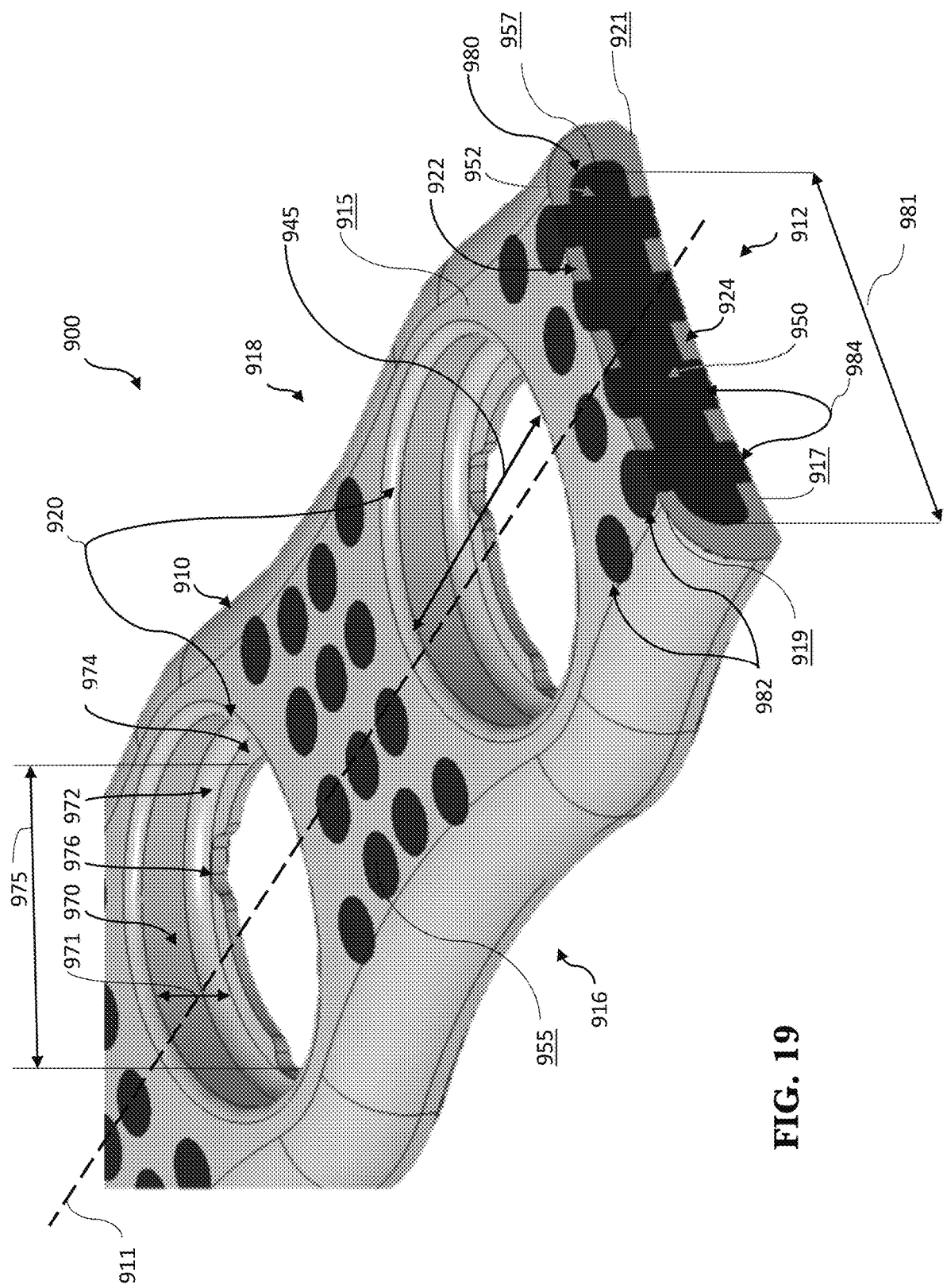
FIG. 19 illustrates a perspective view, partially broken away, of another example bone plate.
Figure 19A:
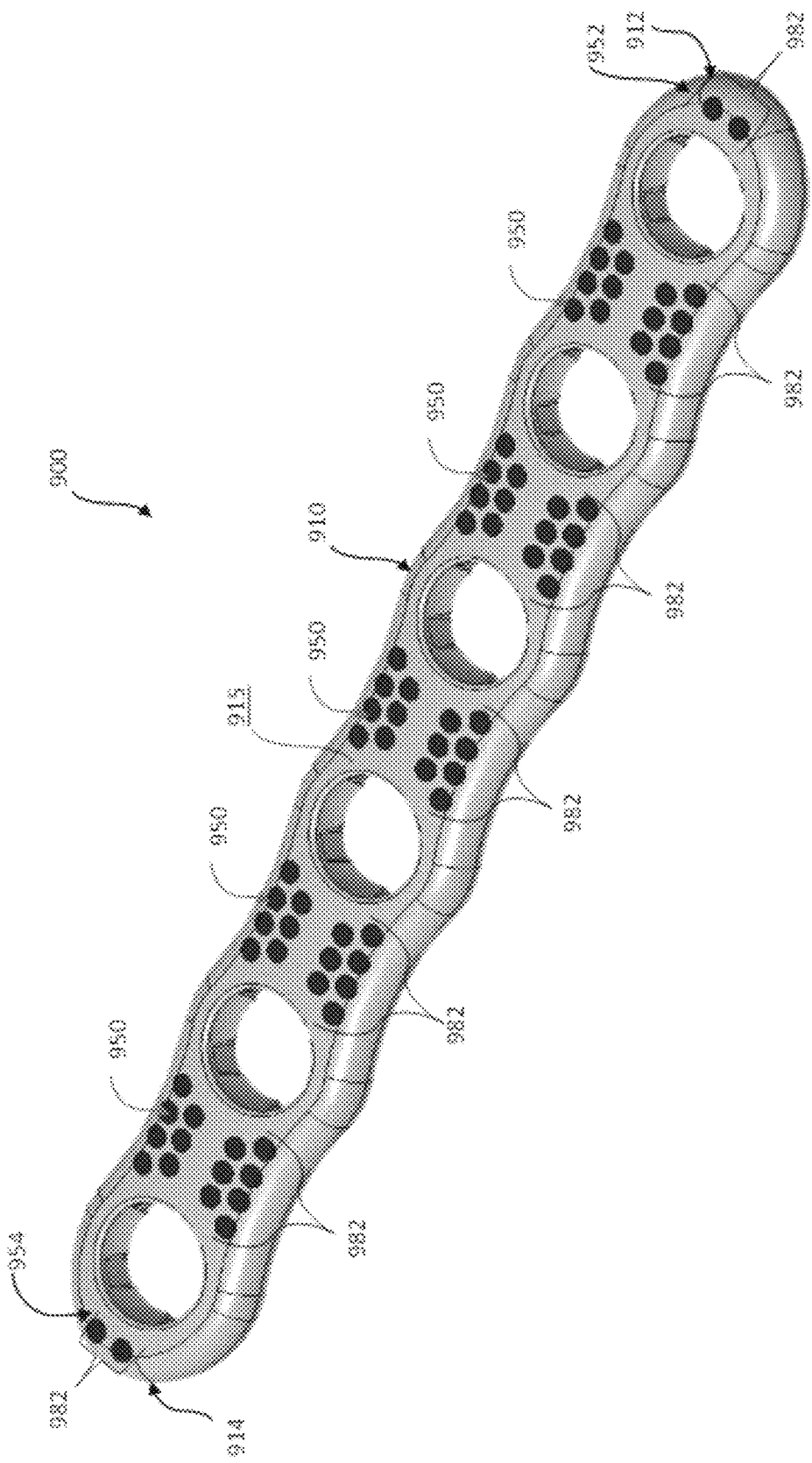
FIG. 19A illustrates a perspective view of the example bone plate illustrated in FIG. 19.

FIGS. 19 and 19A illustrates another example bone plate 900. The bone plate 900 is similar to the bone plate 800 described above, except as detailed below. The bone plate 900 includes a main body 910 and a support member 950.

In the illustrated embodiment, the main body 910 has a main body first end 912, a main body second end 914, a main body third end 916, a main body fourth end 918, a lengthwise axis 911 that extends between the main body first end 912 and the main body second end, a first surface 915, a second surface 917, a first surrounding edge 919, a second surrounding edge 921, a set of openings 920, a first wall 922, and a second wall 924. In addition, each opening of the set of openings 920 defines a recess 970 that extends to a recess base 972, and each opening of the set of openings 920 includes a locking member 974 that defines a plurality of notches 976 similar to the bone plate 800 illustrated in FIG. 18.

The first and second walls 922, 924 extend between the main body first end 912 and the main body second end. The first wall 922 is disposed on a plane that is parallel to the lengthwise axis 911 of the main body 910. Similarly, the second wall 924 is also disposed on a plane that is parallel to the lengthwise axis 911 of the main body 910. However, in this embodiment, each of the first and second walls 922, 924 directly oppose each other. Furthermore, each of the first and second walls 922, 924 are continuous with each other such between the main body third and fourth ends 916, 918. Alternatively, each of the first and second walls 922, 924 may be separate from each other.

Each of the first and second walls 922, 924 defines a chamber 980, the first wall 922 defines a first set of passageways 982, and the second wall 924 defines a second set of passageways 984. The chamber 980 is disposed between each of the first and second sets of passageways 982, 984. The chamber 980 also extends between each opening of the set of openings 920 along on a plane that is parallel to the lengthwise axis 911 of the main body 910. Alternatively, the chamber 980 may also extend between and around each opening of the set of openings 920 such that the chamber 980 extends continuously through the main body 910 from the main body first end 912 to the main body second end. In addition, the chamber 980 defines a chamber diameter 981 that is measured between the main body third and fourth ends 916, 918. The chamber 980, the first set of passageways 982, and the second set of passageways 984 are in communication with each other. The first set of passageways 982 provides access to the chamber 980 such that each passageway of the first set of passageways 982 extends from the first surface 915, through the first wall 922, and into the chamber 980. Similarly, the second set of passageways 984 also provides access to the chamber 980 such that each passageway of the second set of passageways 984 extends from the second surface 917, through the second wall 924, and into the chamber 980. Additionally, each passageway of the first and second sets of passageways 982, 984 is coaxial with each other on an axis that is perpendicular to the lengthwise axis 911 of the main body 910. Alternatively, each passageway of the first and second sets of passageways 982, 984 may be disposed on a different axis such that each passageway of the first set of passageways 982 is aligned on a first axis relative to the lengthwise axis 911 of the main body 910 and each passageway of the second set of passageways 984 is aligned on a second axis relative to the lengthwise axis 911 of the main body 910. Furthermore, each passageway of the first and second set of passageways 982, 984 may be positioned at a predetermined distance that is measured between each passageway of the first and second sets of passageways 982, 984. The distance between each passageway of either the first or second set of passageways 982, 984 can be determined based on various considerations, including the shape, size, and configuration of the first set of openings 920, any locking screws or medical devices, and the bone plate 900.

The communication between the chamber 980, the first set of passageways 982, and second set of passageways 984 is considered advantageous at least because a support member 950 can be injected into either the first set of passageways 982 or the second set of passageways 984 as a precursor material that forms into the support member 950 during the injection molding process of the bone plate 900, as described in detail below. Additionally, the support member 950 can also be injected into both the first set of passageways 982 and the second set of passageways 984 as a precursor material that forms into the support member 950 during the injection molding process of the bone plate 900, as described in detail below. Furthermore, the structural arrangement of the first and second walls 922, 924 is considered advantageous at least because each of the first and second walls 922, 924 provides additional strength and retention between the main body 910 and the support member 950 to prevent axial or rotational movement between the main body 910 and the support member 950 once the bone plate 900 is placed and attached to a patient's bone.

The first set of passageways 982 may have any suitable number of passageways for a first set of passageways 982 between each opening of the set of openings 920. A skilled artisan will be able to select an appropriate number of passageways for a first set of passageways according to an embodiment based on various considerations, including the size, shape, and configuration of the main body. Examples of a suitable number of passageways defined by a first set of passageways include one, two, plurality, three, four, five, six, seven, eight, nine, ten, eleven, twelve, thirteen, fourteen, or any other suitable number of passageways of a first set of passageways for a particular application. In the illustrated embodiment, the first set of passageways 982 includes fourteen passageways positioned between each opening of the set of openings 920.

The second set of passageways 984 may have any suitable number of passageways for a second set of passageways 984 between each opening of the set of openings 920. A skilled artisan will be able to select an appropriate number of passageways for a second set of passageways according to an embodiment based on various considerations, including the size, shape, and configuration of the main body. Examples of a suitable number of passageways defined by a second set of passageways include one, two, plurality, three, four, five, six, seven, eight, nine, ten, eleven, twelve, thirteen, fourteen, or any other suitable number of passageways of a second set of passageways for a particular application. In the illustrated embodiment, the second set of passageways 984 includes fourteen passageways positioned between each opening of the set of openings 920.

In an alternative embodiment, the first wall 922 or the second wall 924 of the main body 910 may omit either the first set of passageways 982 or the second set of passageways 984 for an alternative main body 910. An example of an alternative main body 910' may include a first wall 922' and a second wall 924' that defines a chamber 980', the first wall 922' includes a first set of passageways 982', and the second wall 924' omits the second set of passageways 984. Another example of an alternative main body 910" may include a first wall 922" and a second wall 924" that defines a chamber 980", the second wall 924" includes a second set of passageways 984", and the first wall 922" omits the first set of passageways 982.

In the illustrated embodiment, the support member 950 is formed inside of the main body 910 through an injection molding process as compared to other support members and molding processes described herein. Initially, the support member 950 starts as a precursor material that can be injected into the first set of passageways 982 and/or the second set of passageways 984 of the main body 910. Once the precursor material is injected into the first set of passageways 982 and/or the second set of passageways 984, the precursor material is introduced into the chamber 980 of the main body 910. The injection process of the precursor material continues into the chamber 980 until the precursor material is completely disposed within the chamber 980, each passageway of the first set of passageways 982, and each passageway of the second set of passageways 984. Once the injection molding process is complete, the precursor material forms into the support member 950 and is disposed inside of the main body 910 as shown in FIG. 19.

The precursor material that forms the support member 950 may be any suitable precursor material. A skilled artisan will be able to select an appropriate precursor material for a support member according to an embodiment based on various considerations. Examples of a suitable precursor material for a support member include carbon fiber, polyaryletherketone (PAEK), polyether ether ketone (PEEK), PEEK (90G, 450G, I2, I4), Polyamid, PA66, carbon fiber reinforced polyaryletherketone (CFR PAEK), polyethere ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, 12 CF20, 12 CF30, 14 CF30, 14 CF20), Polyamid CFR, PA66 CFR, and any other suitable precursor materials that forms a support member for a particular application.

After being formed within the main body 910, the support member 950 includes a support member first end 952, a support member second end 954, a third surface 957, and a fourth surface 955. The support member 950 is disposed between the first and second surfaces 915, 917 of the main body 910 and within the main body 910. Once formed, the third surface 957 of the support member 950 cooperatively engages the first and second walls 822, the chamber 980, each passageway of the first set of passageways 982, and each passageway of the second set of passageways 984. The attachment formed during the injection molding process between the main body 910 and the support member 950 is considered advantageous at least because this attachment prevents axial or rotational movement between the main body 910 and the stopping member 950 once the bone plate 900 is attached to a patient's bone. Furthermore, the fourth surface 955 of the support member 950 is even with each of the first and second surfaces 915, 917 of the main body 910. The fourth surfaces 955 may also interface with a medical device to attach the bone plate to a desired location during implantation, or the fourth surface may interface with a patient's bone to connect one or more of the patient's bones.

The attachment between the support member 950 and the main body 910 is considered advantageous at least because the attachment prevents axial or rotational movement between the main body 910 and the support member 950 while the bone plate 900 is attached to a patient's bone. Additionally, the combination of the main body 910 and the support member 950 is considered advantageous at least because this combination provides a user, such as a surgeon, with sufficient observation of the bone fracture since the bone plate remains partially opaque to assist the user in locating both the bone plate and the bone fracture simultaneously FIGS. 20, 20A, 21, and 21A illustrate another example bone plate 1000. The bone plate 1000 is similar to the bone plate 800 described above, except as detailed below. The bone plate 1000 includes a main body 1010 and a support member 1050.

Figure 20:
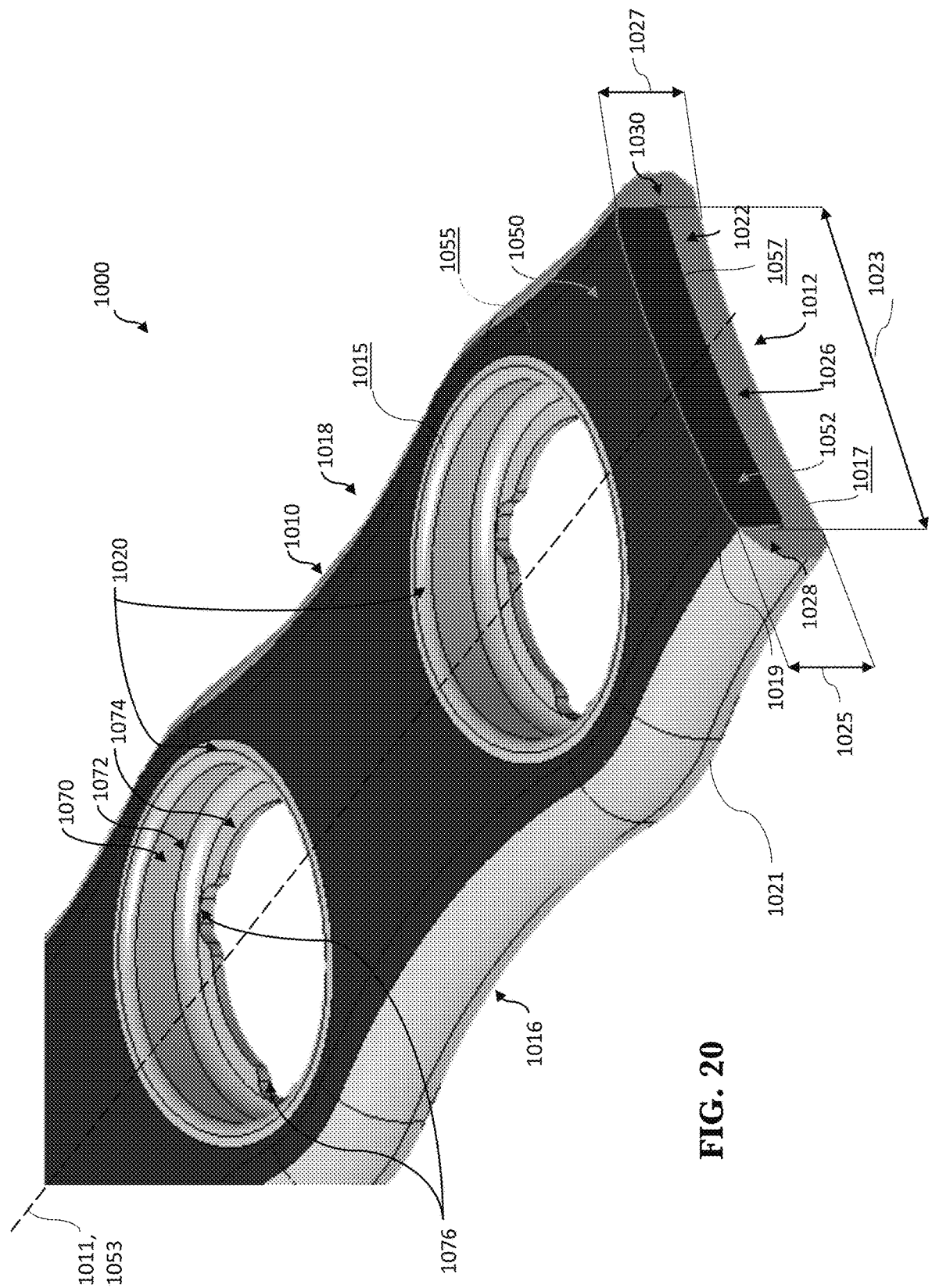
FIG. 20 illustrates a perspective view, partially broken away, of another example bone plate.
Figure 20A:
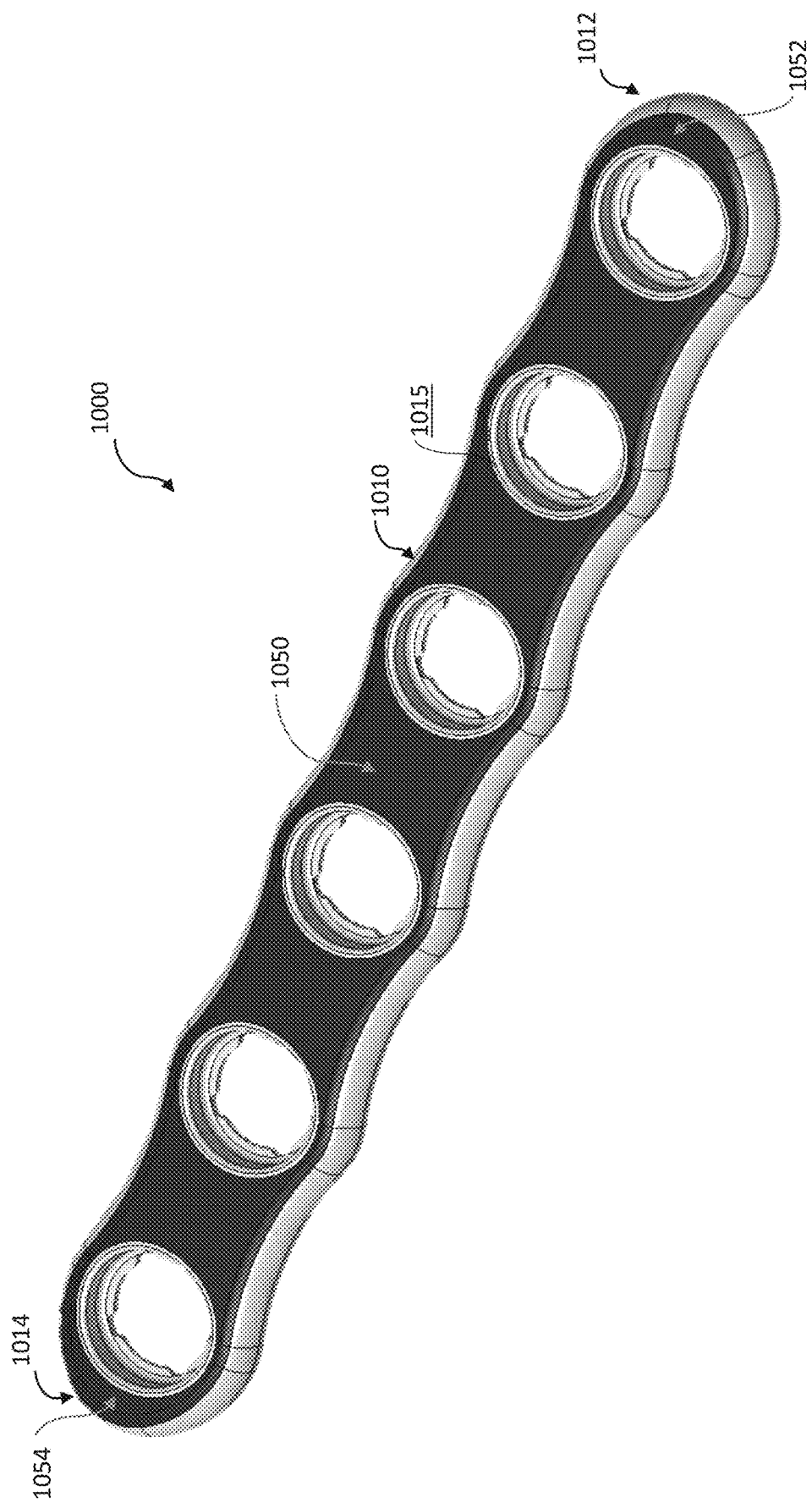
FIG. 20A illustrates a perspective view of the example bone plate illustrated in FIG. 20.

As illustrated in FIG. 20, the main body 1010 has a main body first end 1012, a main body second end 1014, a main body third end 1016, a main body fourth end 1018, a lengthwise axis 1011 that extends between the main body first end 1012 and the main body second end, a first surface 1015, a second surface 1017, a first surrounding edge 1019, a second surrounding edge 1021, a first set of openings 1020, and a wall 1022. In addition, each opening of the set of openings 1020 defines a recess 1070 that extends to a recess base 1072, and each opening of the set of openings 1020 includes a locking member 1074 that defines a plurality of notches 1076 similar to the bone plate 800 illustrated in FIG. 18.

Figure 21:
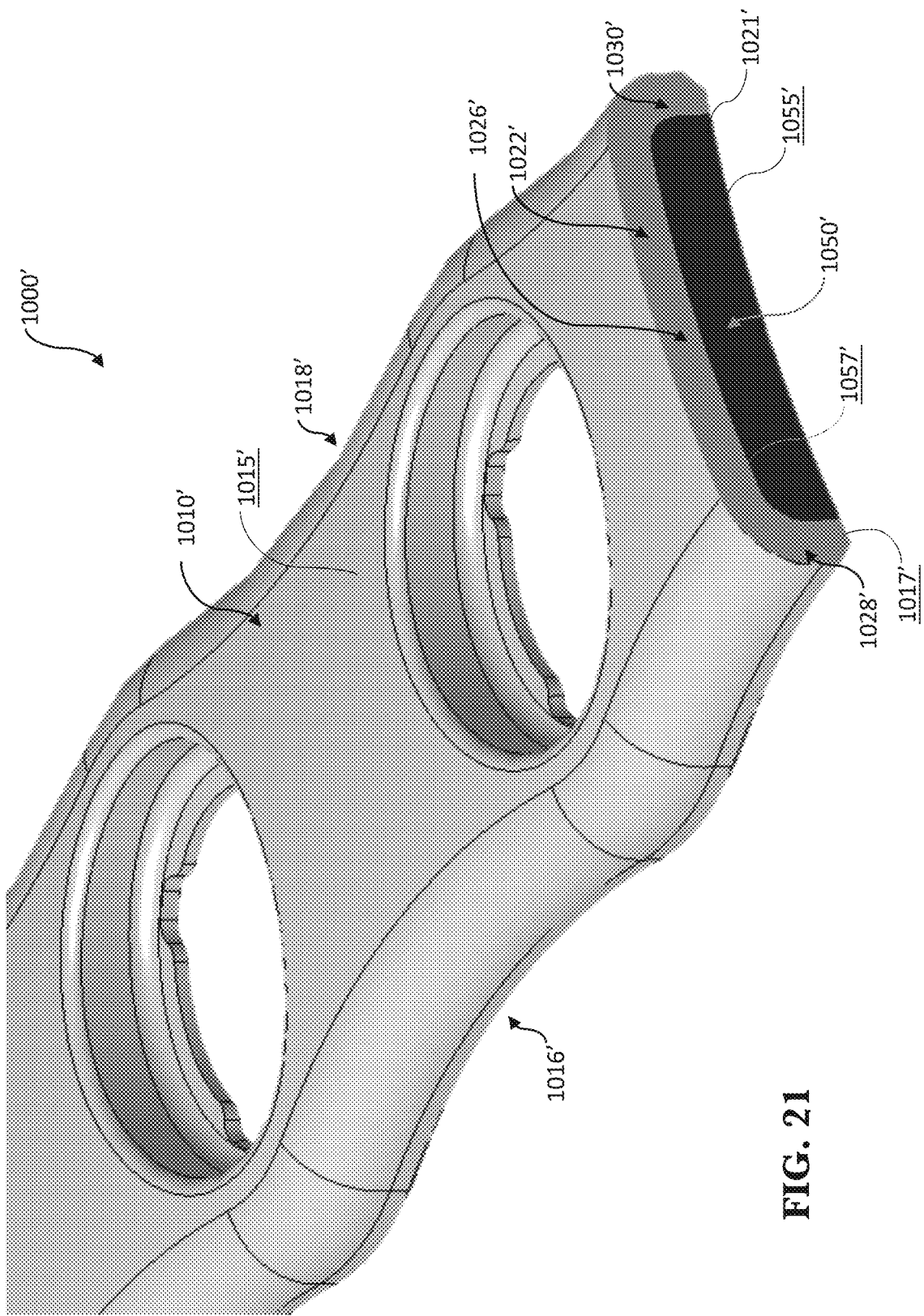
FIG. 21 illustrates a perspective view, partially broken away, of another example bone plate.
Figure 21A:
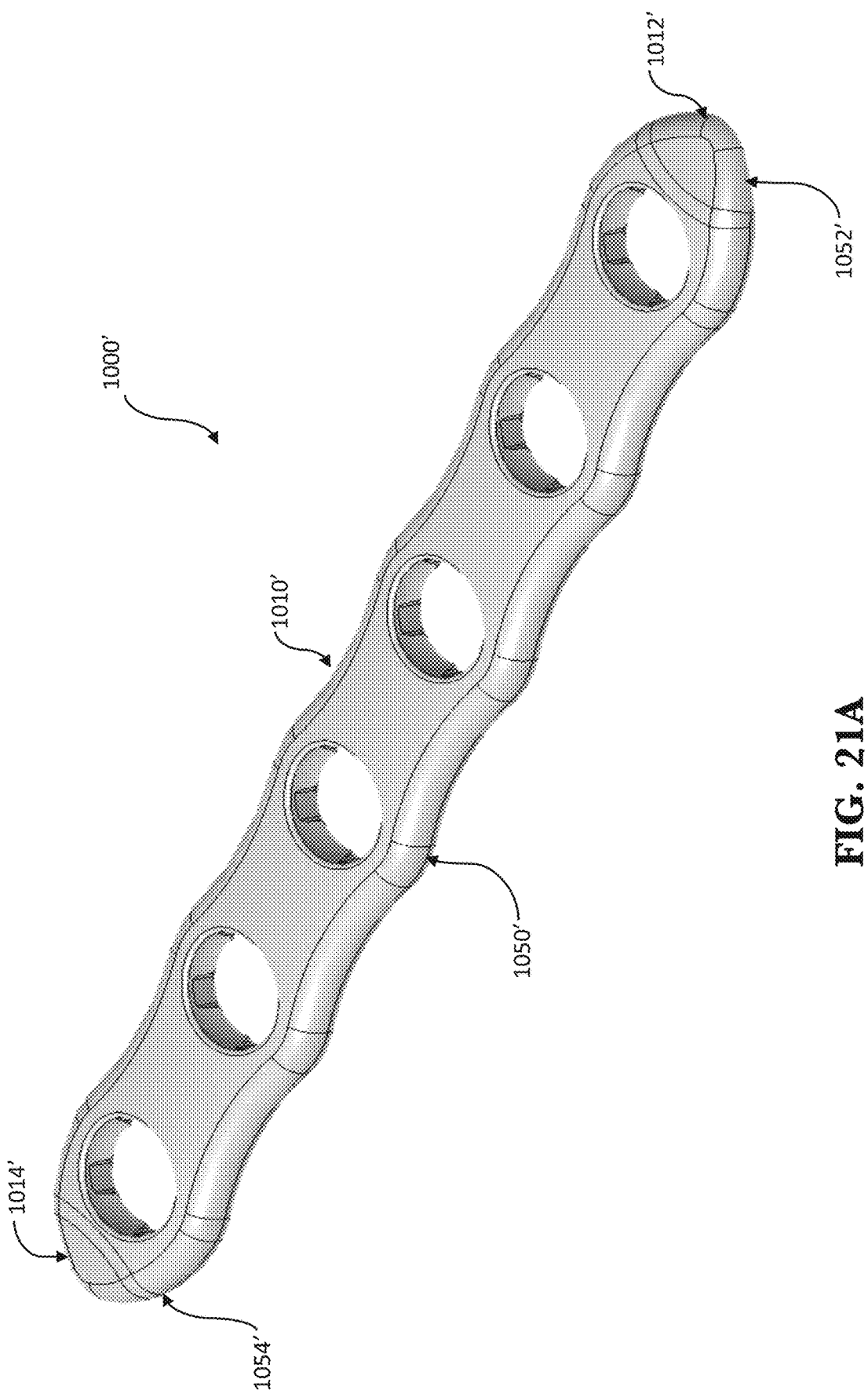
FIG. 21A illustrates a perspective view of the example bone plate illustrated in FIG. 21.

The wall 1022 includes a first portion 1026, a second portion 1028, and a third portion 1030. In this illustrated embodiment, the first, second, and third portions 1026, 1028, 1030 are continuous with each other between the main body third and fourth ends 1016,1018. The wall 1002 also extends between the main body first end 1012 and the main body second end. The first portion 1026 of the wall 1022 extends between second and third portions 1028, 1030. The second portion 1028 of the wall 1022 is disposed on the main body third end 1016. The third portion 1030 of the wall 1022 is disposed on the main body fourth end 1018. As best illustrated in FIG. 20, the first portion 1026 defines a length 1023 that is measured between the second and third portions 1028, 1030 of the wall 1022. In addition, each of the second and third portions 1028, 1030 defines a length measured between the first portion 1026 of the main body 1010 and the first surrounding edge 1019 where the second portion 1028 defines a second portion length 1025 and the third portion 1030 defines a third portion length 1027. Each of the second and third portions 1028, 1030 extends toward either the first or second surrounding edges 1019, 1021 of the main body 1010 on an axis that is perpendicular to the lengthwise axis 1011 of the main body 1010. As illustrated in FIG. 20, the wall 1022 faces toward the first surrounding edge 1019 such that each of the second and third portions 1028, 1030 of the wall 1022 extends toward the first surrounding edge 1019. As illustrated in FIG. 21, the wall 1022' faces toward the second surrounding edge 1021' such that each of the second and third portions 1028',1030' of the wall 1022' extend toward the second surrounding edge 1021'. The first, second, and third portions 1026',1028',1030' of the wall 1022' are considered advantageous at least because once the support member 1050' is introduced to the main body 1010', each of the first, second, and third portions 1026',1028',1030' of the wall 1022' interfaces with the support member 1050' to prevent axial or rotational movement between the main body 1010' and the support member 1050' such that the wall 1022' of the main body 1010' retains the support member 1050'.

The support member 1050 has a support member first end 1052, a support member second end 1054, a lengthwise axis 1053 that extends between the support member first end 1052 and the support member second end, a third surface 1057, and a fourth surface 1055. The support member first end 1052 is positioned toward the main body first end 1012, and the support member second end is positioned toward the main body second end. In the illustrated embodiment, the third surface 1057 of the support member 1050 may engage either the first surface 1015 of the main body 1010 or the second surface 1017 of the main body 1010. As illustrated in FIG. 20, the third surface 1057 of the support member 1050 engages the first surface 1015 of the main body 1010, the first surrounding edge 1019, and the first, second, and third portions 1026, 1028, 1030 of the wall. As illustrated in FIG. 21, the third surface 1057' of the support member 1050' engages the second surface 1017' of the main body 1010', the second surrounding edge 1021', and the first, second, and third portions 1026',1028',1030' of the wall 1022'.

The attachment between the support member 1050 and the main body 1010 is considered advantageous at least because the attachment prevents axial or rotational movement between the main body 1010 and the support member 1050 while the bone plate 1000 is attached to a patient's bone. Additionally, the combination of the main body 1010 and the support member 1050 is considered advantageous at least because this combination provides a user, such as a surgeon, with sufficient observation of the bone fracture since the bone plate remains partially opaque to assist the user in locating both the bone plate and the bone fracture simultaneously. Furthermore, the inventors have determined that a bone plate having a wall disposed on the second surface of the main body as illustrated in FIG. 21 provides desirable performance characteristics, including a favorable balance between strength and radio translucency of the main body and the support member.

Figure 22:
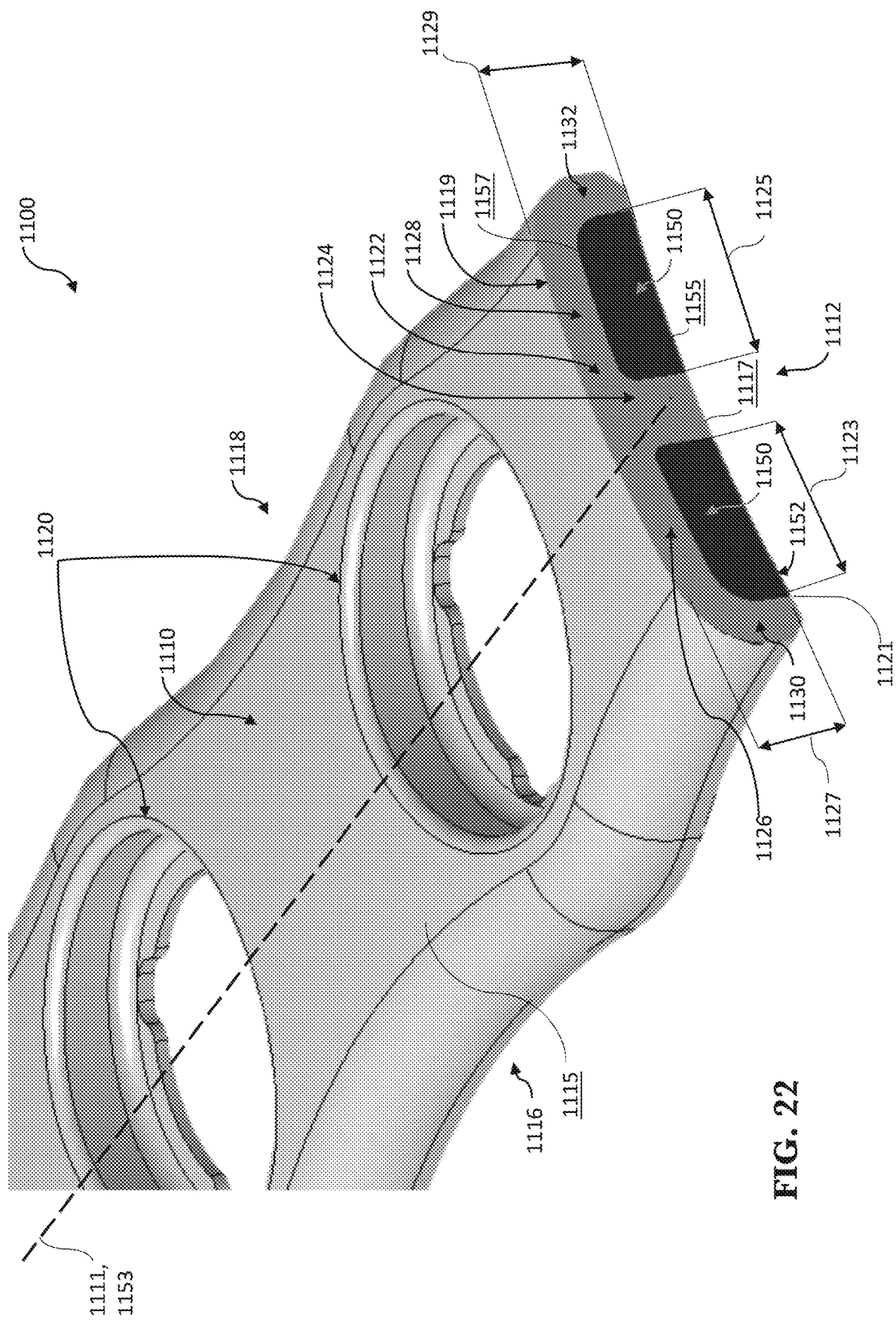
FIG. 22 illustrates a perspective view, partially broken away, of another example bone plate.
Figure 23:
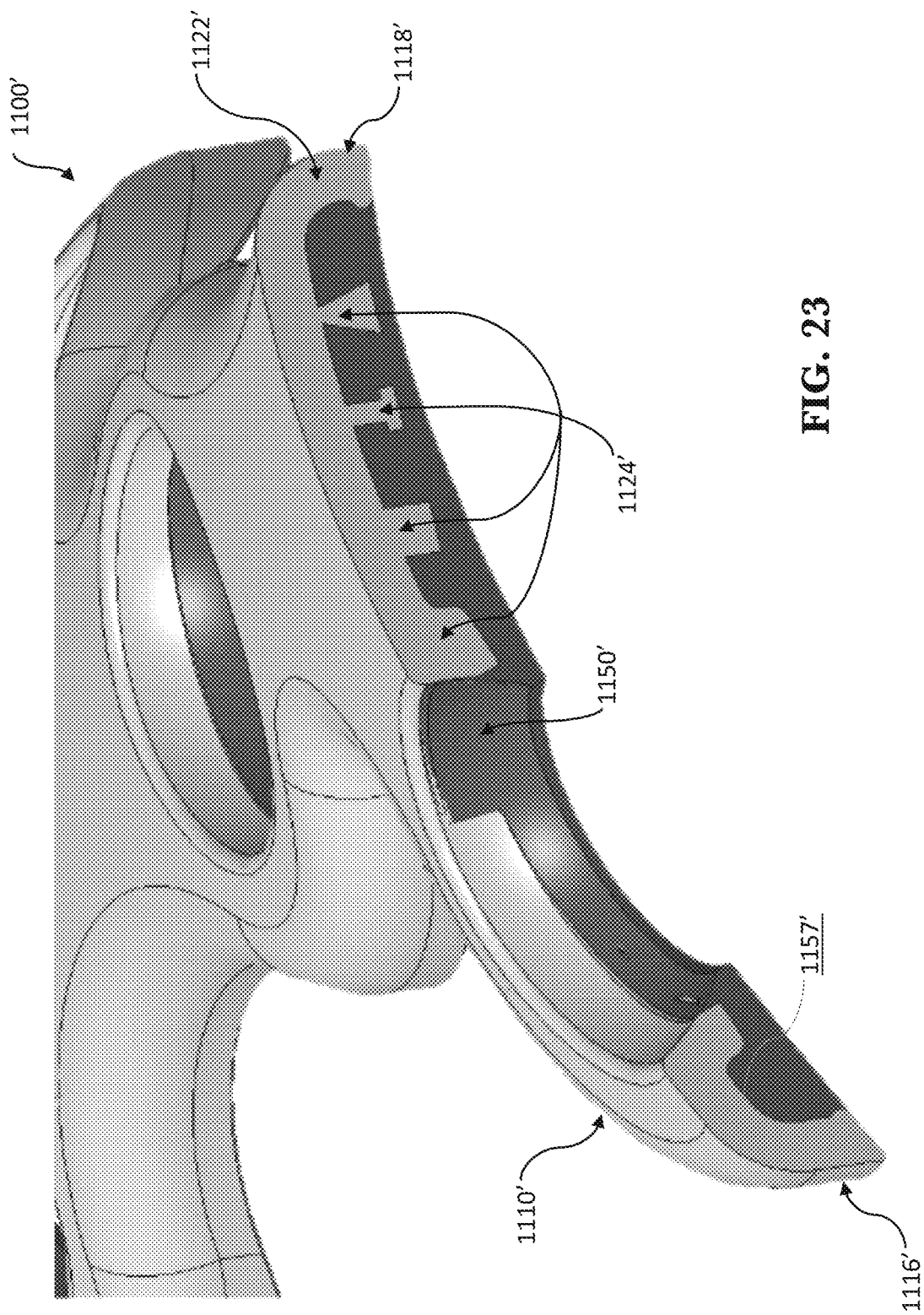
FIG. 23 illustrates a perspective view, partially broken away, of another example bone plate.

FIGS. 22 and 23 illustrates another example bone plate 1100. The bone plate 1100 is similar to the bone plate 800 described above, except as detailed below. The bone plate 1100 includes a main body 1110 and a support member 1150.

The main body 1110 includes a main body first end 1112, a main body second end (not illustrated), a main body third end 1116, a main body fourth end 1118, a lengthwise axis 1111 that extends between the main body first end 1112 and the main body second end, a first surface 1115, a second surface 1117, a first surrounding edge 1119, a second surrounding edge 1121, a first set of openings 1120, and a wall 1122. In addition, each opening of the set of openings 1120 defines a recess 1170 that extends to a recess base 1172, and each opening of the set of openings 1120 includes a locking member 1174 that defines a plurality of notches 1176 similar to the bone plate 800 illustrated in FIG. 18.

As illustrated in FIG. 22, the wall 1122 includes a first portion 1126, a second portion 1128, a third portion 1130, a fourth portion 1132, and a projection 1124. The first portion 1126 of the wall 1122 is positioned between the third portion 1130 and the projection 1124. The second portion 1128 of the wall 1122 is positioned between the fourth portion 1132 and the projection 1124. The third portion 1130 of the wall 1122 is positioned on the main body third end 1116. The fourth portion 1132 is positioned on the main body fourth end 1118. Each of the first, second, third, and fourth portions 1126, 1128, 1130, 1132 of the wall 1122 and the projection 1124 are disposed opposite to the first surface 1115 of the main body 1110. In addition, each of the first and second portions 1126, 1128 of the wall 1122 extends along an axis that is perpendicular to the lengthwise axis 1111 of the main body 1110. Each of the third and fourth portions 1128, 1130 of the wall 1122 extends away from the first surface 1115 along an axis that is perpendicular to the lengthwise axis 1111 of the main body 1110. The projection 1124 is disposed along a portion of the wall 1122 between the main body third and fourth ends 1116, 1118 and extends away from the wall 1122 on an axis that is perpendicular to the lengthwise axis 1111 of the main body 1110. The first portion 1126 includes a first length 1123 that is measured between the third portion 1130 and the projection 1124. The second portion 1128 includes a second length 1125 that is measured between the third portion 1130 and the projection 1124. Each of the third and fourth portions 1130, 1132 defines a third and fourth length 1127, 1129. The third and fourth lengths 1127, 1129 are measured from the second surrounding edge 1121 to the first surface 1115. In the illustrated embodiment, the first and second lengths 1123, 1125 are equal to each other, and the third and fourth lengths 1127, 1119 are equal to each other. Moreover, the first and second lengths 1123, 1125 are greater than each of the third and fourth lengths 1127, 1129.

The first, second, third, and fourth portions 1126, 1128, 1130, 1132 of the wall 1122 and the projection 1124 are considered advantageous at least because once the support member 1150 is introduced to the main body 1110, each of the first, second, third, and fourth portions 1126, 1128, 1130, 1132 and the projection 1124 interfaces with the third surface 1157 of the support member 1150 to prevent axial or rotational movement between the main body 1110 and the support member 1150, which is described in more detail below. Furthermore, the addition of the projection 1124 is considered advantageous at least because the projection 1124 provides additional strength and retention between the main body 1110 and the support member 1150 once the bone plate 1100 is placed and attached to a patient's bone.

While the main body 1110 describes and illustrates the wall 1122 having a single projection 1124, the wall 1122 may have any suitable number of projections along the wall 1122. A skilled artisan will be able to select an appropriate number of projections for a wall according to an embodiment based on various considerations, including the size, shape, and configuration of the main body. Examples of a suitable number of projections defined by a wall include, one, two, plurality, three, four, five, six, or any other suitable number of passageways of a first set of passageways for a particular application. As illustrated in FIG. 22, the wall 1122 includes a single projection 1124 defined between the main body third and fourth ends 1116, 1118. Alternatively, as illustrated in FIG. 23, the wall 1122' of the main body 1110' includes a plurality of projections 1124' defined between the main body third and fourth ends 1116',1118'. The wall 1122' can also define any additional structural configurations that are suitable for a bone plate 1200'. Examples of a suitable structural configurations for a wall include ribs, a single protrusion, multiple protrusions, beams, interlaced structures, porous structures, and any other suitable structural configurations for a particular application.

The support member 1150 has a support member first end 1152, a support member second end (not illustrated), a lengthwise axis 1153 that extends between the support member first end 1152 and the support member second end, a third surface 1157, and a fourth surface 1155. The support member first end 1152 is positioned toward the main body first end 1112, and the support member second end is positioned toward the main body second end. As illustrated in FIG. 22, the third surface 1157 cooperatively engages each of the first, second, third, and fourth portions 1126, 1128, 1130, 1132 of the wall 1122 and the projection 1124 once the support member 1150 is formed within the main body 1110 during the molding process. Alternatively, as illustrated in FIG. 23, the third surface 1157' cooperatively engages each of the wall 1122' and a plurality of projections 1124' once the support member 1150' is formed within the main body 1110' during the molding process. The attachment between the support member 1150 and the main body 1110 in this embodiment is considered advantageous at least because the attachment between the support member 1150 and retaining member 1122 prevents axial or rotational movement between the main body 1110 and the support member 1150 once the bone plate 1100 is placed and attached to patient's bone. Additionally, the combination of the main body 1110 and the support member 1150 is considered advantageous at least because this combination provides a user, such as a surgeon, with sufficient observation of the bone fracture since the bone plate remains partially opaque to assist the user in locating both the bone plate and the bone fracture simultaneously.

Figure 24:
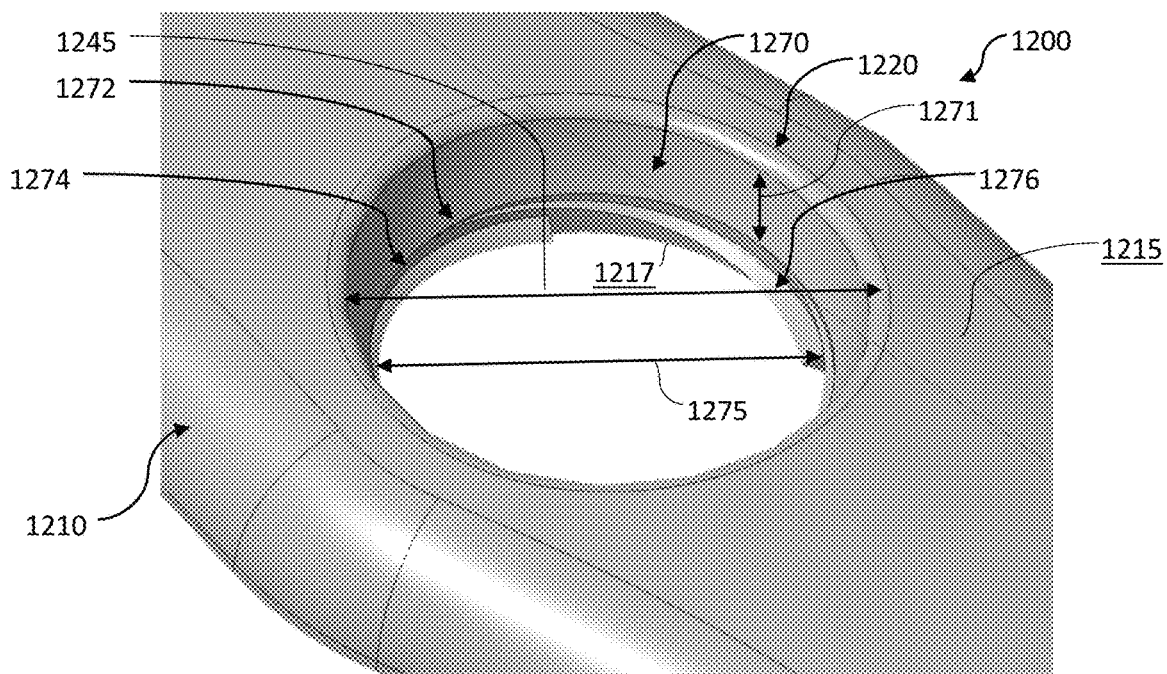
FIG. 24 illustrates a partial perspective view of another example bone plate.
Figure 25:
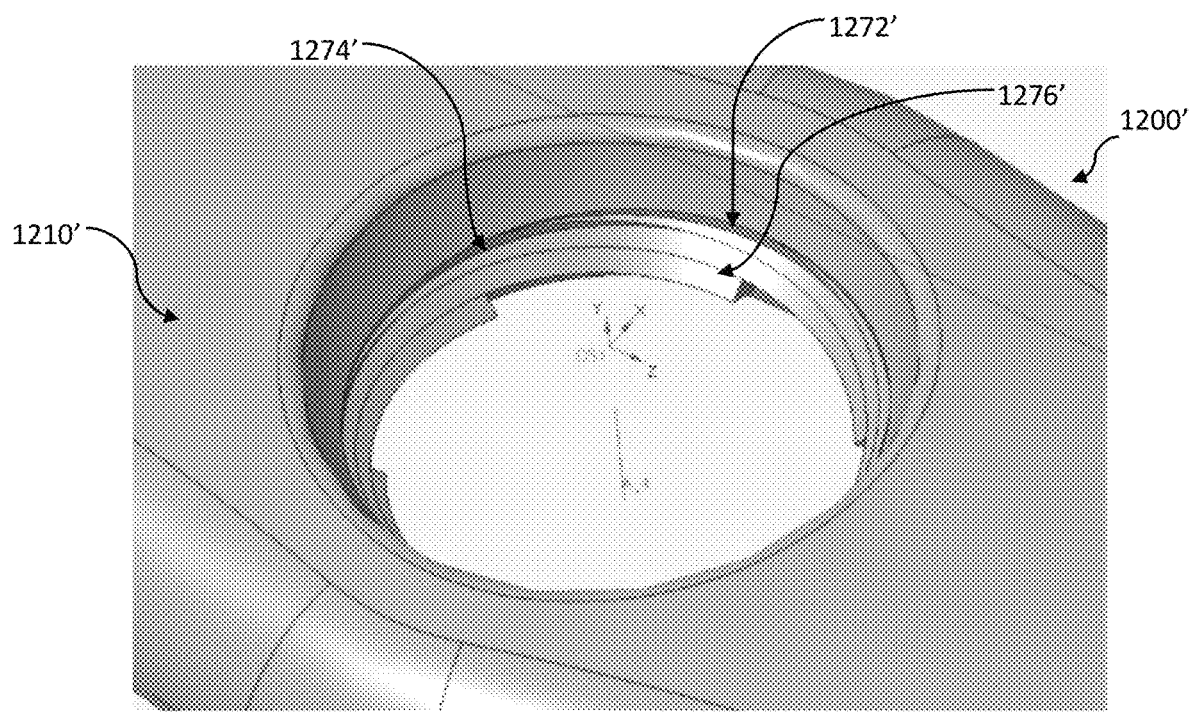
FIG. 25 illustrates a partial perspective view of another example bone plate.

FIGS. 24 and 25 illustrates another example bone plate 1200. The bone plate 1200 is similar to bone 800 described above, except as detailed below. The bone plate includes a main body 1210 and a support member (not illustrated).

In the illustrated embodiment, the main body 1210 includes a first set of openings 1220. Each opening of the first set of openings 1220 defines a recess 1270 that extends from the first surface 1215 into the main body 1210 at a recess length 1271. Each recess 1270 terminates at a recess base 1272 that is disposed between the first and second surfaces 1215, 1217 of the main body 1210. Each opening of the first set of openings 1220 also defines a locking member 1274 that is disposed circumferentially about each recess base 1272. Each locking member 1274 also defines a locking member diameter 1275 that extends between the main body third end 1216 and the main body fourth end 1218. In the illustrated embodiment, the locking member diameter 1275 is less than each opening diameter 1245 of the first set of openings 1220. However, in this illustrated embodiment, each locking member 1274 also defines a plurality of threads 1276. Each thread of the plurality of threads 1276 extends away from the locking member 1274 and extends toward the first surface 1215 of the main body 1210. In addition, each thread of the plurality of threads 1276 illustrated in this embodiment creates a ramped surface that can be measured relative to a lengthwise axis of the main body 1210. Furthermore, the plurality of threads 1276 also ends abruptly toward the first surface 1215 of the main body 1210. The abruption of the plurality of threads 1276 is considered advantageous at least because this abruption prevents the reversing of the locking screw 1500 once the screw is inserted into the bone plate 1200 and a patient's bone.

The plurality of threads 1276 defined by each locking member 1274 is considered advantageous at least because the plurality of threads 1276 provides a structural interface that allows a locking screw 1500, described in more detail below, to be inserted through an opening of the first set of openings 1220 and to be secured to the bone plate 1200 once the locking screw 1500 has been inserted into a desired location of a patient's bone. Furthermore, the locking member 1274 is considered advantageous at least because the locking member 1274 allows a user, such as a surgeon, to introduce a locking screw 1500 into an opening of the first set of openings 1220 at multiple angles relative to the lengthwise axis 1211 of the main body 1210. The locking screw 1500 can be introduced at multiple angles into an opening of the first set of openings 1220 because the plurality of threads 1276 gradually cuts and forms a head member thread (not illustrated) into the head member surface 1539 of the locking screw 1500, which is described in more detail below.

The plurality of threads 1276 of each locking member 1274 may have any suitable number of threads for a plurality of threads. A skilled artisan will be able to select an appropriate number of threads according to an embodiment based on various considerations, including the configuration of a locking screw or medical device that is to be received by each thread of a locking member. Examples of a suitable number of threads defined by a locking member include, one, two, plurality, three, four, five, six, or any other suitable number of threads of a locking member for a particular application. As illustrated in FIG. 24, the main body 1210 has a locking member 1274 that defines at least two threads 1276 that are disposed circumferentially around each recess base 1272. Alternatively, as illustrated in FIG. 25, the main body 1210' has a locking member 1274' that defines a plurality of threads 1276' that is disposed circumferentially around each locking member 1274'. In addition, the plurality of threads 1276' also ends abruptly toward the first surface 1215' of the main body 1210' similar to the plurality of threads 1276 illustrated in FIG. 24. The abruption of the plurality of threads 1276' is considered advantageous at least because this abruption prevents the reversing of the locking screw 1500 once the screw is inserted into the bone plate 1200' and a patient's bone.

Each locking member 1274, 1274' that defines a plurality of threads 1276, 1276' as illustrated in FIGS. 24 and 25 may be included into any suitable bone plate described and illustrated herein. A skilled artisan will be able to select an appropriate bone plate according to an embodiment based on various considerations, including the number of locking members and the number of threads. Examples of bone plates that may include locking members where each locking member defines a plurality of threads includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, and any other suitable bone plate that may include locking members where each locking member defines a plurality of threads for a particular application.

Figure 26:
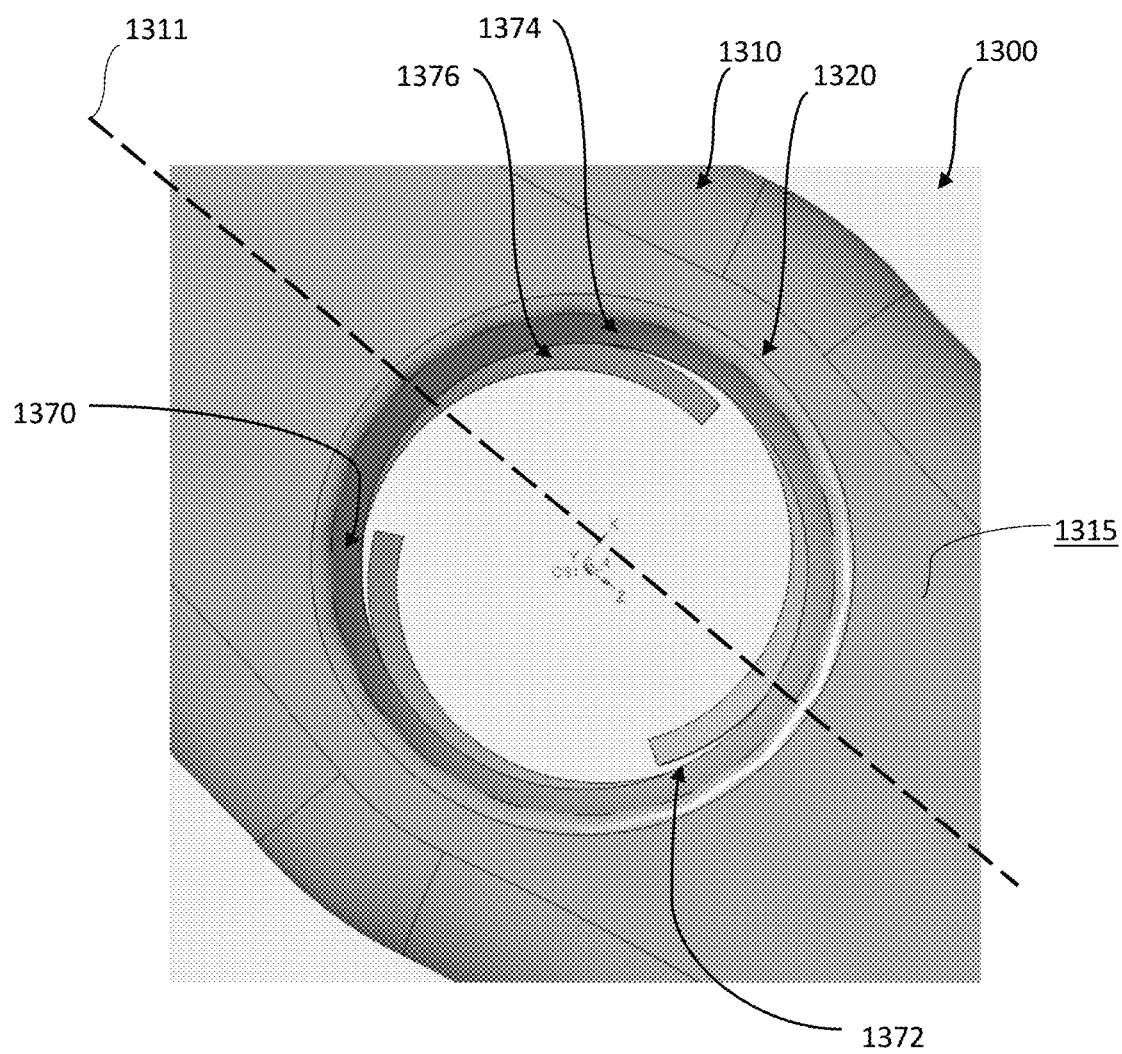
FIG. 26 illustrates a partial top view of another example bone plate.

FIG. 26 illustrates another example bone plate 1300. The bone plate 1300 is similar to bone plate 1200 described above, except as detailed below. The bone plate 1300 includes a main body 1310 and a support member (not illustrated).

In the illustrated embodiment, the main body 1310 includes a first set of openings 1320 where each opening of the first set of openings 1320 includes a recess 1370 that extends from the first surface 1315 to a recess base 1372. Each opening of the first set of openings 1320 also includes a locking member 1374 that defines a plurality of threads 1376. However, in this illustrated embodiment, a first portion of each thread of the plurality of threads 1376 is attached to the recess base 1372. Additionally, a second portion of each thread of the plurality of threads 1376 freely suspends within the recess 1370 of an opening of a first set of openings 1320. The suspension of a portion of a thread is considered advantageous at least because each thread of the plurality of threads 1376 may flex and allow a locking screw, such as locking screw 1500, to be inserted at different angles into each opening of the first set of opening 1320 relative to the lengthwise axis 1311 of the main body 1310. In addition, each thread of the plurality of threads 1376 also extends away from the recess base 1372 and toward the first surface 1315 of the main body 1310.

The structural configuration of each thread of the plurality of threads 1376 is considered advantageous at least because the plurality of threads 1376 provides a structural interface that allows a locking screw 1500, described in more detail below, to be inserted through an opening of the first set of openings 1320 and be secured to the bone plate 1300 once the locking screw 1500 has been inserted into a desired location of a patient's bone. Furthermore, the structural configuration of the plurality of threads 1376 is considered advantageous at least because this structural configuration creates a spring effect on to the locking screw 1500 such that the locking screw 1500 is prevented from reversing out of the patient's bone and/or the bone plate 1300. The locking screw 1500 can also be introduced at multiple angles into an opening of the first set of openings 1320 because the plurality of threads 1376 gradually cuts and forms a head member thread (not illustrated) into the head member surface 1539 of the locking screw 1500, which is described in more detail below.

The plurality of threads 1376 of each locking member 1374 may have any suitable number of threads for a plurality of threads. A skilled artisan will be able to select an appropriate number of threads according to an embodiment based on various considerations, including the configuration of a locking screw or medical device that is to be received by each thread of a locking member. Examples of a suitable number of threads defined by a locking member include, one, two, plurality, three, four, five, six, or any other suitable number of threads of a locking member for a particular application. In the illustrated embodiment, each locking member 1374 includes three threads 1376.

Each locking members 1374 that defines a plurality of threads 1376 may be included into any suitable bone plate described and illustrated herein. A skilled artisan will be able to select an appropriate bone plate according to an embodiment based on various considerations, including the number of locking members and the number of threads. Examples of bone plates that may include locking members where each locking member defines a plurality of threads includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, and any other suitable bone plate that may include locking members where each locking members defines a plurality of threads for a particular application.

Figure 27:
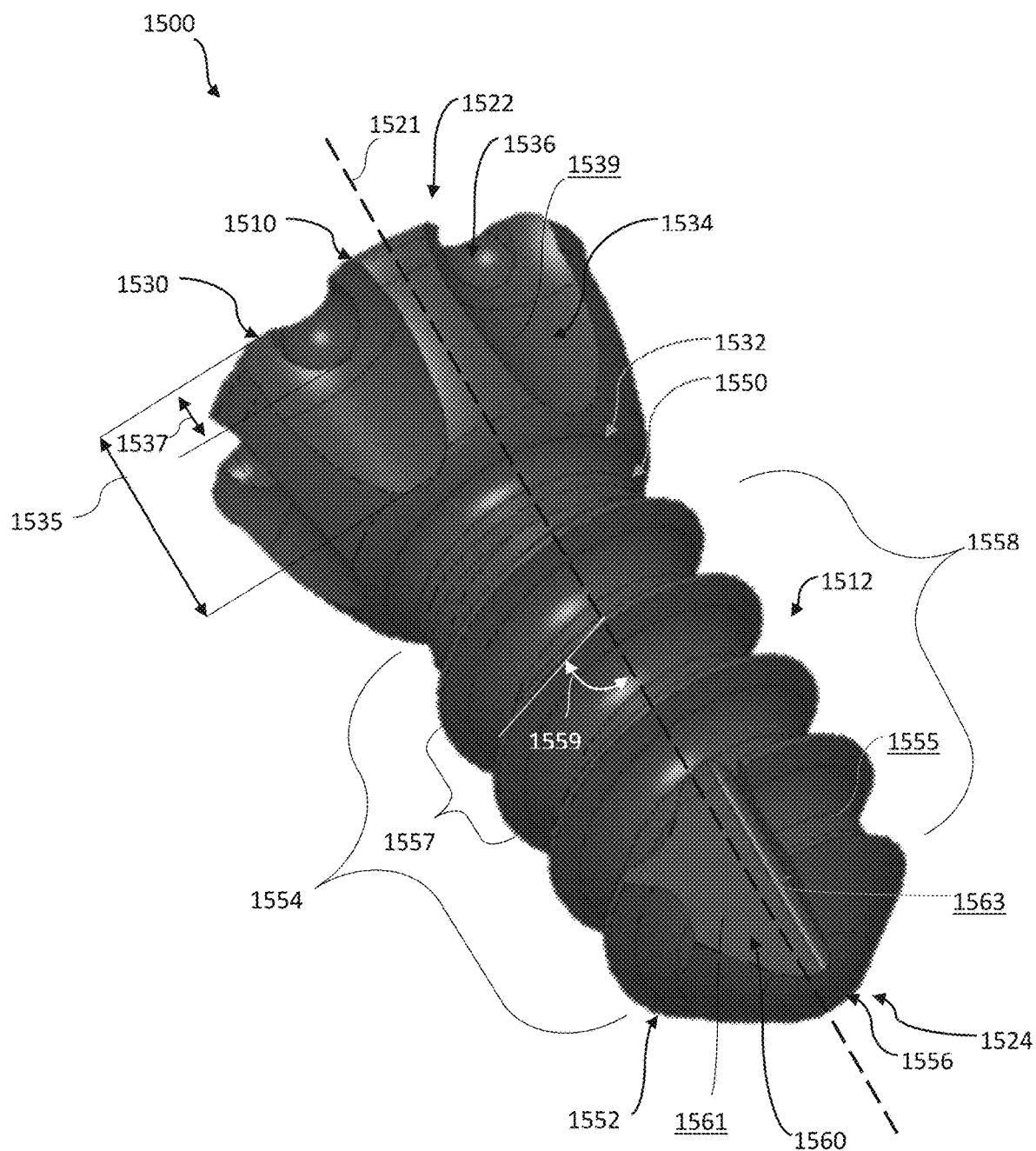
FIG. 27 illustrates a perspective view of an example locking screw.

FIG. 27 illustrates an example locking screw 1500. The locking screw 1500 has a head member 1510 and an elongated member 1512.

The locking screw 1500 has a locking screw first end 1522, a locking screw main second end 1524, and a lengthwise axis 1521 that extends between the locking screw first end 1522 and the locking screw second end 1524.

Figure 27A:
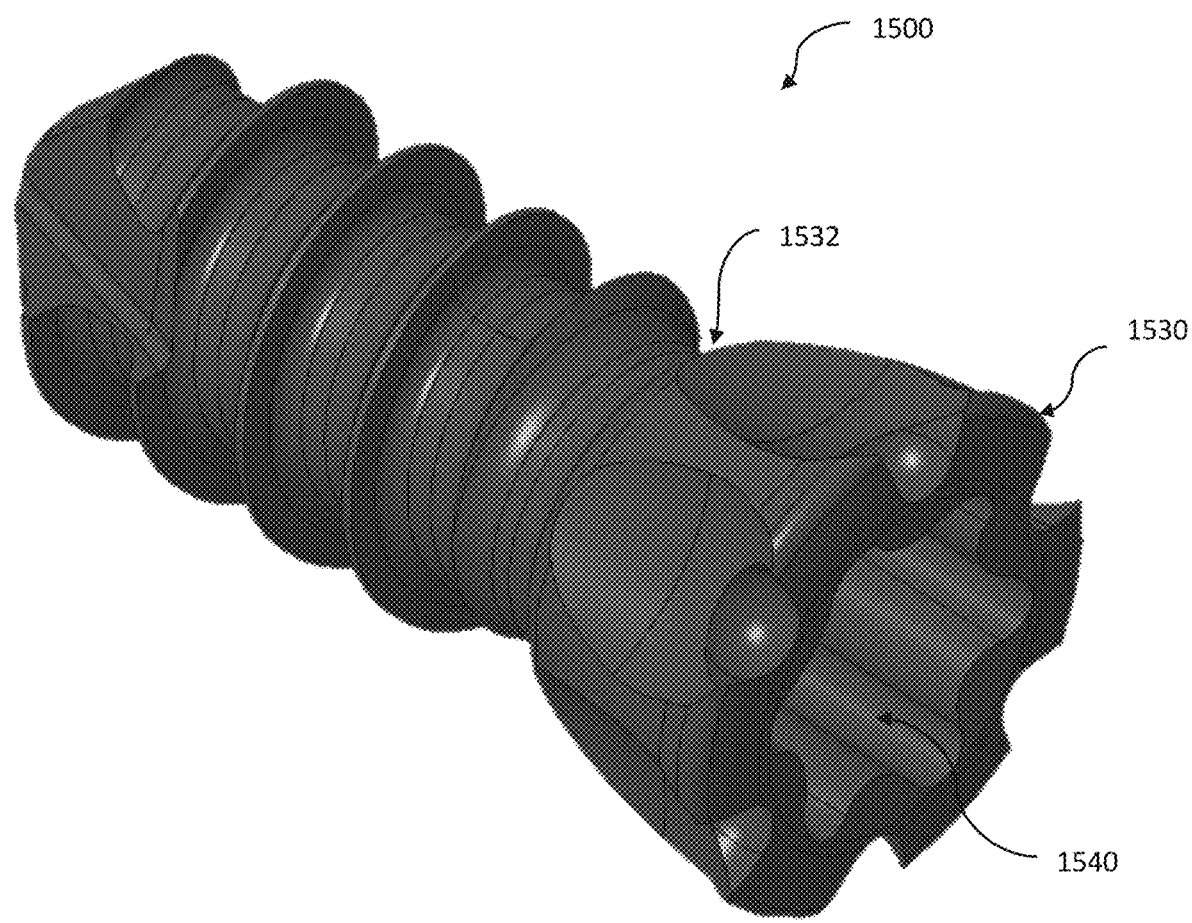
FIG. 27A illustrates another perspective view of the example locking screw illustrated in FIG. 27.

The head member 1510 includes a head member first end 1530, a head member second end 1532, a first set of grooves 1534, a second set of grooves 1536, and a head member recess 1540. The head member first end 1530 is disposed on the locking member first end 1522. The head member second end 1532 is disposed at the elongated member first end 1552 and is attached to the elongated member 1512, which is described in detail below. The head member 1510 also defines a head member surface 1539 that extends between the head member first end 1530 to the head member second end 1532. The first set of grooves 1534 is circumferentially disposed around head member 1512 between the head member first and second ends 1530, 1532. Each groove of the first set of grooves 1534 extends into the head member 1510 along an axis that is perpendicular to the lengthwise axis 1521 of the locking member 1500. In addition, each groove of the first set of grooves 1534 defines a first groove length 1535 that is measured between the head member first and second ends 1530, 1532. Additionally, the second set of grooves 1536 is circumferentially disposed around the head member first end 1530. The second set of grooves 1536 is also positioned within the first set of grooves 1534 such that a groove of the second set of grooves 1536 is positioned within a groove of the first set of grooves 1534. Each groove of the second set of grooves 1536 defines a second groove length 1537 that is measured between the head member first and second ends 1530, 1532. The first groove length 1535 is greater than the second groove length 1537. The first set of grooves 1534 is considered advantageous at least because the first set of grooves 1534 decreases the surface area needed for the head engaging thread to be formed by the plurality of threads 1276, 1376 which helps prevent the reversing of the locking screw 1500 once the locking screw 1500 is secured to a bone plate and into a patient's bone, which is described in more detail below. As illustrated in FIG. 27A, the head member 1510 may have a head member recess 1540 that extends from the head member first end

1530 toward the head member second end 1532. The head member recess 1540 may be sized and configured to receive a tool (not illustrated) that allows a user to manipulate the locking screw 1500 during use.

Prior to a user interfacing the locking screw 1500 with a locking member 1274, 1374 that defines a plurality of thread 1276, 1376, as illustrated in FIGS. 24 through 26, the head member 1510 remains blank such that a head member thread (not illustrated) is not disposed along the head member surface 1539. Once the locking screw 1500 interfaces with the locking member 1274, 1374, the plurality of threads 1276, 1376 defined by the locking member 1274, 1374 cuts a thread into the head member surface 1539 creating a head member thread that defines a head member thread width and a head member thread depth (similar to the head member thread 1738 illustrated in FIG. 30). The head member thread width is measured between each thread in the head member thread. The head member thread also extends circumferentially around the head member 1510 from the head member first end 1530 toward the head member second end 1532. Additionally, the head member thread is cut at an angle relative to the lengthwise axis 1521 of the locking screw 1500. The angle of the head member thread is dependent upon the angle in which the user inserts the locking screw 1500 into the plurality of threads 1276, 1376 defined by a locking member 1274, 1374.

The elongated member 1512 has an elongated member first end 1550, an elongated member second end 1552, a shaft 1554, and a tip 1556. The elongated member first end 1550 is attached to the head member second end 1532 such that the head member 1510 and the elongated member 1512 are continuous with each other. The elongated member second end 1552 is disposed toward the locking member second end 1524 and directly opposite to the elongated member first end 1550. The tip 1556 is disposed on the elongated member second end 1552 and extends away from the elongated member second end 1552 along the lengthwise axis 1521 of the locking screw 1500. In the illustrated embodiment, the shaft 1554 is disposed between the elongated member first and second ends 1550, 1552 with a shaft surface 1555. The shaft 1554 also defines shaft thread 1558 disposed along the shaft surface 1555 between the elongated member first and second ends 1550, 1552. Once the locking screw 1500 is inserted into an opening of a bone plate, the shaft thread 1558 interfaces with a patient's bone to secure the locking screw 1500 and the bone plate to the patient's bone.

Furthermore, the elongated member 1514 also defines a cutting blade 1560. The cutting blade 1560 extends from the tip 1556 toward the elongated member first end 1550. The cutting blade 1560 defines a cutting blade first surface 1561 that extends away from the locking screw 1500 on a plane that is perpendicular to the lengthwise axis 1521 of the locking screw 1500. Additionally, the cutting blade 1560 also defines a cutting blade second surface 1563 that extends away from the locking screw 1500 on a plane that is perpendicular to the lengthwise axis 1521 of the locking screw 1500. The cutting blade 1560 allows a user, such as surgeon, to cut a path through tissue and/or bone material in order to anchor a locking screw, such as locking screw 1500, into a location near the fracture of the patient's bone.

The structural interface between the locking screw 1500 and the locking member 1274, 1374 is considered advantageous at least because the structural interface allows a user to insert the locking screw 1500 into a locking member 1274, 1374 at multiple angles relative to a lengthwise axis of a desired bone plate. If a user selects a bone plate described herein that includes a plurality of threads 1276 defined by each locking member 1274, the plurality of threads 1276 allows a user to insert the locking screw 1500 into the plurality of threads 1276 to create a head member thread (not illustrated) at multiple angles. If a user selects a bone plate described herein that includes a plurality of threads 1376 defined by each locking member 1374, the plurality of threads 1376 also allows a user to insert the locking screw 1500 into the plurality of threads 1376 to create a head member thread (not illustrated) at multiple angles. However, the locking member 1374 that defines a plurality of threads 1376 may allow for a greater degree of angles when the locking screw 1500 is inserted into the plurality of threads 1376 given the plurality of threads 1376 provides more flexibility between the locking screw 1500 and the plurality of threads 1376.

A user may insert the locking screw 1500 into a plurality of threads 1276, 1376 at any suitable angle relative to the lengthwise axis of a bone plate. A skilled artisan will be able to determine a suitable angle for user to insert a locking screw into a plurality of threads in a particular embodiment based on various considerations, including size, shape and configuration of each plurality of threads included in a bone plate.

Figure 28:
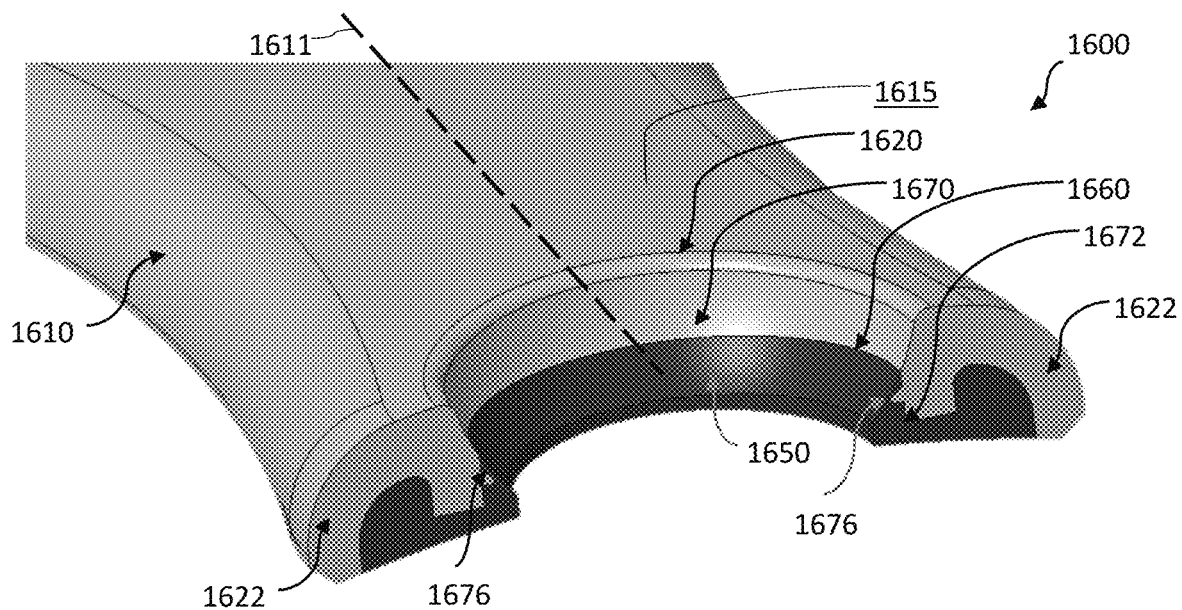
FIG. 28 illustrates a perspective view, partially broken away, of another example bone plate.
Figure 29:
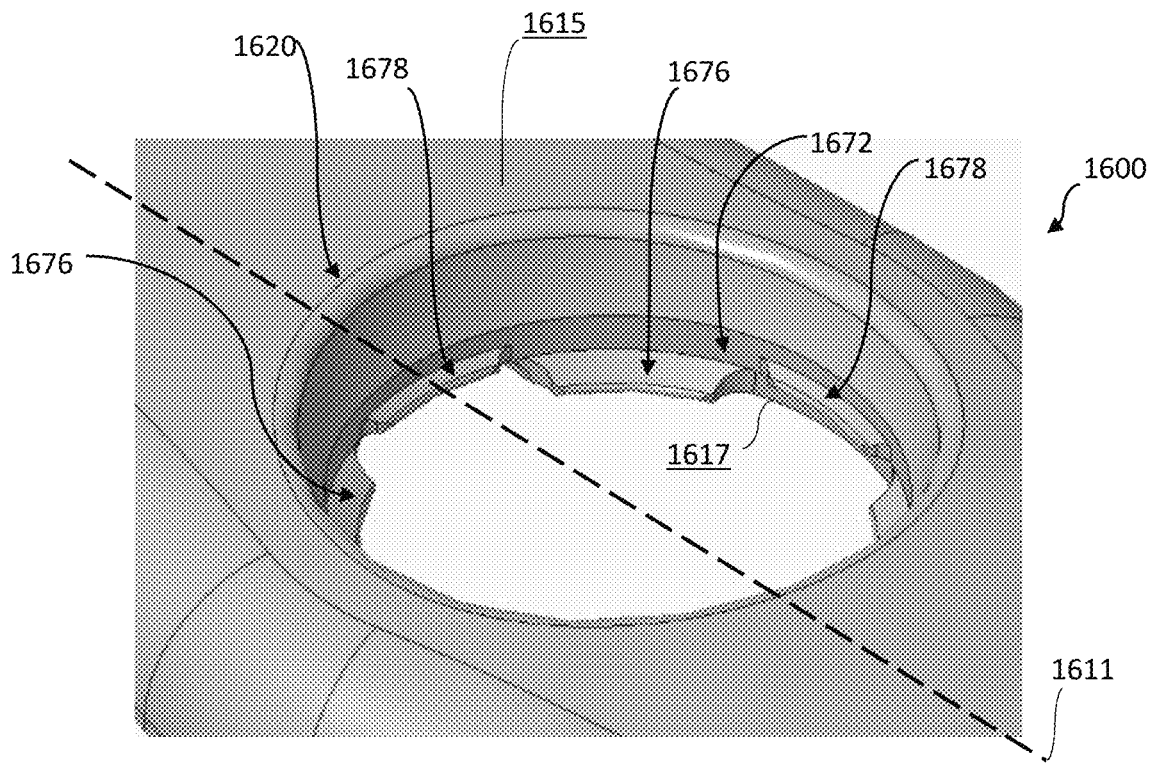
FIG. 29 illustrates a partial perspective view of the main body of the example bone plate illustrated in FIG. 28.

FIGS. 28 and 29 illustrates another example bone plate 1600. The bone plate 1600 is similar to bone plate 1200 described above, except as detailed below. The bone plate 1600 includes a main body 1610 and support member 1650.

FIG. 29 illustrates the main body 1610 prior to the support member 1650 being attached to the main body 1610. The main body 1610 includes first set of openings 1620. Each opening of the first set of openings 1620 defines a recess 1670 that extends to a recess base 1672, and each opening of the set of openings 1620 includes a locking member 1674. However, in this illustrated embodiment, the locking member 1674 defines a first plurality of pegs 1676 and a second plurality of pegs 1678. Each peg of the first and second plurality of pegs 1676, 1678 extends from recess base 1672 away from the main body 1610. As best illustrated in FIG. 29, the first plurality of pegs 1676 is disposed on a first plane that is parallel to the lengthwise axis 1611 of the main body 1610, and the second plurality of pegs 1678 is disposed on a second plane that is parallel to the lengthwise axis 1611 of the main body 1610. The first plurality of pegs 1676 is positioned at the recess base 1672 toward the second surface 1617, and the second plurality of pegs 1678 is positioned between the first plurality of pegs 1676 and the top surface 1615 of the main body 1610. The first and second pluralities of pegs 1676, 1678 is considered advantageous at least because the first and second plurality of pegs 1676, 1678 provide a structural interface that locks and/or secures the locking screw 1700 to the bone plate 1600, which is described in more detail below. Furthermore, the first and second pluralities of pegs 1676, 1678 also provide an additional attachment between the main body 1610 and the support member 1650 once a locking screw 1700 is introduced and secured to the bone plate 1600.

The first plurality of pegs 1676 may have any suitable number of pegs for a first plurality of pegs. A skilled artisan will be able to select an appropriate number of pegs according to an embodiment based on various considerations, including the size, shape and configuration of each opening of first set of openings, the locking screw, and the bone plate. Examples of a suitable number of pegs in a first plurality of pegs include one, two, plurality, three, four, five, six, or any other suitable number of pegs for a first plurality of pegs for a particular application. Additionally, the second plurality of pegs 1678 may have any suitable number of pegs for a second plurality of pegs. A skilled artisan will be able to select an appropriate number of pegs according to an embodiment based on various considerations, including the size, shape and configuration of each opening of first set of openings, the locking screw, and the bone plate. Examples of a suitable number of pegs in a second plurality of pegs include one, two, plurality, three, four, five, six, or any other suitable number of pegs for a second plurality of pegs for a particular application.

FIG. 28 illustrates the support member 1650 formed to the main body 1610. Specifically, the support member 1650 is attached to the wall 1622 of the main body 1610, a portion of each opening of the first set of openings 1620, and each peg of the first and second plurality of pegs 1676, 1678. Additionally, the support member 1650 defines a second set of openings 1660 in which a portion of the support member 1650 is attached to each recess base 1672 and is disposed within a portion of each opening of the first set of openings 1620. The attachment between support member 1650 and the first and second plurality of pegs 1676, 1678 is considered advantageous at least because this attachment provides additional strength and retention between the main body 1610 and the support member 1650 once a locking screw 1700 engages the bone plate 1600. Furthermore, the attachment between the first and second sets of openings 1620, 1660 is considered advantageous at least because this attachment allows a locking member 1700 to form a support member thread (not illustrated) circumferentially around each opening of the second set of openings 1660 once a locking screw 1700 is inserted into the bone plate 1600, which is described in more detail below. Each support member thread that is created within each opening of the second set of openings 1660 provides additional strength and retention between the locking screw 1700 and the bone plate 1600 during use such that the support member 1650 acts an additional locking feature between a portion of the locking screw 1700 and the bone plate 1600.

Each locking members 1674 that defines a first and second plurality of pegs 1676, 1678 may be included into any suitable bone plate described and illustrated herein. A skilled artisan will be able to select an appropriate bone plate according to an embodiment based on various considerations, including the number of locking members and the number of pegs for each of the first and second plurality of pegs. Examples of bone plates that may include locking members where each locking member defines a first and second plurality of pegs includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, and any other suitable bone plate that may include locking members where each locking members defines a plurality of threads for a particular application.

Figure 30:
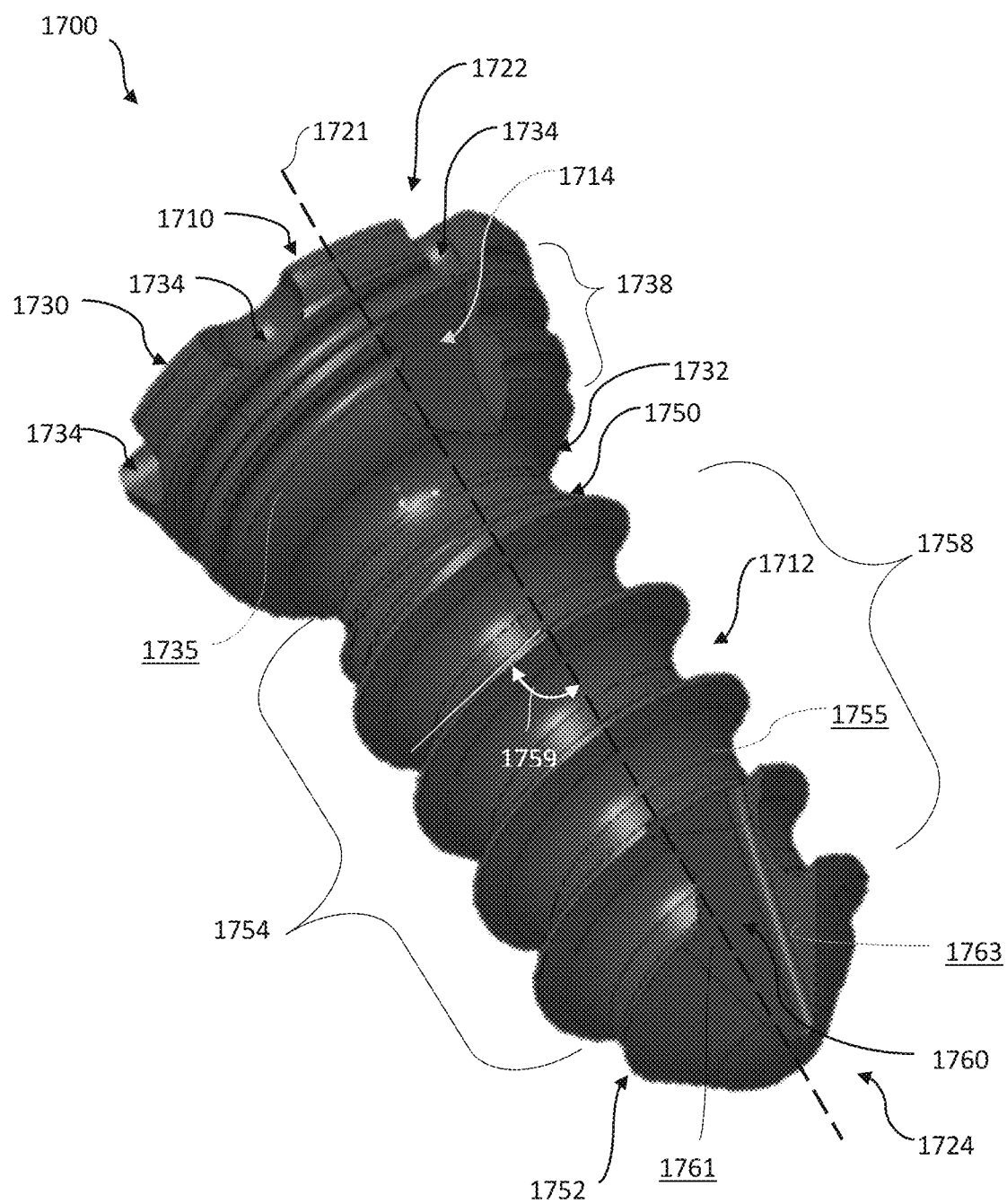
FIG. 30 illustrates a perspective view of another example locking screw.

FIG. 30 illustrates another example locking screw 1700. The locking screw 1700 is similar to bone plate 1500 described above, except as detailed below. The locking screw 1700 has a head member 1710 and an elongated member 1712.

The locking screw 1700 has a locking screw first end 1722, a locking screw main second end 1724, and a lengthwise axis 1721 that extends between the locking screw first end 1722 and the locking screw second end 1724.

Figure 30A:
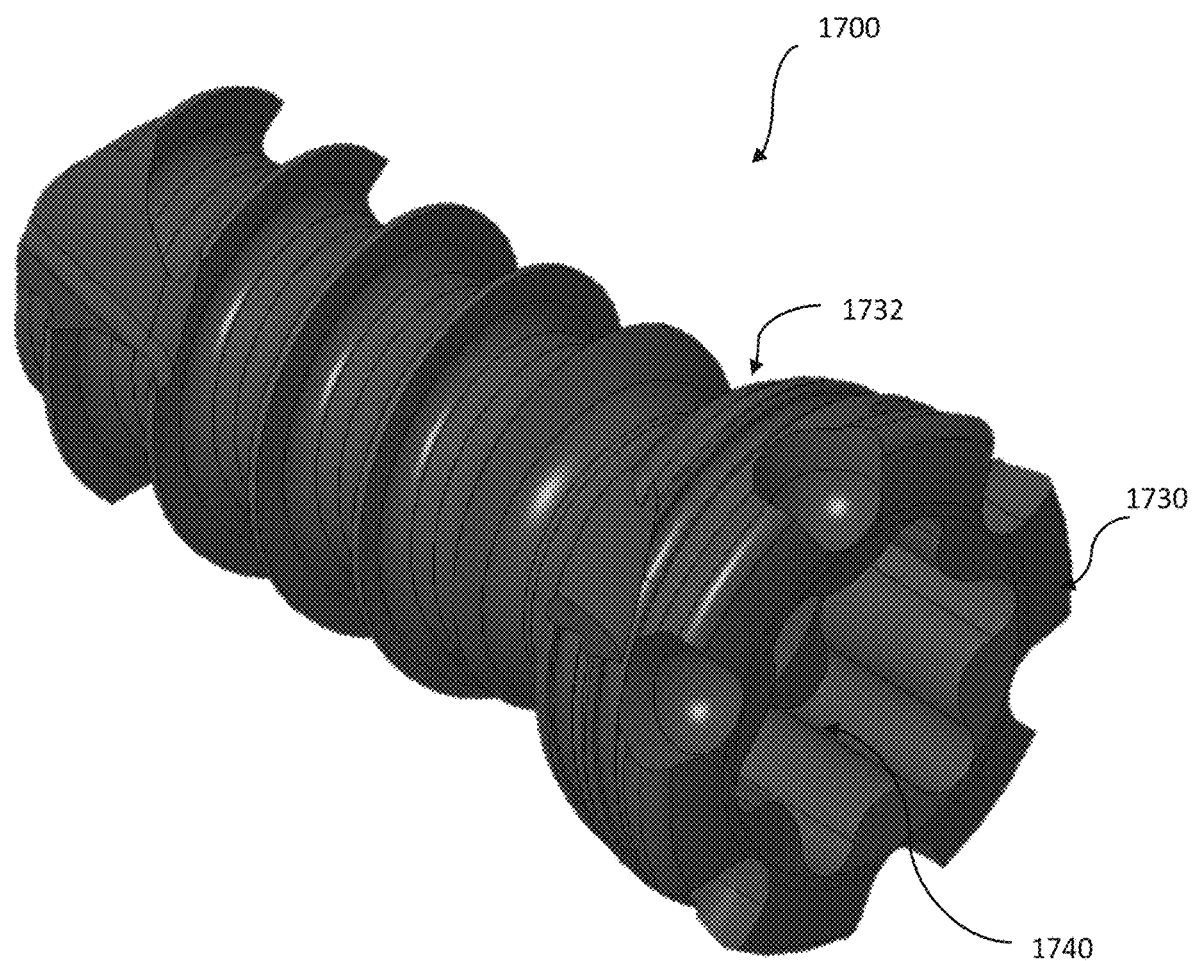
FIG. 30A illustrates another perspective view of the example locking screw illustrated in FIG. 30.

The head member 1710 includes a head member first end 1730, a head member second end 1732, a set of grooves 1734, a head member surface 1735, a head member thread 1738, and a head member recess 1740. The head member first end 1730 is disposed on the locking member first end 1722. The head member second end 1732 is disposed at the elongated member first end 1752 and is attached to the elongated member 1712, which is described in detail below. The head member 1710 also defines a curved surface that extends between the head member first end 1730 to the head member second end 1732. The set of grooves 1734 is disposed circumferentially around the head member 1710 at the head member first end 1730. Each groove of the set of grooves 1734 extends into the head member 1710 along an axis that is perpendicular to the lengthwise axis 1721 of the locking member 1700. As illustrated in FIG. 30A, the head member 1710 may have a head member recess 1740 that extends from the head member first end 1730 toward the head member second end 1732. The head member recess 1740 may be sized and configured to receive a tool (not illustrated) that allows a user to manipulate the locking screw 1700 during use. In the illustrated embodiment, the head member thread 1738 is disposed circumferentially about the head member surface 1735 and extends between the head member first and second ends 1730, 1732. The head member thread 1738 is interrupted along a portion of the head member surface 1735 at the location of the first cutting blade 1714. The first cutting blade 1714 is disposed at the head member second end 1732 and extends toward the head member first end 1730. The first cutting blade 1714 has a first cutting blade first surface 1741 and a first cutting blade second surface 1743. Each of the first cutting blade first and second surfaces 1741, 1743 extends away from the head member 1712 along a plane that is perpendicular to the lengthwise axis 1721 of the locking screw 1700.

The elongated member 1712 has an elongated member first end 1750, an elongated member second end 1752, a shaft 1754, a tip 1756, and a second cutting blade 1760. The elongated member 1712 of the locking screw 1700 is similar to the structural arrangement of the elongated member 1512 of the locking screw 1500 illustrated in FIG. 27. In this illustrated embodiment, the shaft 1754 includes a shaft thread 1758 that is disposed along a shaft surface 1755 between the elongated member first and second ends 1750, 1752.

During use, a user applies a force to the locking screw 1700 with a tool that is directed toward an opening of the first set of openings 1620 of the bone plate 1600 and an opening of the second set of openings 1660 of the support member 1650 illustrated in FIGS. 28 and 29. The elongated member 1712 of the locking screw 1700 passes through the openings of the first and second sets of openings 1620, 1660 and into the patient's body to insert the locking screw 1700 into the patient's bone. While still applying a force onto the locking screw 1700 directed toward the bone plate 1600, the user applies a rotational force on the tool causing the locking screw 1700 to rotate. Once rotating, the locking screw 1700 interfaces with the support member 1650 such that the first cutting blade 1714 cuts a support member thread into and along an opening of the second set of openings 1660 of the support member 1650. Once a support member thread is cut into an opening of the second set of openings 1660, the head member thread 1738 of the locking screw 1700 engages the support member thread to secure the locking screw 1700 to the bone plate 1600.

The structural arrangement of the first cutting blade 1714 and the head member thread 1738 is considered advantageous at least because the structural arrangement creates additional attachment strength and retention between each of the locking screw 1700 and the bone plate 1600 once the bone plate 1600 is attached and secured to a patient's bone. Furthermore, the structural interface between the locking screw 1700 and the support member 1650 is also considered advantageous at least because the structural interface allows a user to insert the locking screw 1700 into an opening of the second set of openings 1660 of the support member 1650 at multiple angles relative to lengthwise axis 1611 of the bone plate 1600.

A user may insert the locking screw 1700 into an opening of the second set of openings 1660 of the support member 1650 at any suitable angle relative to the lengthwise axis of a bone plate. A skilled artisan will be able to determine a suitable angle for user to insert a locking screw into an opening of a second set of openings for a particular embodiment based on various considerations, including size, shape and configuration of each opening of the second set of openings included in a bone plate.

Figure 31:
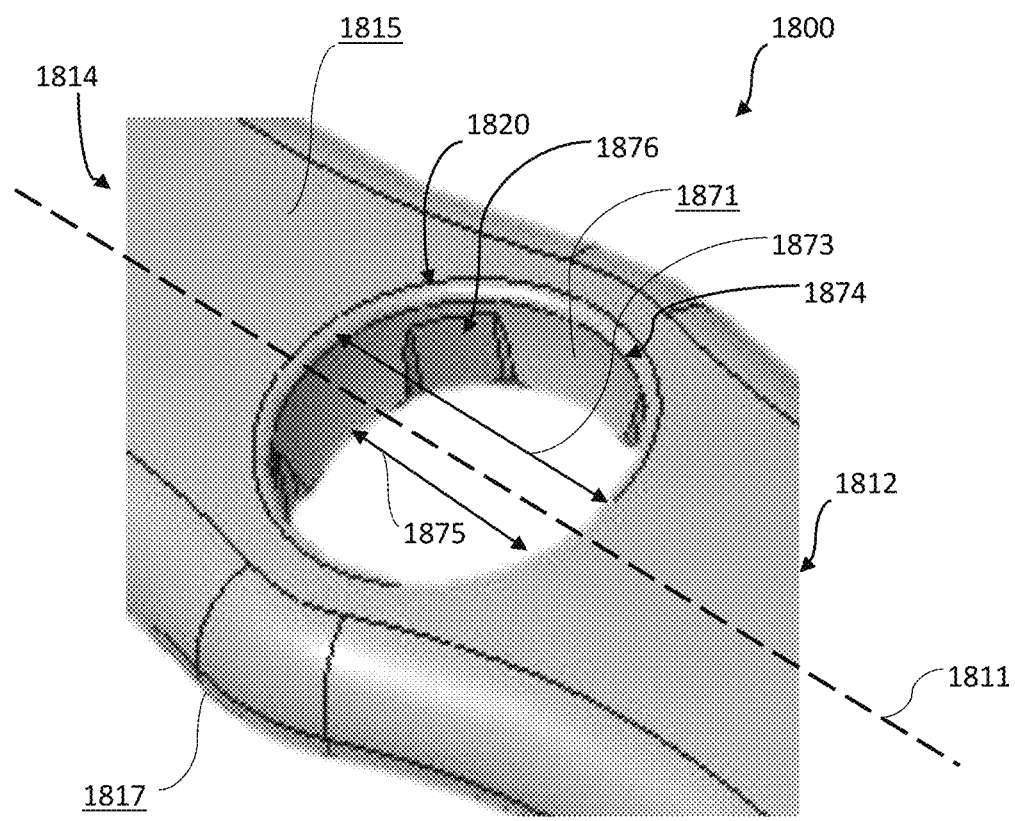
FIG. 31 illustrates a partial perspective view of another example bone plate.

FIG. 31 illustrates another example bone plate 1800. The bone plate 1800 is similar to bone plate 800 described above, except as detailed below. The bone plate 1800 includes a main body 1810 and support member (not illustrated).

The main body 1810 includes a first set of openings 1820 disposed between the main body first end 1812 and the main body second end 1814. Each opening of the first set of openings 1820 includes a locking member 1874 that defines a ramped surface 1871 that extends from the first surface 1815 to the second surface 1817 at an angle relative to the lengthwise axis 1811 of the main body 1810. Each opening of the first set of openings 1820 also defines an opening first diameter 1873 and an opening second diameter 1875 where the opening first diameter 1873 is greater than the opening second diameter 1875. Each opening first diameter 1873 is disposed on the first surface 1815 of the main body 1810, and each opening second diameter 1875 is disposed on the second surface 1817. In addition, the locking member 1874 also defines a plurality of notches 1876 that is disposed circumferentially around the locking member 1874. Each notch of the plurality of notches 1876 extends into the ramped surface 1871 and the main body 1810 at a depth measured from the ramped surface 1871 to the main body 1810. Each notch of the plurality of notches 1876 is also disposed on a plane that is perpendicular to the lengthwise axis 1811 of the main body 1810. The combination of the ramped surface 1871 and the plurality of notches 1876 is considered advantageous at least because this combination provides a structural interface that locks and/or secures a suitable locking screw or a medical device to the bone plate 1800 during use.

The plurality of notches 1876 may have any suitable number of notches for plurality of notches. A skilled artisan will be able to select an appropriate number of notches according to an embodiment based on various considerations, including the size, shape and configuration of each opening of first set of openings, a locking screw, and a bone plate. Examples of a suitable number of notches in a plurality of notches include one, two, plurality, three, four, five, six, or any other suitable number of notches for a first plurality of notches for a particular application. Additionally, the plurality of notches 1876 may be positioned at any angle relative to the lengthwise axis 1811 of the main body 1810 that is considered suitable for a particular application.

Each locking member 1874 that defines a plurality of notches 1876 may be included into any suitable bone plate described and illustrated herein. A skilled artisan will be able to select an appropriate bone plate according to an embodiment based on various considerations, including the number of locking members and the number of notches for a plurality of notches. Examples of bone plates that may include locking members where each locking member defines a plurality of notches includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, bone plate 1800 and any other suitable bone plate that may include locking members where each locking members defines a plurality of notches for a particular application.

Figure 32:
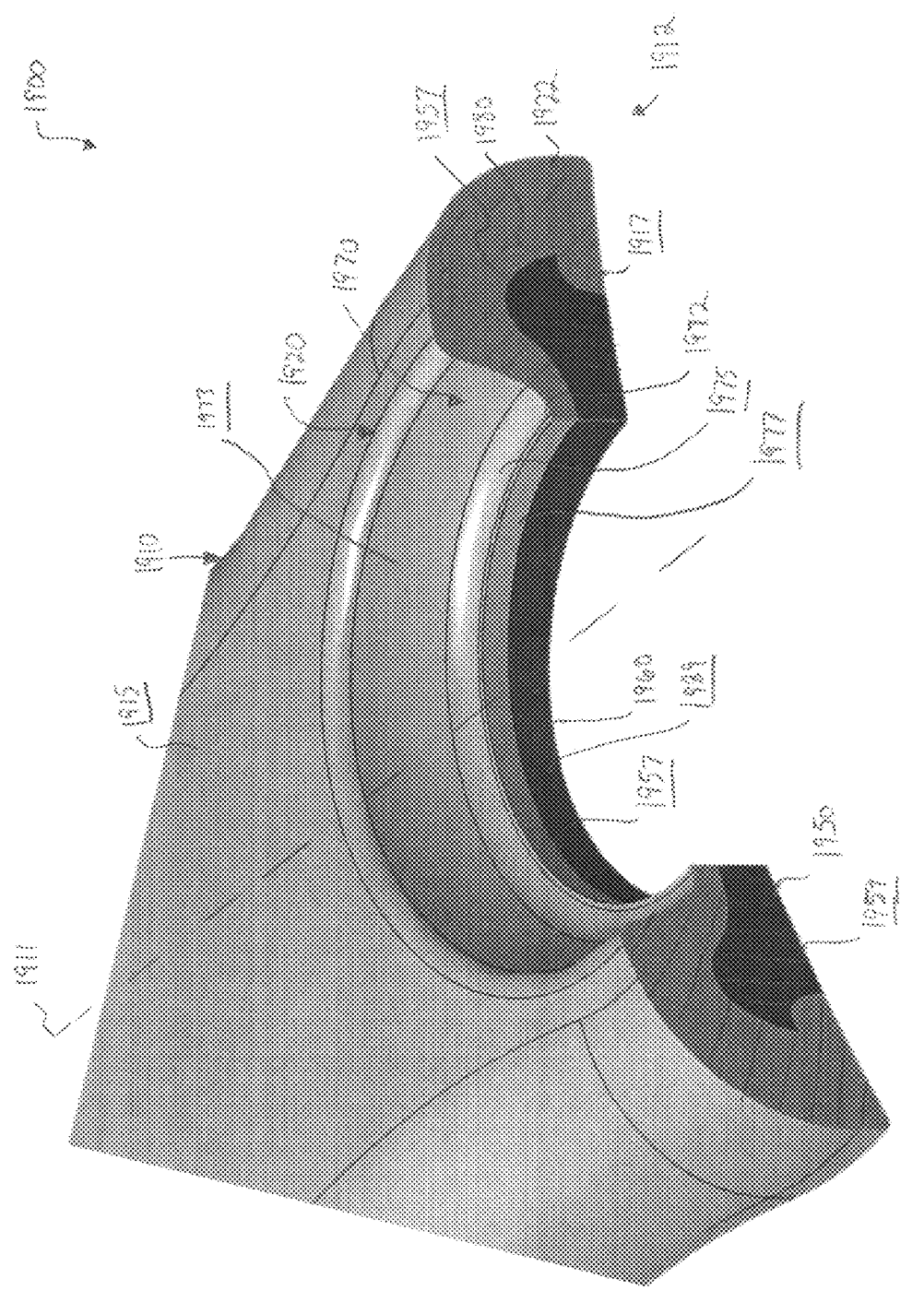
FIG. 32 illustrates a partial cross-sectional view of another example bone plate.
Figure 33:
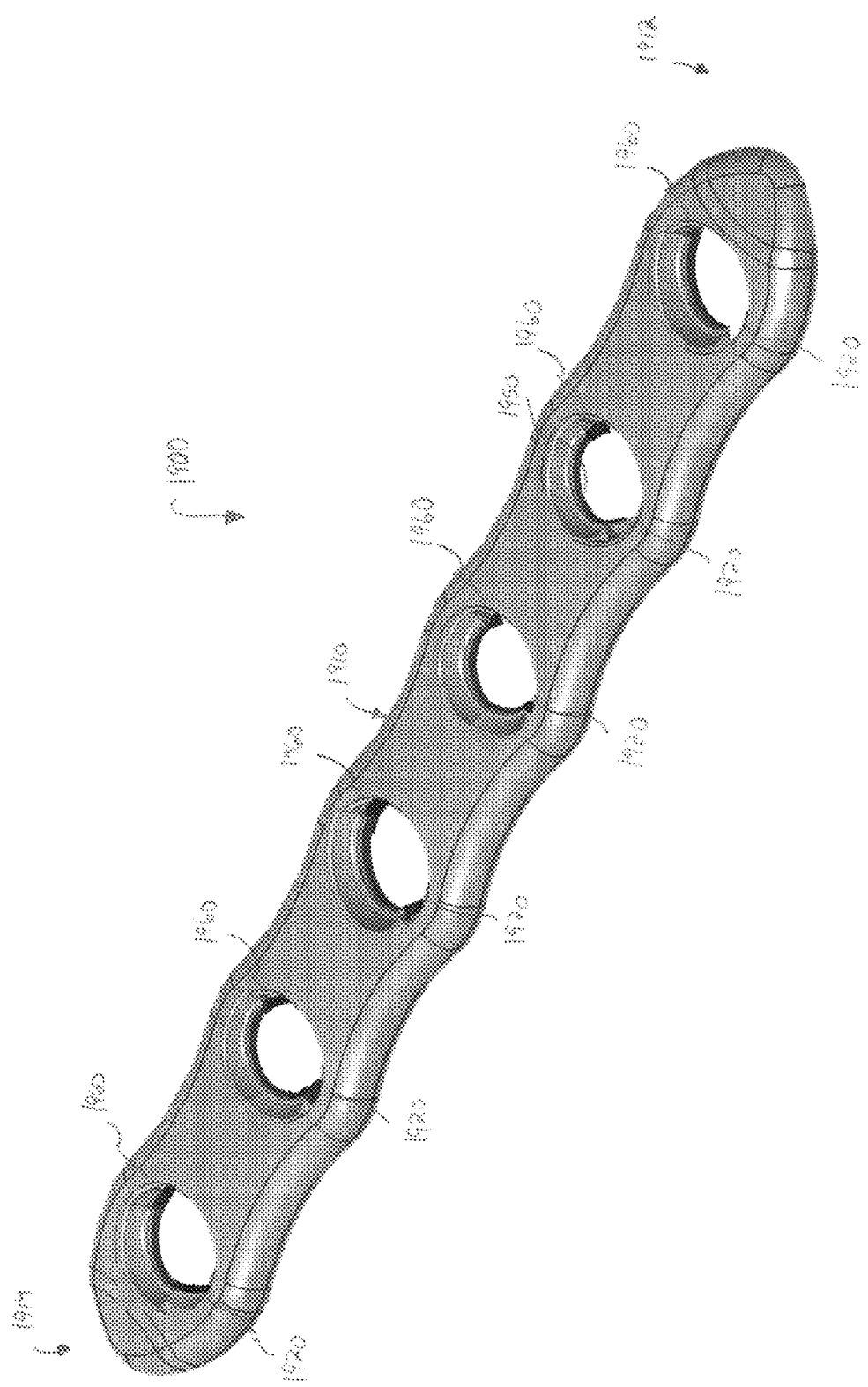
FIG. 33 illustrates a perspective view of the bone plate illustrated in FIG. 32.

FIGS. 32 and 33 illustrate another example bone plate 1900. The bone plate 1900 is similar to the bone plate 1600 described above, except as detailed below. The bone plate 1900 includes a main body 1910 and support member 1950.

The main body 1910 includes a main body first end 1912, a main body second end 1914, a main body lengthwise axis 1911 that extends from the main body first end 1912 to the main body second end 1914, a first surface 1915, a second surface 1917, a first set of openings 1920 that extends along the main body lengthwise axis 1911 and extends from the main body first end 1912 to the main body second end 1914, and a wall 1922 that extends from the main body first end 1912 to the main body second end 1914 and defines a groove 1980. Each opening of the first set of openings 1920 defines a recess 1970 that extends from the first surface 1915 to a recess base 1972, a first inner surface 1973, a second inner surface 1975, and a first circumferential surface 1977. The first surface 1915 is disposed on a first axis that is substantially parallel to the main body lengthwise axis 1911. The second surface 1917 is disposed on a second axis that is substantially parallel to the main body lengthwise axis 1911.

The first inner surface 1973 is disposed circumferentially about each opening of the first set of openings 1920 inside each recess 1970. Each recess base 1972 is disposed between the first surface 1915 and the second surface 1917 and is disposed closer to the second surface 1917. The second inner surface 1975 is disposed circumferentially about the recess base 1972 that faces toward the first surface 1915. The second inner surface 1975 of each opening of the first set of openings 1920 is sized and configured to interact with and directly contact a locking screw (e.g., locking screw 1500) during use. The first circumferential surface 1977 of each opening of the first set of openings 1920 extends from the recess base 1972 to the second surface 1917 along an axis that is perpendicular to the main body lengthwise axis 1911. The interaction between the second inner surface 1975 and the first circumferential surface 1977 of an opening of the first set of openings 1920 and a locking screw is considered advantageous at least because the second inner surface 1975 and the first circumferential surface 1977 provide a structural interface that secures the locking screw to the bone plate 1900 and prevents the locking screw from disengaging the bone plate 1900 once attached to the patient's bone.

The groove 1980 extends from the main body first end 1912 to the main body second end 1914. The groove 1980 extends away from the first set of openings 1920. The groove 1980 is considered advantageous at least because the groove 1980 provides an additional structural attachment between the main body 1910 and the support member 1950 once the support member 1950 is formed to the main body 1910.

The support member 1950 defines a third surface 1957, a fourth surface 1959, a second set of openings 1960, and a second circumferential surface 1989 defined by each opening of the second set of openings. The support member 1950 forms to the main body 1910. Specifically, the support member 1950 is attached to the wall 1922 and the groove 1980 such that the third surface 1957 and the second surface 1917 are in direct contact and attached to each other. The fourth surface 1959 interacts with and directly contacts the patient's bone once the bone plate 1900 is positioned on the patient's bone. Each opening of the second set of openings 1960 is directly adjacent to each recess base 1972 of each opening of the first set of openings 1920 and is in communication with each opening of the first set of openings 1920. The second circumferential surface 1989 extends from the third surface 1957 to the fourth surface 1959 along an axis that is perpendicular to the main body lengthwise axis 1911.

The structural configuration of the first circumferential surface 1977 and the second circumferential surface 1989 is considered advantageous at least because the first circumferential surface 1977 and the second circumferential surface 1989 provide a structural interface that allows the locking screw to engage both the main body 1910 and the support member 1950 simultaneously when attaching the bone plate 1900 to a patient's bone. The first circumferential surface 1977 of each opening of the first set of openings 1920 provides additional strength to the bone plate 1900 that allows a user, such as a surgeon, to apply a desired amount of torque onto the locking screw to ensure the locking screw is sufficiently secured to the bone plate 1900. The second circumferential surface 1989 of each opening of the second set of openings 1960 provides retention between the locking member and the second set of openings 1960 such that the support member 1950 acts as an additional locking feature to prevent the locking screw from disengaging the bone plate 1900. The second circumferential surface 1989 allows the thread of the locking screw to cut a matching threading into the second circumferential surface 1989 to structurally interface the locking screw with the support member 1950. The second set of openings 1960 also allows a user to introduce a locking screw at any suitable angle relative to the bone plate 1900.

The structural configuration of the main body 1910 and the support member 1950 of the bone plate 1900 can be included into any suitable bone plate described and illustrated above. Selection of an appropriate bone plate can be based on various considerations, including the attachment of the support member to the main body. Examples of bone plates that can include this structural configuration includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, bone plate 1900, and any other suitable bone plate that may include this structural configuration for a particular embodiment.

Figures 34, 35:
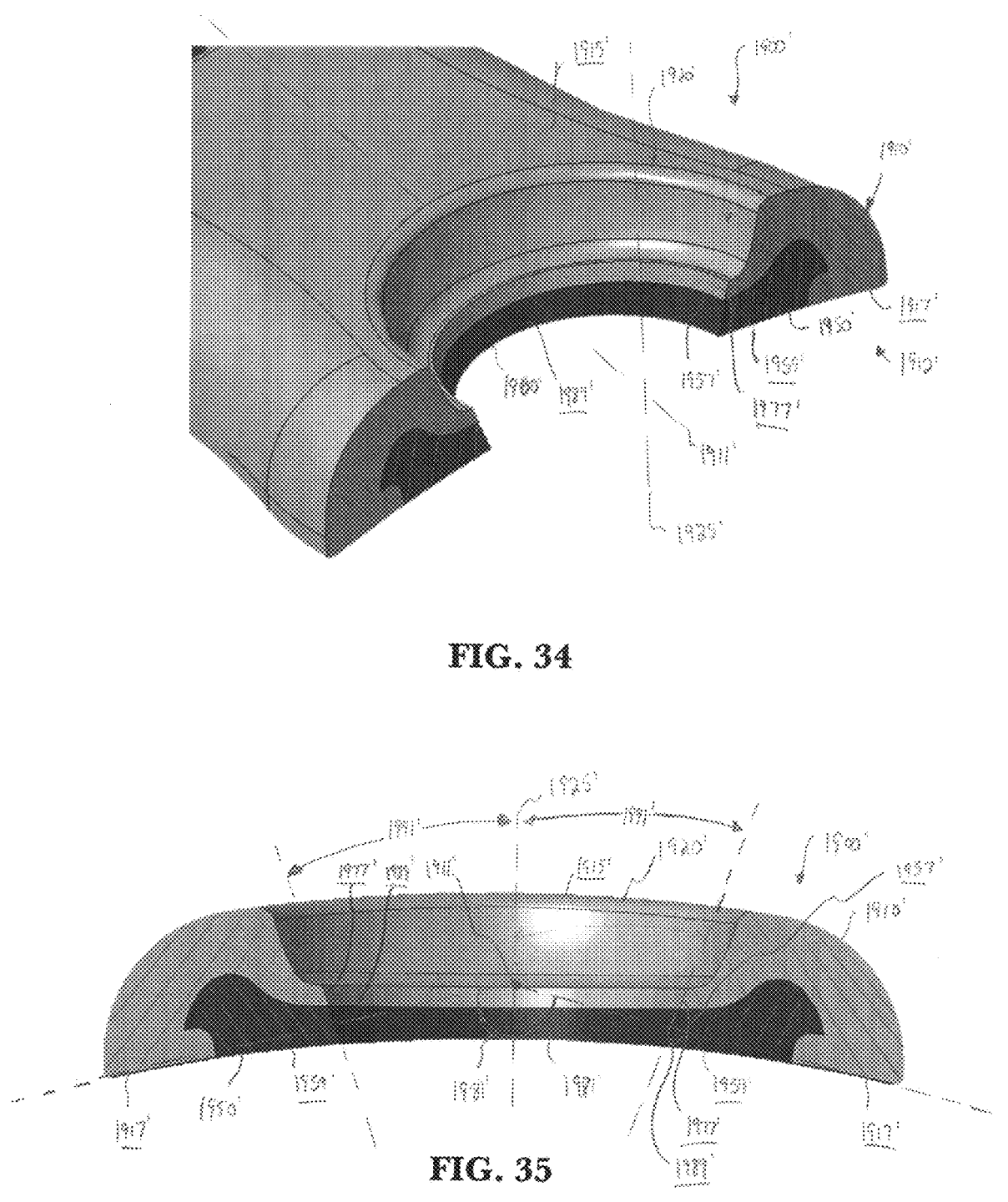

FIGS. 34 and 35 illustrate another example bone plate 1900'. The bone plate 1900' is similar to the bone plate 1900 described above, except as detailed below. The bone plate 1900' includes a main body 1910' and support member 1950'.

The main body 1910' includes a main body first end 1912', a main body second end (not illustrated), a main body lengthwise axis 1911' that extends from the main body first end 1912' to the main body second end, a first surface 1915', a second surface 1917', and a first set of openings 1920'. Each opening of the set of first openings 1920' defines an opening lengthwise axis 1925' that is perpendicular to the main body lengthwise axis 1911'. Each opening of the set of first openings 1920' also defines a first circumferential tapered surface 1977'. The support member 1950' defines a third surface 1957', a fourth surface 1959', a second set of openings 1960', and a second circumferential tapered surface 1989' defined by each opening of the second set of openings 1960'.

In the illustrated embodiment, a portion of each of the first surface 1915' and the third surface 1957' that is disposed circumferentially about each opening of the set of first openings 1920' is disposed on a first axis that is substantially perpendicular to the opening lengthwise axis 1925' of each opening of the first set of openings 1920'. Each of the second surface 1917' and the fourth surface 1959' is disposed on a second axis measured at an angle 1981' relative to the opening lengthwise axis 1925' of each opening of the set of first openings 1920'. The first circumferential tapered surface 1977' of each opening of the first set of openings 1920' extends from the recess base 1972' to the second surface 1917' along an axis that is disposed at an angle 1991' relative to the opening lengthwise axis 1925' of each opening of the first set of openings 1920'. The second circumferential surface 1989' extends from the third surface 1957' to the fourth surface 1959' along an axis that is disposed at the angle 1991' relative to the opening lengthwise axis 1925' of each opening of the first set of openings 1920'.

The structural attachment between the first circumferential tapered surface 1977' of an opening of the first set of openings 1920', the second circumferential tapered surface 1989' of an opening of the second set of openings 1960', and a locking screw is considered advantageous at least because the tapered-shape of both the first circumferential tapered surface 1977' and the second circumferential tapered surface 1989' match the tapered-shape of the locking screw. The tapered shapes provide a structural interface that secures the locking screw to the bone plate 1900 and prevents that bone plate 1900 from disengaging the locking screw once attached to the patient's bone. The first circumferential tapered surface 1977' of each opening of the first set of openings 1920' provides additional strength to the bone plate 1900' that allows a user, such as a surgeon, to apply a desired amount of torque onto the locking screw to ensure the locking screw is sufficiently secured to the bone plate 1900'. The second circumferential tapered surface 1989' of each opening of the second set of openings 1960' provides retention between the locking member and the second set of openings 1960' such that the support member 1950' acts as an additional locking feature to prevent the locking screw from disengaging the bone plate 1900'. The second circumferential tapered surface 1989' allows the thread of the locking screw to cut a matching threading into the second circumferential surface 1989' to structurally interface the locking screw with the support member 1950'. The second set of openings 1960' also allows a user to introduce a locking screw at any suitable angle relative to the bone plate 1900' in which the bone plate 1900'.

The structural configuration of the main body 1910' and the support member 1950' of the bone plate 1900' can be included into any suitable bone plate described and illustrated above. Selection of an appropriate bone plate can be based on various considerations, including the attachment of the support member to the main body. Examples of bone plates that can include this structural configuration includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, bone plate 1900, and any other suitable bone plate that may include this structural configuration for a particular embodiment.

Figure 36:
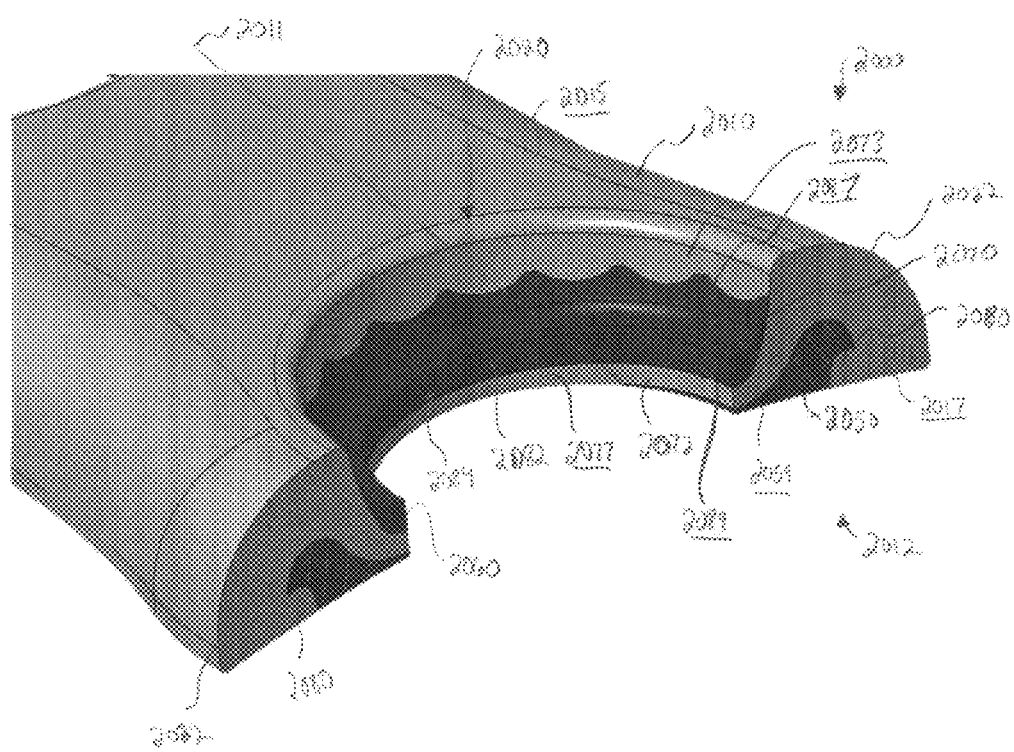
FIG. 36 illustrates a partial cross-sectional view of another example bone plate.
Figure 37:
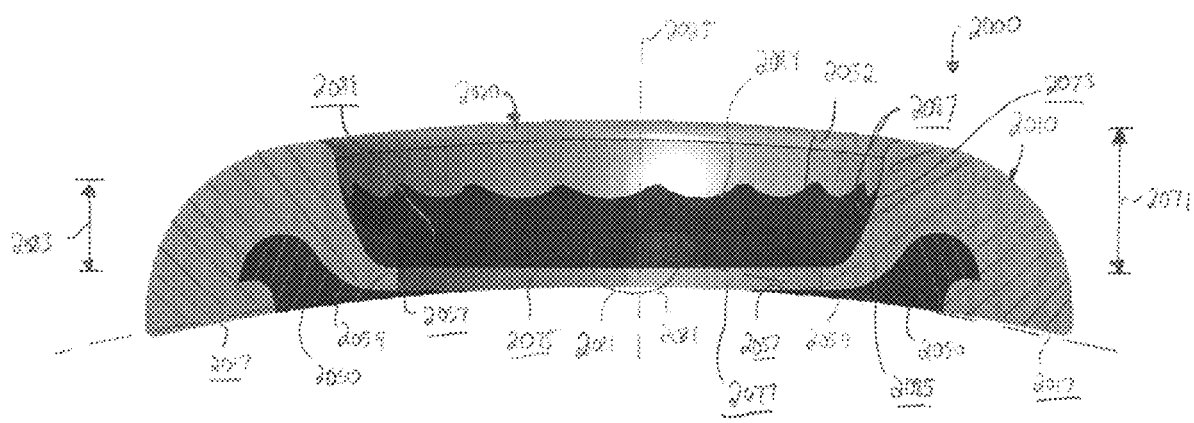
FIG. 37 illustrates another cross-sectional view of the bone plate illustrated in FIG. 36.

FIGS. 36 and 37 illustrate another example bone plate 2000. The bone plate 2000 is similar to the bone plate 1900 described above, except as detailed below. The bone plate 2000 includes a main body 2010, a first support member 2050, and a set of second support member 2082.

The main body 2010 includes a main body first end 2012, a main body second end (not illustrated), a main body lengthwise axis 2011 that extends from the main body first end 2012 to the main body second end, a first surface 2015, a second surface 2017, a first set of openings 2020, and a wall 2022 that defines a groove 2080. Each opening of the first set of openings 2020 defines a recess 2070 that extends from the first surface 2015 to a recess base 2072 and defines a recess length 2071, a first inner surface 2073, a second inner surface 2075, and a first circumferential surface 2077.

The first inner surface 2073 is disposed circumferentially about each opening of the first set of openings 2020 inside each recess 2070. The recess base 2072 of each opening of the first set of openings 2020 is disposed between first surface 2015 and the second surface 2017 and is closer to the second surface 2017. The second inner surface 2075 is disposed circumferentially about the recess base 2072 and faces the first surface 2015. The second inner surface 2075 of each opening of the first set of openings 2020 is sized and configured to interact with and directly contact a locking screw (e.g., locking screw 1500) during use. The first circumferential surface 2077 of each opening of the first set of openings 2020 extends from the recess base 2072 to the second surface 2017 along an axis that is perpendicular to the main body lengthwise axis 2011. The interaction between the first circumferential surface 2077 of an opening of the first set of openings 2020 and a locking screw is considered advantageous at least because the first circumferential surface 2077 provides a structural interface that secures the locking screw to the bone plate 2000 and prevents the locking screw from disengaging the bone plate 1900 once attached to the patient's bone. Alternatively, the first circumferential surface 2077 can extend along an axis that is disposed at an angle relative to the opening lengthwise axis 2025 of an opening of the first set of openings 2020 such that the first circumferential surface 2077 defines a tapered-shape similar to the first circumferential tapered surface 1977'.

The groove 2080 extends from the main body first end 2012 to the main body second end 2014. The groove 2080 extends away from the first set of openings 2020. The groove 2080 is considered advantageous at least because the groove 2080 provides an additional structural attachment between the main body 2010 and the support member 2050 once the support member 2050 is formed to the main body 2010.

The first support member 2050 defines a third surface 2057, a fourth surface 2059, and a second set of openings 2060. The first support member 2050 forms to the main body 2010. Specifically, the first support member 2050 is attached to the wall 2022 such that the third surface 2057 and the second surface 2017 are in direct contact and attached to each other. The fourth surface 2059 interacts with and directly contacts the patient's bone once the bone plate 2000 is positioned on the patient's bone. Each opening of the second set of openings 2060 is directly adjacent to each recess base 2072 of the each opening of the first set of openings 2020 and is in communication with each opening of the first set of openings 2020.

Each second support member of the set of second support members 2082 is disposed within each opening of the set of first openings 2020. Each second support member 2082 defines a fifth surface 2085, a sixth surface 2087, an opening 2084, and a second circumferential surface 2089. Each second support member 2082 forms to the main body 2010. Specifically, each second support member 2082 forms to each opening of the first set of openings 2020 such that the fifth surface 2085 attaches to a portion of the first inner surface 2073 at length 2083 that is measured from the recess base 2072 toward the first surface 2015. The length 2083 is less than the recess length 2071. Each second support member 2082 forms to each opening of the first set of openings 2020 such that the fifth surface 2085 attaches to the second inner surface 2075. The sixth surface 2087 faces opposite to the fifth surface 2085 and interacts with and directly contacts a locking screw during use. Each opening 2084 of each second support member 2052 is circumferentially disposed about each opening of the first set of openings 2020. The second circumferential surface 2089 extends from the recess base 2072 toward the first surface 2015 along an axis that is perpendicular to the main body lengthwise axis 2011. Alternatively, the second circumferential surface 2089 can extend along an axis that is disposed at an angle relative to the opening lengthwise axis 2025 of an opening of the first set of openings 2020 such that the second circumferential surface 2089 defines a tapered-shape similar to the second circumferential tapered surface 1989'.

The structural configuration of the first circumferential surface 2077 and the second circumferential surface 2089 is considered advantageous at least because the first circumferential surface 2077 and the second circumferential surface 2089 provide a structural interface that allows the locking screw to engage both the main body 2010 and the support member 2050 simultaneously when attaching the bone plate 2000 to a patient's bone. The first circumferential surface 2077 of each opening of the first set of openings 2020 provides additional strength to the bone plate 2000 that allows a user, such as a surgeon, to apply a desired amount of torque onto the locking screw to ensure the locking screw is sufficiently secured to the bone plate 2000. The second circumferential surface 2089 of each opening of the second set of openings 2060 provides retention between the locking member and the second set of openings 2060 such that the support member 2050 acts as an additional locking feature to prevent the locking screw from disengaging the bone plate 2000. The second circumferential surface 2089 allows the thread of the locking screw to cut a matching threading into the second circumferential surface 2089 to structurally interface the locking screw with the support member 2050. The second set of openings 2060 also allows a user to introduce a locking screw at any suitable angle relative to the bone plate 2000.

In the illustrated embodiment, each opening of the first set of openings 2020 defines an opening lengthwise axis 2025 that is perpendicular to the main body lengthwise axis 2011. A portion of each of the first surface 2015 and the third surface 2057 that is disposed circumferentially about each opening of the set of first openings 2020 is disposed on a first axis that is substantially perpendicular to the opening lengthwise axis 2025 of each opening of the first set of openings 2020. Each of the second surface 2017 and the fourth surface 2059 is disposed on a second axis that is not substantially perpendicular to the opening lengthwise axis 2025 of each opening of the set of first openings 2020. Each of the second surface 2017 and the fourth surface 2059 is disposed at an angle 2081 relative to the opening lengthwise axis 2025 of each opening of the set of first openings 2020. Alternatively, each of the second surface 2017 and the fourth surface 2059 can be substantially perpendicular to the opening lengthwise axis 2025 of each opening of the first set of openings 2020.

The structural configuration of the main body 2010, the first support member 2050, and the set of second support member 2082 of the bone plate 2000 can be included into any suitable bone plate described and illustrated above. Selection of an appropriate bone plate can be based on various considerations, including the attachment of each support member to the main body. Examples of bone plates that can include this structural configuration includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, bone plate 1900, bone plate 1900', and any other suitable bone plate that may include this structural configuration for a particular embodiment.

Figure 38:
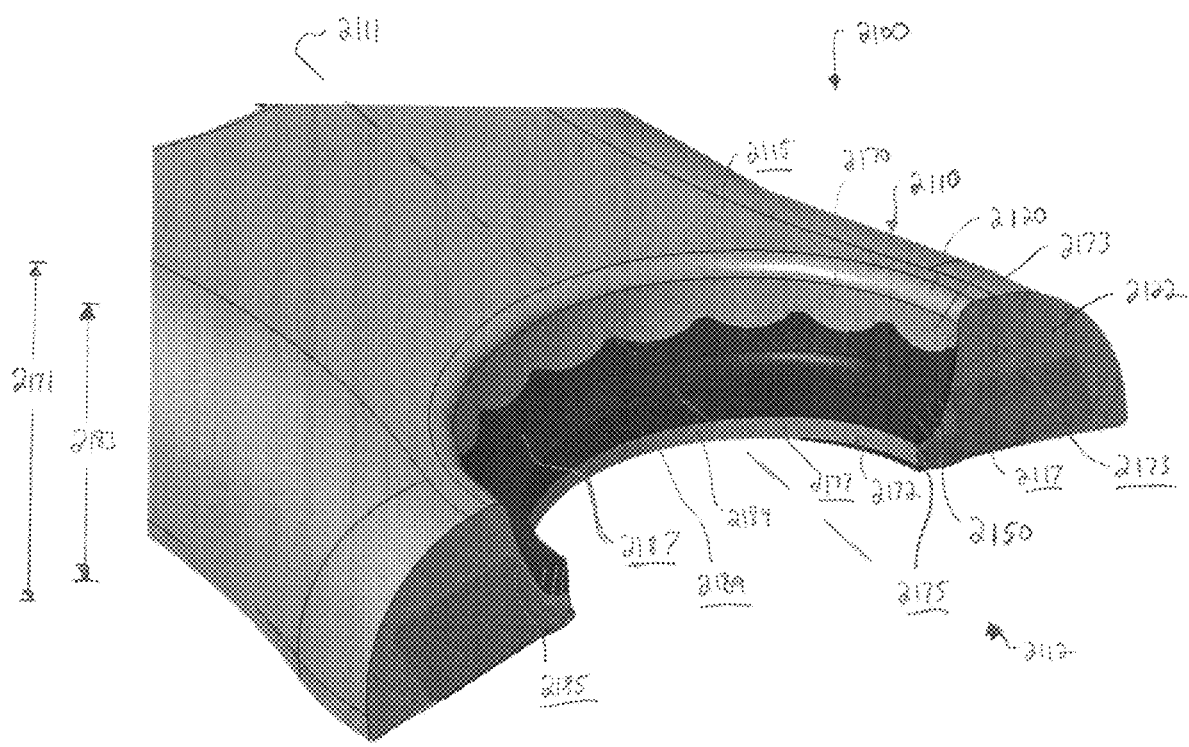
FIG. 38 illustrates a partial cross-sectional view of another example bone plate.

FIG. 38 illustrates another example bone plate 2100. The bone plate 2100 is similar to the bone plate 1900 described above, except as detailed below. The bone plate 2100 includes a main body 2110 and a set of support members 2150.

The main body 2110 includes a main body first end 2112, a main body second end (not illustrated), a main body lengthwise axis 2111 that extends from the main body first end 2112 to the main body second end, a first surface 2115, a second surface 2117, a first set of openings 2120, and a wall 2122. Each opening of the first set of openings 2120 defines a recess 2170 that extends from the first surface 2115 to a recess base 2172 and defines a recess length 2171, a first inner surface 2173, a second inner surface 2175, and a first circumferential surface 2177.

The first inner surface 2173 is disposed circumferentially about each opening of the first set of openings 2120 inside each recess 2170. The recess base 2172 of each opening of the first set of openings 2120 is disposed between first surface 2115 and the second surface 2117 and is closer to the second surface 2117. The second inner surface 2175 is disposed circumferentially about the recess base 2172 and faces the first surface 2115. The second inner surface 2175 of each opening of the first set of openings 2120 is sized and configured to interact with and directly contact a locking screw (e.g., locking screw 1500) during use. The first circumferential surface 2177 of each opening of the first set of openings 2120 extends from the recess base 2172 to the second surface 2117 along an axis that is perpendicular to the main body lengthwise axis 2111. The interaction between the first circumferential surface 2177 of an opening of the first set of openings 2120 and a locking screw is considered advantageous at least because the first circumferential surface 2177 provides a structural interface that secures the locking screw to the bone plate 2100 and prevents the locking screw from disengaging the bone plate 2100 once attached to the patient's bone. Alternatively, the first circumferential surface 2177 can extend along an axis that is disposed at an angle relative to the opening lengthwise axis 2125 of an opening of the first set of openings 2120 such that the first circumferential surface 2177 defines a tapered-shape similar to the first circumferential tapered surface 1977'.

The set of support members 2150 is disposed within each opening of the first set of openings 2120 in which each support member of the set of support members 2150 defines a fifth surface 2185, a sixth surface 2187, an opening 2184, and a second circumferential surface 2189. Each support member of the set of support members 2150 forms to the main body 2110. Specifically, each support member of the set of support members 2150 forms to each opening of the first set of openings 2120 such that the fifth surface 2185 attaches to a portion of the first inner surface 2173 at length 2183 that is measured from the recess base 2172 toward the first surface 2115. The length 2183 is less than the recess length 2171. Each support member of the set of support member 2150 also attaches to the recess base 2172 of each opening of the first set of openings 2120 such the fifth surface 2815 attaches to the second inner surface 2175. The sixth surface 2187 faces opposite to the fifth surface 2185 and interacts with and directly contacts a locking screw during use. Each opening 2184 of each support member of the set of support members 2150 is circumferentially disposed about each opening of the first set of openings 2120. The second circumferential surface 2189 extends from the recess base 2172 toward the first surface 2115 along an axis that is perpendicular to the main body lengthwise axis 2111. Alternatively, the second circumferential surface 2189 can extend along an axis that is disposed at an angle relative to the opening lengthwise axis 2125 of an opening of the first set of openings 2120 such that the second circumferential surface 2189 defines a tapered-shape similar to the second circumferential tapered surface 1989'.

The structural configuration of the main body 2110 and the set of support members 2150 is considered advantageous at least because the main body 2110 and the set of support members 2150 provide a structural interface that allows the locking screw to engage both the main body 2110 and the support member 2150 simultaneously when attaching the bone plate 2100 to a patient's bone. The set of support members 2050 provides additional retention between the locking member the bone plate 2100 such that each support member of the set of support members 2150 acts as an additional locking feature to prevent the locking screw from disengaging the bone plate 2100. The structural configuration of the set of support members 2150 allows a user to introduce a locking screw at any suitable angle in which the bone plate 2100 can be secured to a desired location on the patient's bone.

The structural configuration of the main body 2110 and the set of support member 2150 of the bone plate 2100 can be included into any suitable bone plate described and illustrated above. Selection of an appropriate bone plate can be based on various considerations, including the attachment of the support member to the main body. Examples of bone plates that can include this structural configuration includes bone plate 100, bone plate 200, bone plate 300, bone plate 300', bone plate 400, bone plate 500, bone plate 600, bone plate 700, bone plate 800, bone plate 900, bone plate 1000, bone plate 1100, bone plate 1100', bone plate 1200, bone plate 1300, bone plate 1500, bone plate 1900, bone plate 1900', bone plate 2000, and any other suitable bone plate that may include this structural configuration for a particular embodiment.

The process of manufacturing a bone plate that is illustrated and described in the present application may be performed by a molding process. The molding process of a bone plate is performed by forming a support member to and/or about a main body of a bone plate. As such, a support member can be formed to the main body of a bone plate by use of injection molding. The injection molding process is performed by introducing a mold to the main body such that the mold would be positioned on and/or about the wall and the main body. Once the mold is positioned, a molten material is injected into the mold to create a support member. The material used during the injection molding process may be any suitable material, which is described in detail below. Once injected, the molten material forms inside the mold to create the support member. Additionally, the molten material of the support member attaches to the wall and the main body. Once the support member is formed and attached to the wall and the main body, the bone plate is produced, and the mold is removed from the bone plate. The use of injection molding to create a bone plate is considered advantageous at least because the injection molding process allows for improved flexibility in the bone plate shape, especially for anatomically shaped plates, compared to conventional machining. Furthermore, injection molding also allows for atypical shapes and sizes to form the support member to the main body in comparison to traditional bone plates.

Additionally, the manufacturing of the bone plate illustrated and described in the present application may use a compression molding process to form the support member to the main body. The compression molding process is performed by introducing a mold to the main body. Before the main body is introduced to the mold, the mold is preheated to a desired temperature to help form the support member to the main body during the molding process. Once preheated, the mold is introduced to the main body. Once the main body is introduced, the material used to create the support member is also preheated and is positioned on and/or about the main body. The material used during the compression molding process may be any suitable material, such as pre-impregnated fibers or other materials as described in detail below. Once the material of the support member is positioned, the mold compresses the material of the support member into the main body such that the support member is formed, and the support member attaches to the wall and the main body cooperatively. Once the support member is compressed and formed to the main body, the bone plate is produced and is removed from the mold.

The use of compression molding to create a bone plate is considered advantageous at least because the compression molding process allows a support member to be created with complex shapes and sizes. Furthermore, these complex shapes and sizes for a support member also allows a bone plate to be structurally configured with similar complex shapes and sizes, which could be suitable for certain bone plates such as anatomically shaped plates based on the structure of the patient's bone and the placement of screws into a patient's bone. Examples of suitable shapes for a bone plate that are described herein include T-shaped, X-shaped, S-shaped, L-shaped, box-shaped, and any other suitable shapes for a particular application.

The processes of injection molding and/or compression molding to bond a support member to a main body is considered advantageous at least because these molding processes provide additional strength between a main body and a support member during use. Specifically, the additional strength provided by either molding process prevents delamination between the main body and the support member such that no loose material is disposed within the patient's body once a bone plate is fixed within the patient's body. To prevent delamination, the main body of a selected bone plate comprises a surface treatment, such as roughening, coating, and other similar treatments, to allow the support member to adhere to the main body when the support member is in its molten liquid and high pressure state. The surface treatment made to the main body can be used on any main body of any bone plate described herein.

The main body of a bone plate according to an embodiment can be made from any material suitable for use in medical devices intended for orthopedic use, including use as a long-term implant. Examples of suitable materials include Titanium, Magnesium, and other suitable materials metals for this particular application. Examples of suitable metal alloys include stainless steel (316L), cobalt alloys, pure titanium, titanium alloys, magnesium alloys, molybdenum alloys, zirconium alloys, Ti6Al4V, 316 LVM, 1.4441Ti-13Nb-13Zr, Ti-12Mo-6Zr-2Fe, Ti-15Mo-5Zr-3Al, Ti15Mo, Ti-35Nb-7Zr-5Ta and Ti-29Nb-13Ta-4.6Zr Ti-6Al-7Nb and Ti-15 Sn-4Nb-2Ta-0.2Pd Co—Cr—Mo alloys.

The main body can be treated in a manner that prepares the main body for bonding, contact, or other interface with the support member. If a surface treatment is included, any suitable surface treatment can be used and a skilled artisan will be able to select a suitable surface treatment for an intramedullary rod according to a particular embodiment based on various considerations, such as the materials of the main body and the support member. Examples of suitable surface treatments include roughening, etching, and other surface treatments. Also, the portion or portions of the outer surface on the main body that will not contact the support member during manufacturing of the bone plate can be left untreated or treated in a different manner than the portion or portions that will contact the support member during manufacturing. Inclusion of a surface treatment is considered particularly advantageous for embodiments in which the support member is injection molded onto the main body because the presence of the surface treatment, in combination with the high heat and high pressure of the injection molding process facilitates bonding of the support member to the main body. This is particularly true in embodiments in which the main body comprises a metal, such as Titanium or a titanium alloy, and the support member comprises polyether ether ketone (PEEK), or carbon fiber-reinforced PEEK.

Additionally, the support member in a bone plate according to an embodiment can be made from any material suitable for use in medical devices intended for orthopedic use, including use as a long-term implant. Examples of suitable materials include polymeric materials, including plastic metals currently considered suitable for use in medical device, carbon fiber, polyaryletherketone (PAEK), polyether ether ketone (PEEK), PEEK (90G, 450G, I2, I4), Polyamid, PA66, carbon fiber reinforced polyaryletherketone (CFR PAEK), polyethere ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, 12 CF20, 12 CF30, 14 CF30, 14 CF20), Polyamid CFR, PA66 CFR, and any other suitable materials for a particular purpose. The inventors have determined that, for embodiments in which the support member includes carbon fiber, it is considered advantageous to include carbon fiber in the material of the support member at an amount that represents a balance between the desirable strength carbon fiber provides and any offsets it contributes to the contourability of the bone plate due to the brittleness of the material. For plates that include a support member comprising carbon fiber reinforced polyether ether ketone (CFR PEEK), it is considered advantageous to include carbon fiber in PEEK at an amount that is less than 5% on a volume basis. It is also considered advantageous to include carbon fiber in PEEK at an amount that is less than 2.5% on a volume basis. It is also considered advantageous to include carbon fiber in PEEK at an amount that is less than 1% on a volume basis. It is also considered advantageous to include carbon fiber in PEEK at an amount that is less than 0.1% on a volume basis. It is also considered advantageous to include carbon fiber in PEEK at an amount that is less than 0.01% on a volume basis.

A bone plate illustrated and described in the present application can be performed by conventional manufacturing techniques, processes, and equipment. A skilled artisan will be able to select a suitable method of manufacturing a bone plate according to an embodiment based on various considerations, including the size, shape, and configuration of a patient's bone, the size of a patient's bone fracture, types of screws, fasteners, or medical devices used in conjunction during implantation, and other considerations. Examples of suitable manufacturing techniques include Computer Numerical Control (CNC) milling machine, additive manufacturing (e.g. 3D printing), injection molding, compression molding, and any other manufacturing techniques, processes, and equipment considered suitable for a particular application of making a bone plate.

The foregoing detailed description refers to various examples of bone plates. The description and appended drawings illustrating the described bone plates are intended to only provide examples and not to limit the scope of the claims in any manner.

We claim:

1. A bone fixation plate, comprising:
a main body formed of a first material, the main body having a main body first end, a main body second end, a main body first side, a main body second side, a first surface, and a second surface opposite the first surface, the main body defining a first set of openings extending through the main body between the first and second surfaces and a main body circumferential surface for each opening of the first set of openings; and
a support member formed of a second, different material and attached to the main body, the support member defining a second set of openings aligned with the first set of openings and a support member circumferential surface for each opening of the second set of openings;
wherein each main body circumferential surface is disposed adjacent and continuous with a support member circumferential surface to define an opening circumferential surface that bounds an opening of the first set of openings and an opening of the second set of openings;
wherein the main body defines a recess for each opening of the first set of openings, each recess extending to the main body circumferential surface for the respective opening of the first set of openings.

2. The bone fixation plate of claim 1, wherein an opening axis extends through each opening of the first set of openings; and wherein each recess defines a recess surface disposed at a first angle to the opening axis of the respective opening of the first set of openings.

3. The bone fixation plate of claim 2, wherein the main body circumferential surface is parallel to the opening axis of the respective first set of openings.

4. The bone fixation plate of claim 3, wherein the support member circumferential surface is parallel to the opening axis of the respective first set of openings.

5. The bone fixation plate of claim 2, wherein the main body circumferential surface is disposed at a non-orthogonal angle to the opening axis of the respective first set of openings.

6. The bone fixation plate of claim 5, wherein the support member circumferential surface is disposed at a non-orthogonal angle to the opening axis of the respective first set of openings.

7. The bone fixation plate of claim 2, wherein the main body circumferential surface is disposed at a first non-orthogonal angle to the opening axis of the respective first set of openings;
wherein the support member circumferential surface is disposed at a second non-orthogonal angle to the opening axis of the respective first set of openings; and
wherein the first and second non-orthogonal angles are the same.

8. The bone fixation plate of claim 1, wherein a first opening of the first set of openings has a first inner diameter; and
wherein a second opening of the second set of openings and adjacent the first opening has a second inner diameter that is different than the first inner diameter.

9. The bone fixation plate of claim 8, wherein the second inner diameter is less than first inner diameter.

10. The bone fixation plate of claim 8, wherein the second inner diameter is greater than first inner diameter.

11. The bone fixation plate of claim 1, wherein the first material comprises a metal.

12. The bone fixation plate of claim 11, wherein the second material comprises a non-metal.

13. The bone fixation plate of claim 1, wherein the first material comprises one or more of Titanium, Magnesium, Ti6A14V, 316 LVM, 1.4441Ti-13Nb-13Zr, Ti-12Mo-6Zr-2Fe, Ti-15Mo-5Zr-3A1, Ti-15Mo, Ti-35Nb-7Zr-5Ta and Ti-29Nb-13Ta-4.6Zr Ti-6A1-7Nb and Ti-15Sn-4Nb-2Ta-0.2Pd Co—Cr—Mo alloys.

14. The bone fixation plate of claim 1, wherein the second material comprises one or more of PAEK, CFR PAEK, PEKK, CFR PEKK, PEEK, CFR-PEEK, PEEK (90G, 450G, 12, 14), Polyamid, and PA66.

15. The bone fixation plate of claim 1, wherein the first material comprises a Titanium alloy and the second material comprises PEEK.

16. The bone fixation plate of claim 1, wherein the support member comprises an overmolded structure formed on the main body.

17. A bone fixation plate, comprising:
a main body formed of a metal, the main body having a main body first end, a main body second end, a main body first side, a main body second side, a first surface, and a second surface opposite the first surface, the main body defining a first set of openings extending through the main body between the first and second surfaces and a main body circumferential surface for each opening of the first set of openings; and
a support member formed of a non-metal and attached to the main body, the support member defining a second set of openings aligned with the first set of openings and a support member circumferential surface for each opening of the second set of openings;
wherein each main body circumferential surface is disposed adjacent and continuous with a support member circumferential surface to define an opening circumferential surface that bounds an opening of the first set of openings and an opening of the second set of openings;
wherein a first opening of the first set of openings has a first inner diameter; and
wherein a second opening of the second set of openings and adjacent the first opening has a second inner diameter that is the same as the first inner diameter;
wherein the main body defines a recess for each opening of the first set of openings, each recess extending to the main body circumferential surface for the respective opening of the first set of openings.

18. A bone fixation plate, comprising:

a main body formed of a metal, the main body having a main body first end, a main body second end, a main body first side, a main body second side, a first surface, and a second surface opposite the first surface, the main body defining a first set of openings extending through the main body between the first and second surfaces and a main body circumferential surface for each opening of the first set of openings; and a support member formed of a non-metal and attached to the main body, the support member defining a second set of openings aligned with the first set of openings and a support member circumferential surface for each opening of the second set of openings;

wherein each main body circumferential surface is disposed adjacent and continuous with a support member circumferential surface to define an opening circumferential surface that bounds an opening of the first set of openings and an opening of the second set of openings;

wherein a first opening of the first set of openings has a first inner diameter; and wherein a second opening of the second set of openings and adjacent the first opening has a second inner diameter that is less than the first inner diameter;

wherein the main body defines a recess for each opening of the first set of openings, each recess extending to the main body circumferential surface for the respective opening of the first set of openings.

* * * * *

UNITED STATES PATENT AND TRADEMARK OFFICE
CERTIFICATE OF CORRECTION

PATENT NO. : 11,628,000 B2
APPLICATION NO. : 16/822243
DATED : April 18, 2023
INVENTOR(S) : Thomas Hoon Lee et al.

It is certified that error appears in the above-identified patent and that said Letters Patent is hereby corrected as shown below:

In the Claims

Column 44, Claim 14, Line 34, please correct:
"450G, 12, 14),"

To:
--450G, I2, I4),--

Signed and Sealed this
Twentieth Day of June, 2023

*Katherine Kelly Vidal*

Katherine Kelly Vidal
*Director of the United States Patent and Trademark Office*